(12) United States Patent
Kaplan et al.

(10) Patent No.: US 11,548,942 B2
(45) Date of Patent: *Jan. 10, 2023

(54) METHODS OF TREATING A WASTING SYNDROME, INCREASING GROWTH HORMONE LEVELS, AND INCREASING GHSR ACTIVITY WITH A LEAP2 ANTIBODY

(71) Applicant: NGM Biopharmaceuticals, Inc., South San Francisco, CA (US)

(72) Inventors: Daniel David Kaplan, San Mateo, CA (US); Xuecai Ge, Menlo Park, CA (US); Hui Tian, Foster City, CA (US)

(73) Assignee: NGM Biopharmaceuticals, Inc., South San Francisco, CA (US)

( * ) Notice: Subject to any disclaimer, the term of this patent is extended or adjusted under 35 U.S.C. 154(b) by 14 days.

This patent is subject to a terminal disclaimer.

(21) Appl. No.: 16/993,974

(22) Filed: Aug. 14, 2020

(65) Prior Publication Data
US 2021/0101973 A1    Apr. 8, 2021

Related U.S. Application Data

(63) Continuation of application No. 15/987,766, filed on May 23, 2018, now Pat. No. 10,781,253.

(60) Provisional application No. 62/510,668, filed on May 24, 2017.

(51) Int. Cl.
| | | |
|---|---|---|
| A61K 38/16 | (2006.01) | |
| C07K 16/26 | (2006.01) | |
| C07K 16/18 | (2006.01) | |
| A61K 39/05 | (2006.01) | |
| A61K 38/04 | (2006.01) | |
| A61K 39/00 | (2006.01) | |

(52) U.S. Cl.
CPC ............. *C07K 16/26* (2013.01); *A61K 39/05* (2013.01); *C07K 16/18* (2013.01); *A61K 38/04* (2013.01); *A61K 2039/505* (2013.01)

(58) Field of Classification Search
None
See application file for complete search history.

(56) References Cited

U.S. PATENT DOCUMENTS

| 8,389,679 B2 | 5/2013 | Eckert et al. |
|---|---|---|
| 10,781,253 B2 | 9/2020 | Kaplan et al. |
| 2018/0371080 A1 | 12/2018 | Kaplan et al. |

FOREIGN PATENT DOCUMENTS

WO    WO 2004/101615    11/2004

OTHER PUBLICATIONS

Atalayer et al. Prog. Neuropsychopharmacol. Biol. Psychiatry. 40: 70-82, 2013.*
Khatib et al. Cochrane Database of Systematic Reviews, 2018, 71 pages https://doi.org/10.1002/14651858.CD012229.pub2.*
Akamizu et al. J. Cachexia Sarcopenia Muscle. 1: 169-176, 2010.*
Altabas et al., "Anti-glirelin antibodies in appetite suppression: recent advances in obesity pharmacotherapy," ImmunoTargets and Therapy, 2015, 4:123-130.
Azizzadeh et al., "Ghrelin Exerts Analgesic Effects through Modulation of IL-10 and TGF--[) Levels in a Rat Model of Inflammatory Pain," Iran. Biomed. J., 2017, 21(2):114-119.
Baggio et al., "Biology of incretins: GLP-1 and GIP," Gastroenterology, 2007, 132:2131-2157.
Bays, "Current and investigational Antiobesity Agents and Obesity Therapeutic Treatment Targets," Obesity Research, 2004, 12(8):1197-1211.
Betley et al., "Parallel, Redundant Circuit Organization for Homeostatic Control of Feeding Behavior," Cell, 2013, pp. 1337-1350.
Borg et al., "Progressive rise in gut hormone levels after Roux-en-Y gastric bypass suggests gut adaptation and explains altered satiety," British Journal of Surgerv, 2006, 93:210-215.
Bouzo-Lorenzo et al., "Distinct phosphorylation sites on the ghrelin receptor, GHSR la, establish a code that determines the functions of [3-arrestins." Scientific Reports, 2016, 6:22495, pp. 1-14.
Cahill, "Fuel Metabolism in Starvation," Annual Reviews of Nutrition, 2006, 26:1-22.
Cao et al., "Cardioprotective Effect of Ghrelin in Cardiopulmonary Bypass Involves a Reduction in Inflammatory Response," PLOS One, 2013, 8(1):e55021, pp. 1-9.
Chebani et al., "Enhanced responsiveness of GhsrQ343X rats to ghrelin results in enhanced adiposity without appetite," Science Signaling, 2016, 9(424):1-10.
Chollet et al., "Ghrelin—a novel generation of anti-obesity drug: design, pharmacomodulation and biological activity of ghrelin analogues," J. Pept. Sci., 2009. 15:711-730.
Churm et al., "Ghrelin function in human obesity and type 2 diabetes: a concise review," Obesity reviews, 2016, pp. 1-9.
Cohen et al., "Diabetes remission without weight loss after duodenal bypass surgery," Surgery for Obesity and Related Diseases, 2012, 8:e66-e68.
Cruz et al., "The Growth Hormone Secretagogue Receptor," Vitamins & Hormones, 2008, 177:47-88.

(Continued)

*Primary Examiner* — Christine J Saoud
(74) *Attorney, Agent, or Firm* — Fish & Richardson P.C.

(57) ABSTRACT

The present disclosure provides binding agents that modulate the interaction between liver-expressed antimicrobial peptide 2 (LEAP2) and growth hormone secretagogue receptor (GHSR). Specifically, the present disclosure provides binding agents, such as LEAP2 peptides that bind GHSR and methods of their use to treat or ameliorate a neuroendocrine and/or metabolic disease or disorder such as obesity, diabetes, acromegaly, gigantism and/or Prader-Willi syndrome. The present disclosure also provides binding agents, such as antibodies, that bind LEAP2, and methods of their use to, e.g., treat or ameliorate a neuroendocrine and/or metabolic disease or disorder such as cachexia, anorexia, or other wasting syndromes, increase growth hormone levels, or increase GHSR activity.

32 Claims, 12 Drawing Sheets

Specification includes a Sequence Listing.

(56) References Cited

OTHER PUBLICATIONS

Cummings et al., "Melanocortins and body weight: A tale of two receptors," Nature Genetics, 2.000, 26:8-9.
Cummings et al., "Plasma Ghrelin Levels after Diet-Induced Weight Loss or Gastric Bypass Surgery," The New England Journal Medicine, 2002, 346:1623-1630.
Damian et al., (2015) "Ghrelin receptor conformational dynamics regulate the transition from a preassembled to an active receptor: GQ Complex," PNAS, 112(5):1601-1606.
Engel et al., "A ghrelin receptor (GHS-R1A) antagonist attenuates the rewarding properties of morphine and increases opioid peptide levels in reward areas in mice." ELSEVIER, 2015, 25:2364-2371.
Erden et al., "Serum Ghrelin Levels in Patients with Behcet's Disease." Advances in Dermatology and Allergology, 2016, pp. 450-456.
Eslami et al., "Recent developments in liquid chromatography-mass spectrometry analyses of ghrelin and related peptides," Biomedical Chromatography, 2017, 31:e3796, 1-13.
Fujitsuka et al., "Potentiation of ghrelin signaling attenuates cancer anorexia-cachexia and prolongs survival," Transl. Psychiatry, 2.011, 1(e23):1-10.
Galon-Tilleman et al., Apelin-36 Modulates Blood Glucose and Body Weight Independently of Canonical APJ Receptor Signaling, Journal of Biological Chemistry, 2017, 292:1925-1933.
Hansen et al., "Pharmacological characterisation of a new oral GH secretagogue, NN703," European Journal of Endocrinology, 1999, 141:180-189.
Hocquellet et al., "Structure-activity relationship of human liver-expressed antimicrobial peptide 2," Peptides, 2010, 31:58-66.
Holm et al., "Adipogenic and orexigenic effects of the ghrelin-receptor ligand tabimorelin are diminished in leptin-signalling-deficient ZDF rats," Experimental Study, 2004, 150:893-904.
Holubova et al., "Ghrelin Agonist JMV 1843 Increases Food Intake, Body Weight and Expression of Orexigenic Neuropeptides in Mice," Physiol. Res., 2013, 62:435-444.
Howard et al., "Expression and functional analyses of liver expressed antimicrobial peptide-2 (LEAP-2) variant forms in human tissues," Cellular Immunology, 2010, 261:128-133.
Howick et al., "From Belly to Brain: Targeting the Ghrelin Receptor in Appetite and Food Intake Regulation," Int'l. J. Mol. Sci., 2017, 18:273.
Jerlhag et al., "Requirement of Central Ghrelin Signaling for alcohol reward," PNAS, 2009, 106(27):11318-11323.
Joo, "Cyclic Peptides as Therapeutic Agents and Biochemical Tools," Biomolecules and Therapeutics, 2012, 20(1):19-26.
Kojima and Kangawa, "Ghrelin: Structure and Function," Physiol. Rev., 2005, 85:495-522.
Kojima et al., "Ghrelin is a growth-hormone-releasing acylated peptide from stomach," Nature, 1999, 402:656-660.
Krause et al., "Isolation and biochemical characterization of LEAP-2, a novel blood peptide expressed in the liver," 2003, Protein Science, 12:143-152.
Lataillade et al., "Stromal cell-derived factor-1 (SDF-1)/CXCR4 couple plays multiple roles on haematopoietic progenitors at the border between the old cytokine and new chemokine worlds: survival, cell cycling and trafficking," Eur. Cytokine Netw., 2004, 15(3):177-188.
Li et al., "Molecular characterization of the liver-expressed antimicrobial peptide 2 LEAP-2) in a teleost fish, Plecoglossus altivelis:Antimicrobial activity and molecular mechanism," Molecular Immunology, 2015, 65:406-415.
Li et al., "Profound hypoglycemia in starved, ghrelin-deficient mice is caused bv decreased gluconeogenesis and reversed by lactate or fatty' acids," Apr. 2012, Journal of Biological Chemistry, 2012, 287:17942-17950.
Lippl et al., "Low-dose ghrelin infusion—Evidence against a hormonal role in food intake," Regulatory Peptides., 2012, 174:26-31.
McFarlane et al., "Induced Ablation of Ghrelin Cells in Adult Mice Does Not Decrease Food Intake, Body Weight, or Response to High-Fat Diet," Cell Metab., 2014, 20:54-60.
Miras et al., "Mechanisms underly ing weight loss after bariatric surgery," Nature Reviews Gastroenterology & Hepatology, 2013, 10:575-584.
Moulin et al., "Recent Developments in Ghrelin Receptor Ligands," Chem. Med. Chem., 2007, 2:1242-1259.
Nakazato et al., "A role for ghrelin in the central regulation of feeding," Nature, 2001, 409:194-198.
Nass et al., "The role of ghrelin in GH secretion and GH disorders," Molecular and Cellular Endocrinology, 2011, 340(1):10-14.
Navarro et al., "A Significant Role of the Truncated Ghrelin Receptor GHS-R1 bin Ghrelin-induced Signaling in Neurons," The Journal of Biological Chemistry, 2016, 291(25):13048-13062.
Schauer et al., "Bariatric Surgery versus Intensive Medical Therapy in Obese Patients with Diabetes." The New England Journal of Medicine, 2012, 366(17):1567-1576.
Seeley et al., "The Role of Gut Adaptation in the Potent Effects of Multiple Bariatric Surgeries on Obesity and Diabetes," Cell Metabolism, 2015, 21:369-378.
Sun et al., Ghrelin stimulation of growth hormone release and appetite is mediated through the growth hormone secretagogue receptor, PNAS, 2004, 101:4679-4684.
Thomas et al., "Central ghrelin increases food foraging/boarding that is blocked by GHSR antagonism and attenuates hypothalamic paraventricular nucleus neuronal activation," American Journal of Physiology Regulatory Integrative and Comparative Physiology, 2016, 310:275-285.
Wang et al., "RNAscope: A Novel in Situ RNA Analysis Platform for Formalin-Fixed, Paraffin-Embedded Tissues" The Journal of Molecular Diagnostics, 2012, 14:22-29.
Wilson-Perez, et al., "Vertical Sleeve Gastrectomy is Effective in Two Genetic Mouse Models of Glucagon-Like Peptide 1 Receptor Deficiency," Diabetes, 2013, 62:2380-85.
Zhang et al., "Reduced autophagy in livers of fasted, fat-depleted, ghrelin-deficient mice: Reversal by growth hormone," PNAS, 2015, 112:1226-1231.
Zhao et al., "Ghrelin O-acyltransferase (GOAT) is essential for growth hormone-mediated survival of calorie-restricted mice," 2010, PNAS, 107:7467-7472.
Zolotukhiin et al., "Recombinant adeno-asociated virus purification using novel methods improves infectious titer and yield," Jun. 1999, Gene Therapy, 6:973-985.

* cited by examiner

Fig. 2A

| Signal peptide | Propeptide | Mature peptide |

LEAP2

Fig. 2B

Human LEAP2
MWHLKLCAVLMIFLILLLGQIDGS PIPEVSSAKRRPRRMTPFWRGVSLRPIGASCRDDSECITRLCRKRRCSLSVAQE  SEQ ID NO:1

Disulfide Bonds

Mouse LEAP2
MLQLKLFAVLLTCLLLLGQVNSS PVPEVSSAK-RSRRMTPFWRGVSLRPIGASCRDDSECITRLCRKRRCSLSVAQE  SEQ ID NO:16

Fig. 2C

| | | |
|---|---|---|
| Human      | MWHLKLCAVLMIFLILLLGQIDGSPIPEVSSAKRRPRRMTPFWRGVSLRPIGASCRDDSECITRLCRKRRCSLSVAQE | SEQ ID NO:1 |
| Chimpanzee | MWHLKLCAVLMIFLILLLGQIDGSPIPEVSSAKRRPRRMTPFWRGVSLRPIGASCRDDSECITRLCRKRRCSLSVAQE | SEQ ID NO:11 |
| Rhesus     | MWHLKLCAVLMIFLLLLLGQTDGSPIPEVSSAKRRPRRMTPFWRGVSLRPIGASCRDDSECITRLCRKRRCSLSVAQE | SEQ ID NO:12 |
| Cynomolgus | MWHLKLCAVLMIFLILLLGQTDGSPIPEVSSAKRRPRRMTPFWRGVSLRPIGASCRDDSECITRLCRKRRCSLSVAQE | SEQ ID NO:13 |
| Guinea pig |          SVVLLICLLLLGQVDGSPVPEEKSSVKKRLRRMTPFWRAVSLRPIGASCRDDSECITRLCRKRRCSLSVAQE | SEQ ID NO:14 |
| Bovine     | MWHLKLFAVLMICLLLLLAQVDGSPIPQQSSAKRRPRRMTPFWRGVSLRPIGASCRDDSECITRLCRKRRCSLSVAQE | SEQ ID NO:15 |
| Mouse      | MLQIKLFAVLLTCLILLLGQVNSSPVPEVSSAK RSRRMTPFWRGVSLRPIGASCRDDSECITRLCRKRRCSLSVAQE | SEQ ID NO:16 |
| Rabbit     | MWHLKLFAVLMICLLLLLGQVDGSPVPELSSAKRRPRRMTPFWRGVSLRPIGASCRDNAECVTRLCRKRRCSLSVAQE | SEQ ID NO:17 |
| Rat        |    LQLKLFAVLLTCLILLLGQAQSSPVPELSSAK RTRRMTPFWRGVSLRPIGASCRDNSECITMLCRKNRCFLRTASE | SEQ ID NO:18 |
| Chicken    | MHCLKIMAFLLFFSLLLSQVCCASLHQP QPLLRLKRMTPFWRGVSLRPVGASCRDNSECITMLCRKNRCFLRTASE | SEQ ID NO:19 |

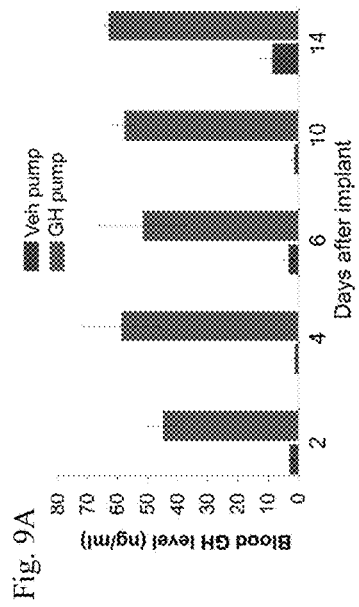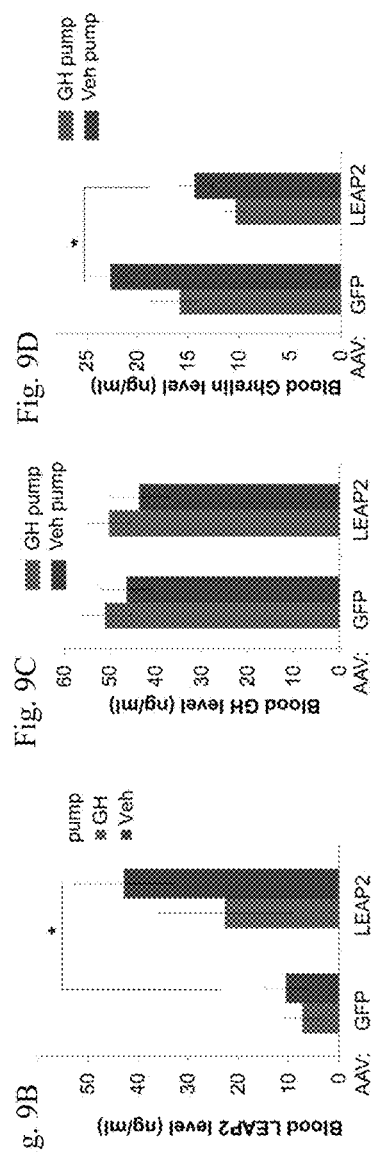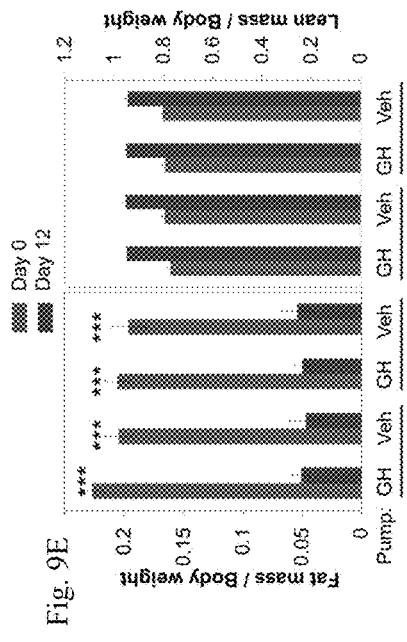

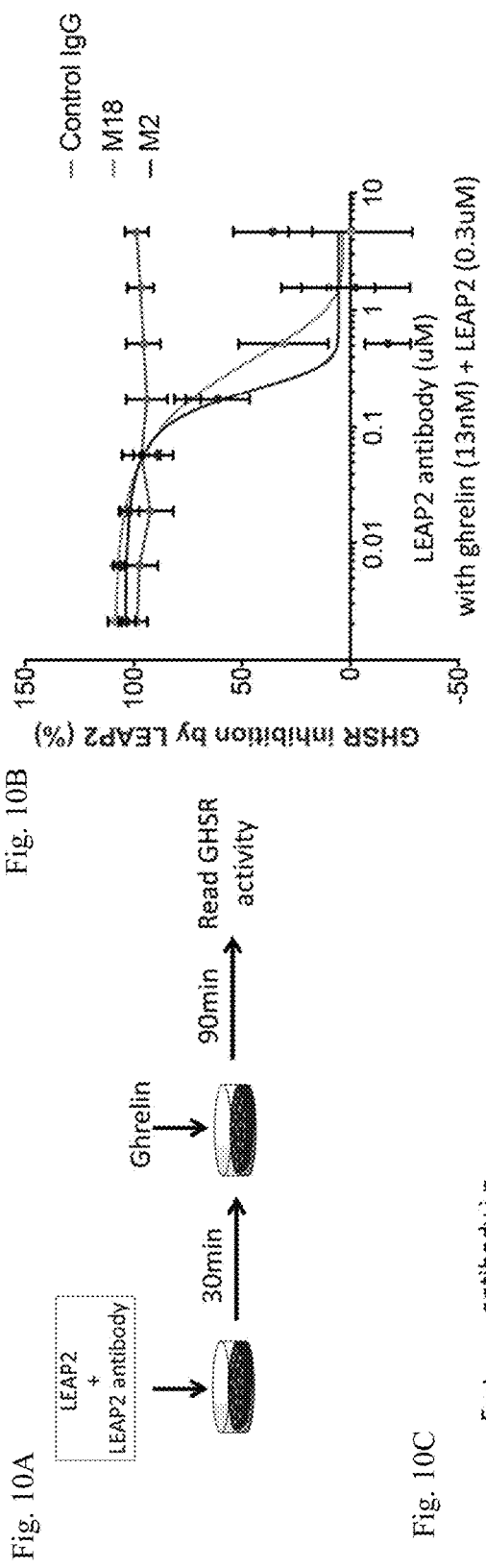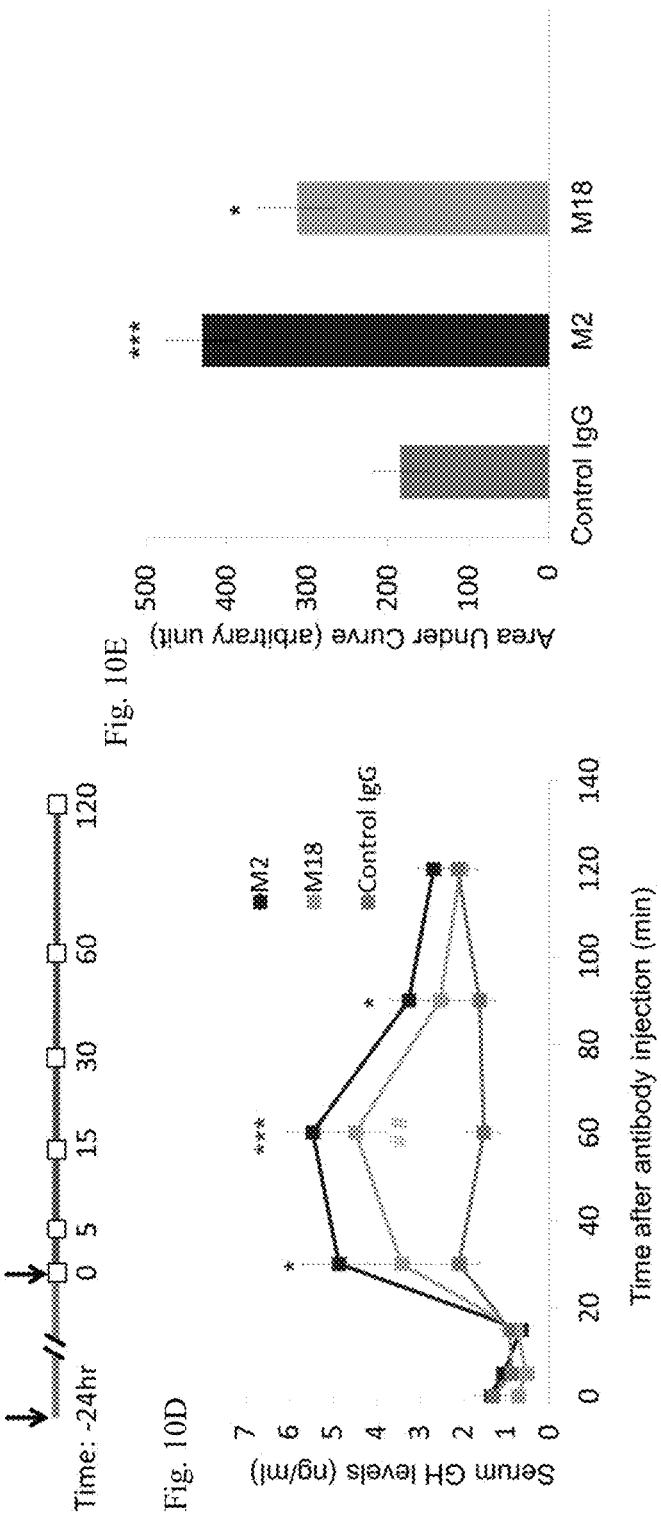

Figure 11A

Heavy chain variable regions

```
Kabat     1         10        22         31----35        40              50--a-----60---65
AbM       1         10        22   26----35               40              50--a-----58
Chothia   1         10        22   26----32               40                   a-55    65
Contact   1         10        22         30----35        40        47----a-----58      65
IMGT      1         10        23         27----38  41                    56-----65      74
AHon      1                   23                27        42                    57              76

M1/2  EVQLQQSGTVLARPGASVKMSCKAS GYTFTSYWMH WVKQRPGQGLEWIG AIYPGNSDTSYKQKFKG
       M18   EIQLQQSGPELMKPGASVKISCKAS GYSFTNYYIH WVKQSHGKSLEWIG YIDPFNGGTNYNQKFKG

Kabat    70        80   abc    90         95---------102        110
AbM      70        80   abc    90         95---------102        110
Chothia  70        80   abc    90         96---------101        110
Contact  70        80   abc    90    93---------101             110
IMGT               89          105----------117
AHon     75                         109                138

M1/2  KAKLTAVTSASTVYMELSSLTDEDSAVYYCTY GKEEYLFAMDY WGQGTSVTVSS   SEQ ID NO:7
       M18   KATLTVDKSSSTAYMHLSSLTFEEDSAVYYCAR RGYYY--GFTY WGQGTLVTVSA  SEQ ID NO:9
```

METHODS OF TREATING A WASTING SYNDROME, INCREASING GROWTH HORMONE LEVELS, AND INCREASING GHSR ACTIVITY WITH A LEAP2 ANTIBODY

CROSS-REFERENCE TO RELATED APPLICATIONS

This application is a continuation of U.S. application Ser. No. 15/987,766, filed May 23, 2018, issued as U.S. Pat. No. 10,781,253, which claims the priority benefit of U.S. Provisional Application No. 62/510,668, filed May 24, 2017, the contents of both of which are hereby incorporated by reference herein in their entirety.

SEQUENCE LISTING

The instant application contains a Sequence Listing which has been submitted electronically in ASCII format and is hereby incorporated by reference in its entirety. Said ASCII copy, created on Aug. 13, 2020, is named 47702-0023002_SEQ.txt, and is 62 KB in size.

FIELD OF THE INVENTION

The present invention generally relates to binding agents, such as peptides or antibodies, that affect growth hormone secretagogue receptor (GHSR) activity, as well as methods of using the binding agents for the treatment and/or prevention of diseases.

BACKGROUND

Ghrelin, a peptide hormone, was originally discovered as an endogenous growth hormone (GH) secretagogue with potential utility in the treatment of growth hormone deficiency (Kojima, et al., 1999, *Nature*, 402:656-660). Ghrelin is produced by the stomach and is involved in gut-brain signaling, potently stimulating the release of growth hormone from the anterior pituitary. Ghrelin is multifunctional and plays a role in maintaining energy homeostasis, gastric acid release, gastric motility, stimulation of food intake, appetite and weight gain, reward-seeking behaviors and addiction, and suppression of insulin secretion (Kojima and Kangawa, 2005, *Physiol. Rev.*, 85:495-522; Nakazato, et al., 2001, *Nature*, 409:194-198).

Growth hormone secretagogue receptor (also known as GHSR, GHS-R, GH-releasing peptide receptor, and ghrelin receptor) is a G protein-coupled receptor (GPCR) expressed in many tissues throughout the body, including the pituitary gland, hypothalamus, hippocampus, gastrointestinal tract, and the vasculature including the aorta, coronary arteries, pulmonary arteries, arcuate arteries, and saphenous veins (Cruz and Smith, 2008, *Vitam. Horm.*, 77:47-88). GHSR has at least two isoforms: GHSR isoform 1a (GHSR1a) and GHSR isoform 1b (GHSR1b). GHSR1b is believed to be a truncated, non-signaling ghrelin receptor that may influence ghrelin-induced GHSR1a-mediated signaling and/or influence the ability of GHSR1a to form oligomeric complexes with other receptors (Navarro, et al., 2016, *JBC*, 291:13048-13062).

GHSR is constitutively active in the absence of an agonist, providing a basal level of signaling required for the development of normal height. In addition, ghrelin and GHSR not only stimulate growth hormone release, but also appear to play a role in several aspects of energy homeostasis. Inverse agonists of GHSR are of interest for the treatment of obesity, and the ghrelinergic system has received considerable attention as a therapeutic target to reduce appetite in obesity as well as to stimulate food intake and feed efficiency in the treatment of wasting syndromes, anorexia, malnutrition, and cachexia (Howick, et al., 2017, *Int'l. J. Mol. Sci.*, 18:273).

Several academic laboratories and pharmaceutical companies have developed synthetic molecules with agonist, partial agonist, antagonist, or inverse agonist properties toward GHSR for clinical and therapeutic applications in gastroenterology, oncology, and cardiology. For example, some GHSR agonists have appetite-stimulating and growth hormone-releasing effects, and are expected to be useful for the treatment of muscle wasting and frailty associated with old-age and degenerative diseases. On the other hand, GHSR antagonists have anorectic effects and are likely to be useful for the treatment of obesity (Moulin, et al., 2007, *Chem. Med. Chem.*, 2:1242-1259; Holubova, et al., 2013, *Physiol. Res.*, 62:435-444; Chollet, et al., 2009, 1 *Pept. Sci.*, 15:711-730) or disorders of excessive growth hormone secretion (Nass, et al., 2011, *Mol. Cell. Endocrinol.*, 340:10-14).

At least in part because supraphysiological levels of ghrelin are needed to induce food intake (Lippl, et al., 2012, *Regul. Pept.*, 174:26-31), it has been suggested that the true physiological role of ghrelin may be to maintain viable blood glucose levels during chronic calorie restriction (Li, et al., 2012, *J. Biol. Chem.*, 287:17942-17950; Zhang, et al., 2015, PNAS, 112:1226-1231; Zhao, et al., 2010, *PNAS*, 107:7467-7472). Under calorie-restricted conditions, maintaining blood glucose concentrations sufficient to support brain function is critical for survival (Cahill, 2006, *Annu. Rev. Nutr.*, 26:1-22). Ghrelin is secreted in response to caloric restriction and stimulates growth hormone release, which promotes gluconeogenesis and maintains viable glucose levels (Li, et al., 2012, *JBC*, 287:17942-17950; Zhang, et al., 2015, *PNAS*, 112:1226-1231).

Although regulation of ghrelin production has been well studied, regulation of the interaction of ghrelin with GHSR has not been described. Furthermore, to date, the existence of an endogenous antagonist of GHSR has not been described. Such an antagonist could have favorable characteristics in some clinical settings.

BRIEF SUMMARY OF THE INVENTION

The present disclosure provides binding agents that affect GHSR activity. The binding agents include, but are not limited to, agents that bind GHSR (e.g., LEAP2 and variants thereof) and agents that bind LEAP2 (e.g., anti-LEAP2 antibodies) and methods of their use. LEAP2 (liver-expressed antimicrobial peptide 2) is described herein as an endogenous antagonist of GHSR. Also presented herein is evidence that LEAP2 is a potent inhibitor of ghrelin and/or ghrelin-induced GHSR activity, both in vitro and in vivo, revealing a hitherto unknown mechanism for regulating ghrelin activity.

In one aspect, the present disclosure provides agents that bind GHSR. In some embodiments, the binding agent comprises LEAP2. In some embodiments, the binding agent comprises a LEAP2 variant. In some embodiments, the binding agent is an antagonist of GHSR. In some embodiments, the binding agent is an antagonist of GHSR, wherein the binding agent comprises SEQ ID NO:2. In some embodiments, the binding agent comprises human LEAP2. In some embodiments, the binding agent comprises SEQ ID NO:2. In some embodiments, LEAP2 consists of SEQ ID NO:2. In some embodiments, LEAP2 or a variant thereof is linked or fused to a heterologous polypeptide. In some embodiments, LEAP2 or a variant thereof is not fused to a heterologous polypeptide. In some embodiments, a LEAP2 variant is not a peptide consisting of the amino acid sequence GVSLRPI-GASCR (SEQ ID NO:3) or GVSLRPIGASCRDDSECITR (SEQ ID NO:4).

In some embodiments, a binding agent (e.g., LEAP2 or a variant thereof) inhibits and/or reduces GHSR activity. In some embodiments, the GHSR activity is mediated and/or induced by ghrelin. In some embodiments, a binding agent (e.g., LEAP2 or a variant thereof) inhibits and/or reduces food intake. In some embodiments, the binding agent (e.g., LEAP2 or a variant thereof) suppresses appetite. In some embodiments, a binding agent (e.g., LEAP2 or a variant thereof) reduces or lowers blood glucose levels. In some embodiments, a binding agent (e.g., LEAP2 or a variant thereof) reduces or lowers growth hormone levels.

In another aspect, the present disclosure provides agents that bind LEAP2. These agents may be referred to herein as "LEAP2-binding agents". In some embodiments, a binding agent that specifically binds LEAP2 comprises a heavy chain CDR1, CDR2, and CDR3 from Table 1 and a light chain CDR1, CDR2, and CDR3 from Table 1. In some embodiments, a binding agent that specifically binds LEAP2 comprises a heavy chain CDR1, CDR2, and CDR3 from Table 2 and a light chain CDR1, CDR2, and CDR3 from Table 2. In some embodiments, a binding agent that specifically binds LEAP2 comprises: (a) a heavy chain CDR1 comprising GYTFTSYWMH (SEQ ID NO:20), a heavy chain CDR2 comprising AIYPGNSDTSYKQKFKG (SEQ ID NO:21), and a heavy chain CDR3 comprising GKEEY-LFAMDY (SEQ ID NO:22); and/or a light chain CDR1 comprising KSSQSLLYSSNQKNYLA (SEQ ID NO:23), a light chain CDR2 comprising WASTRES (SEQ ID NO:24), and a light chain CDR3 comprising QQYYSYPT (SEQ ID NO:25); or (b) a heavy chain CDR1 comprising GYSFTNYYIH (SEQ ID NO:26), a heavy chain CDR2 comprising YIDPFNGGTNYNQKFKG (SEQ ID NO:27), and a heavy chain CDR3 comprising RGYYYGFTY (SEQ ID NO:28); and/or a light chain CDR1 comprising KASQSVDYDGDSYMN (SEQ ID NO:29), a light chain CDR2 comprising TASNLES (SEQ ID NO:30), and a light chain CDR3 comprising QQSNEDPYT (SEQ ID NO:31). In some embodiments, the binding agent comprises a heavy chain CDR1 comprising GYTFTSYWMH (SEQ ID NO:20), a heavy chain CDR2 comprising AIYPGNSDT-SYKQKFKG (SEQ ID NO:21), and a heavy chain CDR3 comprising GKEEYLFAMDY (SEQ ID NO:22); and/or a light chain CDR1 comprising KSSQSLLYSSNQKNYLA (SEQ ID NO:23), a light chain CDR2 comprising WAST-RES (SEQ ID NO:24), and a light chain CDR3 comprising QQYYSYPT (SEQ ID NO:25). In some embodiments, the binding agent comprises a heavy chain CDR1 comprising GYSFTNYYIH (SEQ ID NO:26), a heavy chain CDR2 comprising YIDPFNGGTNYNQKFKG (SEQ ID NO:27), and a heavy chain CDR3 comprising RGYYYGFTY (SEQ ID NO:28); and/or a light chain CDR1 comprising KASQSVDYDGDSYMN (SEQ ID NO:29), a light chain CDR2 comprising TASNLES (SEQ ID NO:30), and a light chain CDR3 comprising QQSNEDPYT (SEQ ID NO:31). In some embodiments, the binding agent is an antibody.

In some embodiments, a binding agent (e.g., an antibody) that specifically binds LEAP2 comprises (a) a heavy chain framework region (FR) 1, a heavy chain FR2, a heavy chain FR3, and a heavy chain FR4; and/or (b) a light chain FR1, a light chain FR2, a light chain FR3, and a light chain FR4. In some embodiments, a binding agent (e.g., an antibody) comprises a heavy chain FR1, a heavy chain FR2, a heavy chain FR3, and a heavy chain FR4. In some embodiments, a binding agent comprises a light chain FR1, a light chain FR2, a light chain FR3, and a light chain FR4. In some embodiments, a binding agent (e.g., an antibody) comprises (a) a heavy chain FR1, a heavy chain FR2, a heavy chain FR3, and a heavy chain FR4; and (b) a light chain FR1, a light chain FR2, a light chain FR3, and a light chain FR4.

In some embodiments, a binding agent (e.g., an antibody) that specifically binds LEAP2 comprises: (a) a heavy chain variable region having at least 80% sequence identity to SEQ ID NO:7; and/or (b) a light chain variable region having at least 80% sequence identity to SEQ ID NO:8. In some embodiments, a binding agent (e.g., an antibody) that specifically binds LEAP2 comprises: (a) a heavy chain variable region having at least 90% sequence identity to SEQ ID NO:7; and/or (b) a light chain variable region having at least 90% sequence identity to SEQ ID NO:8. In some embodiments, a binding agent (e.g., an antibody) that specifically binds LEAP2 comprises a heavy chain variable region having at least 95% sequence identity to SEQ ID NO:7 and a light chain variable region having at least 95% sequence identity to SEQ ID NO:8. In some embodiments, a binding agent (e.g., an antibody) that specifically binds LEAP2 comprises a heavy chain variable region comprising SEQ ID NO:7 and a light chain variable region comprising SEQ ID NO:8.

In some embodiments, a binding agent (e.g., an antibody) that specifically binds LEAP2 comprises the heavy chain CDR1, CDR2, and CDR3, and/or the light chain CDR1, CDR2, and CDR3 from the antibody designated M1/M2 that comprises a heavy chain variable region comprising SEQ ID NO:7 and a light chain variable region comprising SEQ ID NO:8. In some embodiments, a binding agent (e.g., an antibody) that specifically binds LEAP2 comprises the heavy chain CDR1, CDR2, and CDR3, and the light chain CDR1, CDR2, and CDR3 from the antibody designated M1/M2 that comprises a heavy chain variable region comprising SEQ ID NO:7 and a light chain variable region comprising SEQ ID NO:8.

In some embodiments, a binding agent (e.g., an antibody) that specifically binds LEAP2 comprises: (a) a heavy chain variable region having at least 80% sequence identity to SEQ ID NO:9; and/or (b) a light chain variable region having at least 80% sequence identity to SEQ ID NO:10. In some embodiments, a binding agent (e.g., an antibody) that specifically binds LEAP2 comprises: (a) a heavy chain variable region having at least 90% sequence identity to SEQ ID NO:9; and/or (b) a light chain variable region having at least 90% sequence identity to SEQ ID NO:10. In some embodiments, a binding agent (e.g., an antibody) that specifically binds LEAP2 comprises a heavy chain variable region having at least 95% sequence identity to SEQ ID NO:9 and a light chain variable region having at least 95% sequence identity to SEQ ID NO:10. In some embodiments, a binding agent (e.g., an antibody) that specifically binds LEAP2 comprises a heavy chain variable region comprising SEQ ID NO:9 and a light chain variable region comprising SEQ ID NO:10.

In some embodiments, a binding agent (e.g., an antibody) that specifically binds LEAP2 comprises the heavy chain CDR1, CDR2, and CDR3, and/or the light chain CDR1, CDR2, and CDR3 from the antibody designated M18 that comprises a heavy chain variable region comprising SEQ ID NO:9 and a light chain variable region comprising SEQ ID NO:10. In some embodiments, a binding agent (e.g., an antibody) that specifically binds LEAP2 comprises the heavy chain CDR1, CDR2, and CDR3, and the light chain CDR1, CDR2, and CDR3 from the antibody designated M18 that comprises a heavy chain variable region comprising SEQ ID NO:9 and a light chain variable region comprising SEQ ID NO:10.

In some embodiments, an agent binds LEAP2, a LEAP2 fragment, and/or a LEAP2 epitope. In some embodiments, the binding agent is a LEAP2 antagonist. In some embodiments, the binding agent inhibits binding of LEAP2 to GHSR. In some embodiments, the binding agent is a GHSR agonist. In some embodiments, the binding agent (e.g., an anti-LEAP2 antibody) increases, enhances, and/or promotes GHSR activity. In some embodiments, the GHSR activity is mediated or induced by ghrelin. In some embodiments, the binding agent (e.g., an anti-LEAP2 antibody) increases and/or promotes food intake. In some embodiments, the binding agent (e.g., an anti-LEAP2 antibody) enhances or increases growth hormone levels.

In another aspect of the disclosure, provided herein is a binding agent that competes for binding to LEAP2 with any of the LEAP2-binding agents described herein. In some embodiments, a binding agent (e.g., an antibody) competes for binding to LEAP2 with a reference antibody, wherein the reference antibody comprises (a) a heavy chain variable region comprising SEQ ID NO:7 and a light chain variable region comprising SEQ ID NO:8 or (b) a heavy chain variable region comprising SEQ ID NO:9 and a light chain variable region comprising SEQ ID NO:10.

In some embodiments, a LEAP2-binding agent binds the same epitope on LEAP2 as an antibody described herein. In some embodiments, a LEAP2-binding agent binds an epitope on LEAP2 that overlaps with the epitope on LEAP2 bound by an antibody described herein. In some embodiments, a LEAP2-binding agent binds the same epitope as an antibody comprising the heavy chain CDR1, CDR2, and CDR3 and the light chain CDR1, CDR2, and CDR3 of antibody M1/M2. In some embodiments, a LEAP2-binding agent binds the same epitope as an antibody comprising the heavy chain CDR1, CDR2, and CDR3 and the light chain CDR1, CDR2, and CDR3 of antibody M18. In some embodiments, a LEAP2-binding agent binds an epitope that overlaps with the epitope bound by an antibody comprising the heavy chain CDR1, CDR2, and CDR3 and the light chain CDR1, CDR2, and CDR3 of antibody M1/M2. In some embodiments, a LEAP2-binding agent binds an epitope that overlaps with the epitope bound by an antibody comprising the heavy chain CDR1, CDR2, and CDR3 and the light chain CDR1, CDR2, and CDR3 of antibody M18.

In some embodiments of each of the aforementioned aspects and embodiments, as well as other aspects and embodiments described herein, a LEAP2-binding agent is an antibody. In some embodiments, the antibody is a monoclonal antibody. In some embodiments, the antibody is a humanized antibody. In some embodiments, the antibody is a human antibody. In some embodiments, the antibody is a chimeric antibody. In some embodiments, the antibody is an IgG antibody. In some embodiments, the antibody is an IgG1 antibody, an IgG2 antibody, an IgG3 antibody, or an IgG4 antibody. In some embodiments, the antibody is a bispecific antibody or a multispecific antibody. In some embodiments, the antibody is an antibody fragment. In some embodiments, the antibody or antibody fragment is a Fab, Fab', F(ab')$_2$, Fv, scFv, (scFv)$_2$, single chain antibody, dual variable region antibody, single variable region antibody, linear antibody, or a V region antibody. In some embodiments, the antibody is a scFv antibody. In some embodiments, the antibody is a disulfide-linked scFv (dsscFv).

In another aspect, the disclosure provides compositions comprising a binding agent (e.g., LEAP2 or a variant thereof or an anti-LEAP2 antibody) described herein.

In another aspect, the disclosure provides pharmaceutical compositions comprising a binding agent (e.g., LEAP2 or a variant thereof or an anti-LEAP2 antibody) described herein and a pharmaceutically acceptable carrier.

In some embodiments of each of the aforementioned aspects, as well as other aspects and/or embodiments described elsewhere herein, a binding agent (e.g., LEAP2 or a variant thereof or an anti-LEAP2 antibody) is isolated. In some embodiments, a binding agent (e.g., LEAP2 or a variant thereof or an anti-LEAP2 antibody) is substantially pure.

In another aspect, the disclosure provides polynucleotides comprising a polynucleotide that encodes a binding agent (e.g., LEAP2 or a variant thereof or an anti-LEAP2 antibody) described herein. In some embodiments, the polynucleotide is isolated. In some embodiments, a vector comprises a polynucleotide that encodes a binding agent (e.g., LEAP2 or a variant thereof or an anti-LEAP2 antibody) described herein. In some embodiments, an isolated cell comprises a polynucleotide that encodes a binding agent (e.g., LEAP2 or a variant thereof or an anti-LEAP2 antibody) described herein. In some embodiments, an isolated cell comprises a vector comprising a polynucleotide that encodes a binding agent (e.g., LEAP2 or a variant thereof or an anti-LEAP2 antibody) described herein. In some embodiments, the disclosure provides a cell comprising a binding agent (e.g., LEAP2 or a variant thereof or an anti-LEAP2 antibody) described herein. In some embodiments, the disclosure provides a cell producing a binding agent (e.g., LEAP2 or a variant thereof or an anti-LEAP2 antibody) described herein. In some embodiments, a cell produces an anti-LEAP2 antibody described herein. In some embodiments, a cell is a monoclonal cell line. In some embodiments, a cell is a hybridoma.

In another aspect, the disclosure provides methods of using a binding agent (e.g., LEAP2 or a variant thereof or an anti-LEAP2 antibody) described herein. In some embodiments, a method comprises using a composition comprising a binding agent (e.g., LEAP2 or a variant thereof or an anti-LEAP2 antibody) described herein. In some embodiments, a method comprises using a pharmaceutical composition comprising a binding agent (e.g., LEAP2 or a variant thereof or an anti-LEAP2 antibody) described herein.

In some embodiments, a method of inhibiting or reducing ghrelin activity in a subject comprises administering to the subject a therapeutically effective amount of LEAP2 or a variant thereof. In some embodiments, a method of inhibiting, reducing, or blocking GHSR activity in a subject comprises administering to the subject a therapeutically effective amount of LEAP2 or a variant thereof. In some embodiments, the GHSR activity is mediated or induced by ghrelin. In some embodiments, a method of inhibiting, reducing, or blocking ghrelin-induced growth hormone release in a subject comprises administering to the subject a therapeutically effective amount of LEAP2 or a variant thereof. In some embodiments, a method of suppressing appetite and/or reducing food intake in a subject comprises administering to the subject a therapeutically effective amount of LEAP2 or a variant thereof.

In some embodiments, a method of treating a neuroendocrine and/or metabolic disease such as obesity, diabetes, acromegaly, gigantism, or Prader-Willi syndrome in a subject comprises administering to the subject a therapeutically effective amount of LEAP2 or a variant thereof. In some embodiments, a method of treating obesity in a subject comprises administering to the subject a therapeutically effective amount of LEAP2 or a variant thereof. In some embodiments, a method of treating diabetes in a subject comprises administering to the subject a therapeutically effective amount of LEAP2 or a variant thereof. In some embodiments, the diabetes is Type 1 diabetes. In some embodiments, the diabetes is Type 2 diabetes. In some embodiments, a method of treating hyperglycemia in a subject comprises administering to the subject a therapeutically effective amount of LEAP2 or a variant thereof. In some embodiments, a method of reducing or lowering blood glucose levels in a subject comprises administering to the subject a therapeutically effective amount of LEAP2 or a variant thereof. In some embodiments, a method of reducing or lowering growth hormone levels in a subject comprises administering to the subject a therapeutically effective amount of LEAP2 or a variant thereof.

In some embodiments, a method comprising administering LEAP2 or a variant thereof described herein further comprises administering at least one additional therapeutic agent to the subject. In some embodiments, the at least one additional therapeutic agent is a diabetes or hyperglycemia drug. In some embodiments, the diabetes or hyperglycemia drug is a biguanide, a sulfonylurea, a meglitinide derivative, an alpha-glucosidase inhibitor, a thiazolidinedione (TZDs), a glucagon-like peptide-1 (GLP-1) agonist, a dipeptidyl peptidase 4 (DPP-4) inhibitor, a selective sodium-glucose transporter-2 (SGLT-2) inhibitor, an insulin or insulin mimetic, an amylinomimetic, a bile acid sequestrant, and/or a dopamine agonist. In some embodiments, the at least one additional therapeutic agent is an obesity drug, an appetite suppressant, and/or a weight loss drug.

In some embodiments, a method of increasing, enhancing, and/or promoting ghrelin activity in a subject comprises administering to the subject a therapeutically effective amount of a LEAP2-binding agent (e.g., an anti-LEAP2 antibody). In some embodiments, a method of increasing, enhancing, and/or promoting GHSR activity in a subject comprises administering to the subject a therapeutically effective amount of a LEAP2-binding agent (e.g., an anti-LEAP2 antibody). In some embodiments, the GHSR activity is mediated by ghrelin. In some embodiments, a method of increasing, enhancing, and/or promoting ghrelin-induced growth hormone release in a subject comprises administering to the subject a therapeutically effective amount of a LEAP2-binding agent (e.g., an anti-LEAP2 antibody). In some embodiments, a method of stimulating appetite and/or increasing food intake in a subject comprises administering to the subject a therapeutically effective amount of a LEAP2-binding agent (e.g., an anti-LEAP2 antibody). In some embodiments, a method of weight gain in a subject comprises administering to the subject a therapeutically effective amount of a LEAP2-binding agent (e.g., an anti-LEAP2 antibody). In some embodiments, a method of treating a neuroendocrine and/or metabolic disease such as anorexia, cachexia, or other wasting syndromes in a subject comprises administering to the subject a therapeutically effective amount of a LEAP2-binding agent (e.g., an anti-LEAP2 antibody). In some embodiments, a method of treating cachexia in a subject comprises administering to the subject a therapeutically effective amount of a LEAP2-binding agent (e.g., an anti-LEAP2 antibody). In some embodiments, the cachexia is cancer cachexia. In some embodiments, a method of treating anorexia in a subject comprises administering to the subject a therapeutically effective amount of a LEAP2-binding agent (e.g., an anti-LEAP2 antibody). In some embodiments, a method of stabilizing blood glucose levels in a subject under fasting or restricted calorie conditions comprises administering to the subject a therapeutically effective amount of a LEAP2-binding agent (e.g., an anti-LEAP2 antibody). In some embodiments, a method of inducing or increasing growth hormone levels in a subject comprises administering to the subject a therapeutically effective amount of a LEAP2-binding agent (e.g., an anti-LEAP2 antibody).

In some embodiments, a method comprising administering a LEAP2-binding agent (e.g., an anti-LEAP2 antibody) further comprises administering at least one additional therapeutic agent to the subject. In some embodiments, the at least one additional therapeutic agent is a progestogen or a corticosteroid.

In some embodiments of each of the aforementioned aspects and embodiments, as well as other aspects and embodiments described herein, the subject is human.

Where aspects or embodiments of the disclosure are described in terms of a Markush group or other grouping of alternatives, the present disclosure encompasses not only the entire group listed as a whole, but also each member of the group individually and all possible subgroups of the main group, and also the main group absent one or more of the group members. The present disclosure also envisages the explicit exclusion of one or more of any of the group members in the claimed disclosure.

BRIEF DESCRIPTION OF THE FIGURES

FIGS. 2A-2C. FIG. 2A. Representative drawing of the protein structure of full length LEAP2. FIG. 2B. Amino acid sequences of full length human LEAP2 and murine LEAP2. Positioning of disulfide bonds depicted on human LEAP2 sequence. FIG. 2C. An amino acid sequence alignment of LEAP2 peptides from various species.

FIG. 6A. Food intake after ghrelin injection in mice. FIG. 6B. Food intake after ghrelin injection in the absence or presence of LEAP2.

FIG. 8A. A diagram of the experimental design for growth hormone infusion during chronic calorie restriction. FIG. 8B. Blood glucose levels in mice expressing LEAP2 or GFP and with or without growth hormone infusion. FIG. 8C. A Kaplan-Meier survival curve of mice in study.

FIGS. 9A-9E. FIG. 9A. Growth hormone level in mice with or without a growth hormone infusion. FIG. 9B. LEAP2 levels in blood in mice expressing LEAP2 or GFP and with or without growth hormone infusion. 9C. Growth hormone levels in blood in mice expressing LEAP2 or GFP and with or without growth hormone infusion. FIG. 9D.

Ghrelin levels in blood in mice expressing LEAP2 or GFP and with or without growth hormone infusion. FIG. 9E. Fat mass/body weight or lean mass/bodyweight ratios in mice with or without growth hormone infusion.

FIGS. 10A-10E. FIG. 10A. A diagram of the experimental design for anti-LEAP2 antibody screening. FIG. 10B. A dose-response curve evaluating the effect of anti-LEAP2 antibodies on GHSR activity in the presence of LEAP2 peptide. FIG. 10C. A diagram of the experimental design for evaluating the effect of anti-LEAP2 antibodies on growth hormone release after fasting. FIG. 10D. Growth hormone levels after fasting and treatment with anti-LEAP2 antibodies. FIG. 10E. Growth hormone levels after fasting and treatment with anti-LEAP2 antibodies shown as AUC.

FIGS. 11A and 11B. FIG. 11A. An alignment of the heavy chain variable region amino acid sequences of exemplary anti-LEAP2 antibodies M1/M2 and M18. FIG. 11B. An alignment of the light chain variable region amino acid sequences of exemplary anti-LEAP2 antibodies M1/M2 and M18.

DETAILED DESCRIPTION OF THE INVENTION

Figure 1:
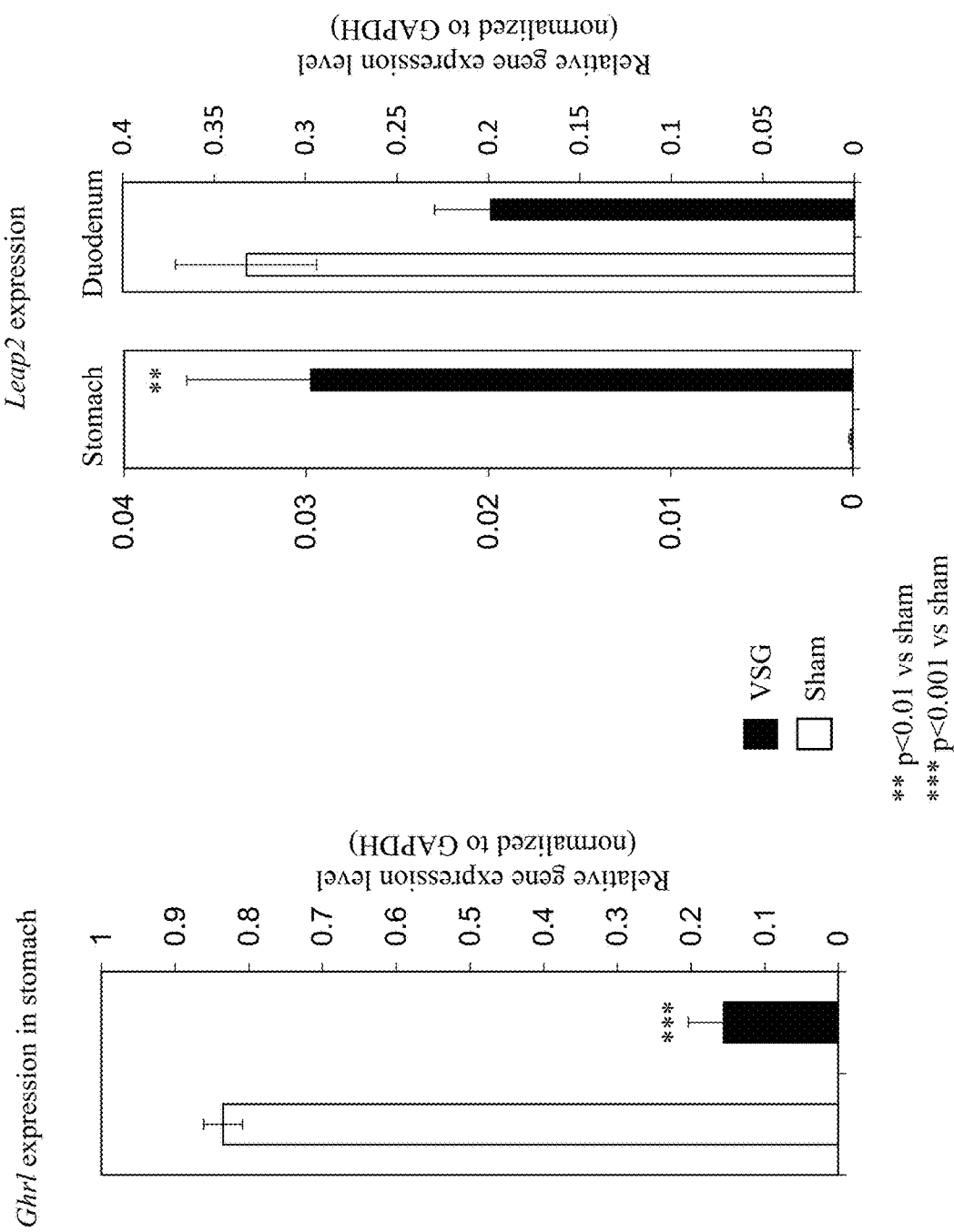
FIG. 1. Expression level of ghrelin mRNA in the stomach after vertical sleeve gastrectomy (VSG) surgery or sham surgery in mice. Expression level of LEAP2 mRNA in the stomach and duodenum after vertical sleeve gastrectomy (VSG) surgery or sham surgery in mice.

LEAP2 (liver-expressed antimicrobial peptide 2) was originally identified in human blood samples and was shown to exhibit antimicrobial activity in vitro (Krause, et al., 2003, *Protein Sci.*, 12:143-152). LEAP2 is expressed in the liver and small intestine, but is nearly undetectable in the stomach under physiological conditions. The inventors have shown that LEAP2 expression dramatically increases after vertical sleeve gastrectomy (VSG) surgery. Surprisingly, the inventors discovered that LEAP2 is an endogenous antagonist of GHSR. These results support a hypothesis that an increase of LEAP2 may contribute to suppression of appetite after VSG surgery. Thus, LEAP2 is a new addition to the list of hormones that connect the gut, brain, and metabolic control. As a newly identified part of the ghrelin/GHSR pathway, LEAP2 represents a potential novel target for therapeutic intervention.

As demonstrated herein, LEAP2 inhibited ghrelin-induced GHSR activity and antagonized the effects of ghrelin in vivo. The effects of LEAP2 include, but may not be limited to, suppressing appetite, decreasing food intake, and decreasing growth hormone release. In addition, it was shown that secretion of LEAP2 was suppressed by fasting. In contrast, anti-LEAP2 antibodies enhanced the effects of ghrelin-induced GHSR activity in vivo.

I. Definitions

Unless otherwise defined herein, technical and scientific terms used in the present disclosure have the meanings that are commonly understood by those of ordinary skill in the art. For purposes of interpreting this specification, the following description of terms will apply and whenever appropriate, terms used in the singular will also include the plural and vice versa. In the event that any description of a term set forth conflicts with any document incorporated herein by reference, the description of the term set forth below shall control.

The term "binding agent" as used herein refers to a molecule that binds a specific antigen or target (e.g., LEAP2 or GHSR). A binding agent may comprise a protein, polypeptide, peptide, nucleic acid, carbohydrate, lipid, or small molecular weight compound. In some embodiments, a binding agent comprises a binding agent. In some embodiments, a binding agent is a binding agent. In some embodiments, a binding agent is a peptide. In some embodiments, a binding agent comprises an antibody or an antigen-binding fragment thereof. In some embodiments, a binding agent is an antibody or an antigen-binding fragment thereof. In some embodiments, a binding agent comprises an alternative protein scaffold or artificial scaffold and an antigen-binding site comprising CDRs or CDR derivatives. In some embodiments, a binding agent is a fusion protein comprising an antigen-binding site. In some embodiments, a binding agent is a bispecific or multispecific molecule comprising at least one antigen-binding site.

The terms "agonist" and "agonistic" as used herein refer to or describe an agent that is capable of, directly or indirectly, substantially inducing, activating, promoting, increasing, or enhancing the biological activity of a target and/or a pathway. The term "agonist" is used herein to include any agent that partially or fully induces, activates, promotes, increases, or enhances the activity of a protein.

The terms "antagonist" and "antagonistic" as used herein refer to or describe an agent that is capable of, directly or indirectly, partially or fully blocking, inhibiting, reducing, or neutralizing a biological activity of a target and/or pathway. The term "antagonist" is used herein to include any agent that partially or fully blocks, inhibits, reduces, or neutralizes the activity of a protein.

The terms "modulation" and "modulate" as used herein refer to a change or an alteration in a biological activity. Modulation includes, but is not limited to, stimulating an activity or inhibiting an activity. Modulation may be an increase or a decrease in activity, a change in binding characteristics, or any other change in the biological, functional, or immunological properties associated with the activity of a protein, a pathway, a system, or other biological targets of interest.

The term "antibody" as used herein refers to an immunoglobulin molecule that recognizes and binds a target through at least one antigen-binding site. "Antibody" is used herein in the broadest sense and encompasses various antibody structures, including but not limited to, polyclonal antibodies, recombinant antibodies, monoclonal antibodies, chimeric antibodies, humanized antibodies, human antibodies, bispecific antibodies, multispecific antibodies, diabodies, tribodies, tetrabodies, single chain Fv (scFv) antibodies, single domain antibodies (e.g., camelid/llama antibodies), and antibody fragments.

The term "intact antibody" or "full-length antibody" refers to an antibody having a structure substantially similar to a native antibody structure. This includes an antibody comprising two light chains each comprising a variable region and a light chain constant region (CL) and two heavy chains each comprising a variable region and at least heavy chain constant regions CH1, CH2, and CH3.

The term "antibody fragment" as used herein refers to a molecule other than an intact antibody that comprises a portion of an antibody and generally an antigen-binding site. Examples of antibody fragments include, but are not limited to, Fab, Fab', F(ab')2, Fv, disulfide-linked Fv (sdFv), Fd, linear antibodies, single chain antibody molecules (e.g., scFv), diabodies, tribodies, tetrabodies, minibodies, dual variable domain antibodies (DVD), single variable domain antibodies, and multispecific antibodies formed from antibody fragments.

The term "variable region" as used herein refers to the region of an antibody light chain or the region of an antibody heavy chain that is involved in binding the antibody to antigen. The variable region of an antibody heavy chain and an antibody light chain have similar structures, and generally comprise four framework regions and three complementarity determining regions (CDRs) (also known as hypervariable regions).

The term "framework regions" refers to amino acid residues other than the CDR residues within a variable region. The variable region generally comprises four framework regions, FR1, FR2, FR3, and FR4.

The term "monoclonal antibody" as used herein refers to a substantially homogenous antibody population involved in the highly specific recognition and binding of a single antigenic determinant or epitope. The individual antibodies comprising the population are identical, except for possible naturally occurring mutations that may be present in minor amounts. The term "monoclonal antibody" encompasses intact and full-length monoclonal antibodies as well as antibody fragments (e.g., Fab, Fab', F(ab')2, Fv), single chain (scFv) antibodies, fusion proteins comprising an antibody fragment, and any other modified immunoglobulin molecule comprising an antigen-binding site. Furthermore, "monoclonal antibody" refers to such antibodies made by any number of techniques, including but not limited to, hybridoma production, phage library display, recombinant expression, and transgenic animals.

The term "chimeric antibody" as used herein refers to an antibody in which a portion of the heavy and/or light chain is derived from a particular source or species, while the remainder of the heavy and/or light chain is derived from a different source or species.

The term "humanized antibody" as used herein refers to a chimeric antibody that generally comprises human immunoglobulins (e.g., recipient antibody) in which the native CDR residues are replaced by residues from corresponding CDRs from a nonhuman species (e.g., donor antibody) such as mouse, rat, rabbit, or nonhuman primate, wherein the donor antibody has the desired specificity, affinity, and/or activity. In some instances, one or more residues within one or more framework regions of the human immunoglobulin are replaced by corresponding nonhuman residues. Furthermore, humanized antibodies can comprise residues that are not found in the recipient antibody or in the donor antibody. These modifications may be made to further refine and/or optimize antibody characteristics. A humanized antibody may comprise variable regions containing all or substantially all of the CDRs that correspond to those of a nonhuman immunoglobulin and all or substantially all of the framework regions that correspond to those of a human immunoglobulin. In some embodiments, the humanized antibody will comprise at least a portion of an immunoglobulin Fc region (e.g., hinge region, CH1, CH2, and/or CH3), typically that of a human immunoglobulin.

The term "human antibody" as used herein refers to an antibody that possesses an amino acid sequence that corresponds to an antibody produced by a human and/or an antibody that has been made using any of the techniques that are known to those of skill in the art for making human antibodies. These techniques include, but not limited to, phage display libraries, yeast display libraries, transgenic animals, and B-cell hybridoma technology. A human antibody as defined herein excludes a humanized antibody comprising residues from a non-human source.

The terms "epitope" and "antigenic determinant" are used interchangeably herein and refer to that portion of an antigen or target capable of being recognized and bound by a particular binding agent or binding agent (e.g., an antibody). When the antigen or target is a polypeptide, epitopes can be formed both from contiguous amino acids and noncontiguous amino acids juxtaposed by tertiary folding of the protein. Epitopes formed from contiguous amino acids (also referred to as linear epitopes) are typically retained upon protein denaturing, whereas epitopes formed by tertiary folding (also referred to as conformational epitopes) are typically lost upon protein denaturing. An epitope typically includes at least 3, and more usually, at least 5, 6, 7, or 8-10 amino acids in a unique spatial conformation. Epitopes can be predicted using any one of a large number of software bioinformatic tools available on the internet. X-ray crystallography may be used to characterize an epitope on a target protein by analyzing the amino acid residue interactions of an antigen/antibody complex.

The term "specifically binds" as used herein refers to a binding agent (e.g., an antibody) that interacts more frequently, more rapidly, with greater duration, with greater affinity, or with some combination of the above to a particular antigen, epitope, protein, or target molecule than with alternative substances. In some embodiments, a protein (e.g., an antibody) that specifically binds an antigen (e.g., human LEAP2) may bind related antigens (e.g., mouse LEAP2 or cyno LEAP2). An antibody that specifically binds an antigen can be identified, for example, by immunoassays, ELISAs, surface plasmon resonance (SPR) technology (e.g., Biacore), FACS, or other techniques known to those of ordinary skill in the art.

The terms "polypeptide" and "peptide" and "protein" are used interchangeably herein and refer to polymers of amino acids of any length. As used herein, the term "peptide" will generally refer to a polymer of less than 50 amino acids, e.g., 5-50 amino acids. The polymer may be linear or branched, it may comprise modified amino acids, and it may be interrupted by non-amino acids. The terms also encompass an amino acid polymer that has been modified naturally or by intervention; for example, by disulfide bond formation, glycosylation, lipidation, acetylation, phosphorylation, or any other manipulation or modification. Also included within the definition are, for example, polypeptides containing one or more analogs of an amino acid, including but not limited to, unnatural amino acids, as well as other modifications known in the art. It is understood that, because some of the polypeptides of this disclosure may be based upon antibodies, the term "polypeptide" encompasses polypeptides as a single chain and polypeptides of two or more associated chains.

The terms "polynucleotide" and "nucleic acid" and "nucleic acid molecule" are used interchangeably herein and refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity may be measured using sequence comparison software or algorithms or by visual inspection. Various algorithms and software that may be used to obtain alignments of amino acid or nucleotide sequences are well-known in the art. These include, but are not limited to, BLAST, ALIGN, Megalign, BestFit, GCG Wisconsin Package, and variants thereof. In some embodiments, two polynucleotides or polypeptides of the disclosure are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In some embodiments, identity exists over a region of the sequences that is at least about 10, at least about 20, at least about 40-60 nucleotides or amino acid residues, at least about 60-80 nucleotides or amino acid residues in length, or any integral value there between. In some embodiments, identity exists over a longer region than 60-80 nucleotides or amino acid residues, such as at least about 80-100 nucleotides or amino acid residues, and in some embodiments the sequences are substantially identical over the full length of the sequences being compared, for example, (i) the coding region of a nucleotide sequence or (ii) an amino acid sequence.

The phrase "conservative amino acid substitution" as used herein refers to a substitution in which one amino acid residue is replaced with another amino acid residue having a similar side chain. Families of amino acid residues having similar side chains have been generally defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is considered to be a conservative substitution. Generally, conservative substitutions in the sequences of polypeptides and/or antibodies do not abrogate the binding of the polypeptide or antibody to the target binding site. Methods of identifying nucleotide and amino acid conservative substitutions that do not eliminate binding are well-known in the art.

The term "vector" as used herein means a construct, which is capable of delivering, and usually expressing, one or more gene(s) or sequence(s) of interest in a host cell. Examples of vectors include, but are not limited to, viral vectors, naked DNA or RNA expression vectors, plasmid, cosmid, or phage vectors, DNA or RNA expression vectors associated with cationic condensing agents, and DNA or RNA expression vectors encapsulated in liposomes.

The term "isolated" as used herein refers to a polypeptide, peptide, soluble protein, antibody, polynucleotide, vector, cell, or composition that is in a form not found in nature. An "isolated" antibody is substantially free of material from the cellular source from which it is derived. In some embodiments, isolated polypeptides, peptides, soluble proteins, antibodies, polynucleotides, vectors, cells, or compositions are those which have been purified to a degree that they are no longer in a form in which they are found in nature. In some embodiments, a polypeptide, peptide, soluble protein, antibody, polynucleotide, vector, cell, or composition that is isolated is substantially pure. A polypeptide, peptide, soluble protein, antibody, polynucleotide, vector, cell, or composition may be isolated from a natural source or from a source such as an engineered cell line.

The term "substantially pure" as used herein refers to material which is at least 50% pure (i.e., free from contaminants), at least 90% pure, at least 95% pure, at least 98% pure, or at least 99% pure.

The term "subject" refers to any animal (e.g., a mammal), including, but not limited to, humans, non-human primates, canines, felines, pigs, rabbits, rodents, and the like, which is to be the recipient of a treatment or therapy. Generally, the terms "subject" and "subject" are used interchangeably herein. In some embodiments, the term subject is used in reference to a human subject.

The term "pharmaceutically acceptable" as used herein refers to a substance approved or approvable by a regulatory agency or listed in the U.S. Pharmacopeia, European Pharmacopeia, or other generally recognized pharmacopeia for use in animals, including humans.

The terms "pharmaceutically acceptable excipient, carrier, or adjuvant" or "acceptable pharmaceutical carrier" as used herein refer to an excipient, carrier, or adjuvant that can be administered to a subject, together with at least one therapeutic agent (e.g., an antibody), and which does not have an effect on the pharmacological activity of the therapeutic agent. In general, those of skill in the art and the U.S. FDA consider a pharmaceutically acceptable excipient, carrier, or adjuvant to be an inactive ingredient of any formulation.

The term "pharmaceutical formulation" or "pharmaceutical composition" as used herein refers to a preparation that is in such form as to permit the biological activity of the agent (e.g., an antibody) to be effective. A pharmaceutical formulation or composition generally comprises additional components, such as a pharmaceutically acceptable excipient, carrier, adjuvant, buffers, etc.

The term "effective amount" or "therapeutically effective amount" as used herein refers to the amount of a binding agent (e.g., an antibody or peptide) which is sufficient to reduce and/or ameliorate the severity and/or duration of a disease, disorder or condition and/or a symptom in a subject. The term also encompasses an amount of a binding agent necessary for the (i) reduction or amelioration of the advancement or progression of a given disease, disorder, or condition, (ii) reduction or amelioration of the recurrence, development, or onset of a given disease, disorder, or condition, and/or (iii) the improvement or enhancement of the prophylactic or therapeutic effect(s) of another agent or therapy (e.g., an agent other than the binding agents provided herein).

The term "therapeutic effect" as used herein refers to the effect and/or ability of a binding agent (e.g., an antibody or peptide) to reduce and/or ameliorate the severity and/or duration of a disease, disorder, or condition and/or a symptom in a subject. The term also encompasses the ability of a binding agent to (i) reduce or ameliorate the advancement or progression of a given disease, disorder, or condition, (ii) reduce or ameliorate the recurrence, development, or onset of a given disease, disorder, or condition, and/or (iii) to improve or enhance the prophylactic or therapeutic effect(s) of another agent or therapy (e.g., an agent other than the binding agents provided herein).

The term "treat" or "treatment" or "treating" or "to treat" or "alleviate" or "alleviation" or "alleviating" or "to alleviate" as used herein refers to both (1) therapeutic measures that aim to cure, slow down, lessen symptoms of, and/or halt progression of a pathologic condition or disorder and (2) prophylactic or preventative measures that aim to prevent or slow down the development of a targeted pathologic condition or disorder. Thus, those in need of treatment include those already with the disorder, those at risk of having/developing the disorder, and those in whom the disorder is to be prevented.

The term "prevent" or "prevention" or "preventing" as used herein refers to the partial or total inhibition of the development, recurrence, onset, or spread of a disease, disorder, or condition, or a symptom thereof in a subject.

The term "prophylactic agent" as used herein refers to an agent that partially or totally inhibits the development, recurrence, onset, or spread of a disease, disorder or condition, or a symptom thereof in a subject.

As used herein, reference to "about" or "approximately" a value or parameter includes (and describes) embodiments that are directed to that value or parameter. For example, a description referring to "about X" includes description of "X".

As used in the present disclosure and claims, the singular forms "a", "an" and "the" include plural forms unless the context clearly dictates otherwise.

It is understood that wherever embodiments are described herein with the term "comprising" otherwise analogous embodiments described in terms of "consisting of" and/or "consisting essentially of" are also provided. It is also understood that wherever embodiments are described herein with the phrase "consisting essentially of" otherwise analogous embodiments described in terms of "consisting of" are also provided.

The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

II. LEAP2 and LEAP2-Binding Agents

Representative amino acid (aa) sequences for full length human LEAP2 (e.g., UniProtKB No. Q969E1), mouse LEAP2 (e.g., UniProtKB No. QQ91V13), rat LEAP2 (e.g., UniProtKB No. Q5M9I7), and cynomolgus ("cyno") (e.g., NCBI Ref. No. XP_005557816.1) are known to those of skill in the art and representative sequences are provided herein as SEQ ID NO:1, SEQ ID NO:16, SEQ ID NO:18, and SEQ ID NO:13, respectively. As used herein, reference to amino acid positions of LEAP2 refer to the numbering of amino acid sequences including the signal sequence.

Analyses of full length human LEAP2 (SEQ ID NO:1) have shown that amino acids 1-22 comprise a signal peptide and amino acids 23-77 comprise a proprotein. Amino acids 23-37 are referred to as the LEAP2 propeptide. Amino acids 38-77 are the mature LEAP2 peptide. As used herein, the terms "LEAP2" and "LEAP 2 peptide" will generally refer to a mature LEAP2 peptide. In some embodiments, a LEAP 2 peptide has the amino acid sequence set forth in SEQ ID NO:2; which corresponds to amino acids 38-77 of SEQ ID NO:1. FIG. 2A shows a representative structure of full length LEAP2 and FIG. 2B shows the amino acid sequences of human and mouse full length LEAP2. LEAP2 is found in a number of other species, including mammals, amphibians, and fish and is highly conserved. FIG. 2C presents an alignment of representative full length LEAP2 amino acid sequences from various vertebrate species.

In some embodiments, the present disclosure provides LEAP2 peptides or variants thereof that bind GHSR. The terms "variant of a LEAP2 peptide," "LEAP2 peptide variant," and "LEAP2 variant" as used herein include natural or native variants, allelic variants, engineered variants, peptide analogs, peptide mimetics, and similar derivatives of a LEAP 2 peptide prepared by techniques known to those of skill in the art. In some embodiments, a LEAP2 variant comprises an amino acid sequence having at least about 75%, at least about 80%, at least about 85%, at least about 90%, at least about 95%, at least about 98%, at least about 99% amino acid sequence identity to amino acids 1-77 of SEQ ID NO:1. In some embodiments, a LEAP2 variant comprises an amino acid sequence having at least about 75%, at least about 80%, at least about 85%, at least about 90%, at least about 95%, at least about 98%, at least about 99% amino acid sequence identity to amino acids 23-37 of SEQ ID NO:1. In some embodiments, a LEAP2 variant comprises an amino acid sequence having at least about 75%, at least about 80%, at least about 85%, at least about 90%, at least about 95%, at least about 98%, at least about 99% amino acid sequence identity to amino acids 23-77 of SEQ ID NO:1. In some embodiments, a LEAP2 variant comprises an amino acid sequence having at least about 75%, at least about 80%, at least about 85%, at least about 90%, at least about 95%, at least about 98%, at least about 99% amino acid sequence identity to amino acids 38-77 of SEQ ID NO:1. In some embodiments, a LEAP2 variant comprises an amino acid sequence having at least about 75%, at least about 80%, at least about 85%, at least about 90%, at least about 95%, at least about 98%, at least about 99% amino acid sequence identity to SEQ ID NO:2. In some embodiments, a LEAP2 variant comprises 1 to 20 amino acid substitutions (e.g., 1, 2, 3, 4, 5, 6, 7, 8, 9, 10, 11, 12, 13, 14, or 15-20 amino acid substitutions) as compared to SEQ ID NO:1. In some embodiments, a LEAP2 variant comprises 1 to 10 amino acid substitutions (e.g., 1, 2, 3, 4, 5, 6, 7, 8, 9, or 10 amino acid substitutions) as compared to SEQ ID NO:2. In some embodiments, the amino acid substitutions are conservative amino acid substitutions. In some embodiments, a LEAP2 variant is not a peptide consisting of the amino acid sequence SEQ ID NO:3 or SEQ ID NO:4.

In some embodiments, a LEAP2 variant comprises about 10 amino acids to about 15 amino acids of SEQ ID NO:2. In some embodiments, a LEAP2 variant comprises about 10 amino acids to about 25 amino acids of SEQ ID NO:2. In some embodiments, a LEAP2 variant comprises about 10 amino acids to about 30 amino acids of SEQ ID NO:2. In some embodiments, a LEAP2 variant comprises about 10 amino acids to about 35 amino acids of SEQ ID NO:2. In some embodiments, a LEAP2 variant comprises about 10 amino acids to about 39 amino acids of SEQ ID NO:2.

A LEAP2 variant is expected to bind GHSR and/or affect GHSR activity (unless designed to be a negative control). In some embodiments, a LEAP2 variant may have a different binding affinity to GHSR than parental LEAP2 (e.g., increased or decreased GHSR binding). In some embodiments, a LEAP2 variant has a stronger binding affinity to GHSR than parental LEAP2. In some embodiments, a LEAP2 variant has a weaker binding affinity to GHSR than parental LEAP2.

In some embodiments, LEAP2 or a variant thereof, binds GHSR and modulates its activity. In some embodiments, LEAP2 or a variant thereof, that binds GHSR and modulates its activity, is not fused to a heterologous polypeptide.

Peptides and peptide variants can be produced using methods known in the art. In some embodiments, peptides are produced, in whole or in part, using standard recombinant DNA technology. In some embodiments, peptides are synthesized, in whole or in part, using chemical methods. In some embodiments, peptide synthesis is performed using various solid-phase techniques. In some embodiments, peptide synthesis is performed using an automated peptide synthesizer (e.g., a Biotage instrument). In some embodiments, peptides and peptide variants are synthesized using combinatorial methodologies. Synthetic mimetics and peptides incorporating mimetics can be synthesized using a variety of procedures and methodologies known in the art.

Peptides can be modified by a wide variety of chemical methods known to those of skill in the art. Peptide sequence variations, substitutions, and/or modifications can also be made using methods such as site-directed mutagenesis, alanine scanning, and/or PCR-based mutagenesis. Site-directed mutagenesis, cassette mutagenesis, restriction selection mutagenesis, and other techniques can be performed on cloned DNA to produce peptide sequences, variants, fusions, chimeras, and other derivatives thereof.

A "produced" or "synthesized" peptide sequence is a peptide made by any method involving manipulation by the hand of man. Such methods include but are not limited to, chemical synthesis, recombinant DNA technology, biochemical or enzymatic fragmentation of larger molecules, and combinations of the foregoing.

In some embodiments, LEAP2 (e.g., SEQ ID NO:2) or a variant thereof described herein, can be modified to form a chimeric molecule. In some embodiments, LEAP2 (e.g., SEQ ID NO:2) or a variant thereof described herein, can be modified to form a fusion polypeptide. In some embodiments, LEAP2 or a variant thereof comprises a heterologous polypeptide. In some embodiments, LEAP2 or a variant thereof is fused or linked to a heterologous polypeptide. In some embodiments, the heterologous polypeptide is linked to the amino-terminus of LEAP2 or a variant thereof. In some embodiments, the heterologous polypeptide is linked to the carboxyl-terminus of LEAP2 or a variant thereof. In some embodiments, LEAP2 or a variant thereof is not fused to a heterologous polypeptide sequence. polypeptide may be a immunoglobulin Fc polypeptide (e.g., human IgG Fc, such as IgG1 Fc), a serum albumin (e.g., human serum albumin, cynomolgus serum albumin or bovine serum albumin), or maltose binding protein.

In some embodiments, LEAP2 or a variant thereof has a length of 40 amino acids. In some embodiments, a LEAP2 variant has a length of more than 40 amino acids. In some embodiments, a LEAP2 variant has a length of about 41-60 amino acids. In some embodiments, a LEAP2 variant has a length of about 60-75 amino acids. In some embodiments, a LEAP2 variant has a length of about 75-100 amino acids. In some embodiments, a LEAP2 variant has a length of more than 100 amino acids.

In some embodiments, LEAP2 or a variant thereof is isolated. In some embodiments, LEAP2 or a variant thereof is substantially pure.

Representative amino acid sequences for human GHSR1a (UniProtKB No. Q92847) and GHSR1b (GenBank Accession No. NP 004113.1) are known to those of skill in the art and representative sequences are provided herein as SEQ ID NO:5 and SEQ IDNO:6, respectively. GHSR homologues are found in other species, including but not limited to, mouse, rat, and rhesus monkey. GHSRs in other species may or may not have multiple isoforms.

In some embodiments, the present disclosure provides agents that bind LEAP2. In some embodiments, a LEAP2-binding agent binds the mature LEAP2 peptide. In some embodiments, a LEAP2-binding agent binds a fragment of the mature LEAP2 peptide. In some embodiments, a LEAP2-binding agent binds an epitope on LEAP2. In some embodiments, a LEAP2-binding agent binds a linear epitope on LEAP2. In some embodiments, a LEAP2-binding agent binds a conformational epitope on LEAP2. In some embodiments, a LEAP2-binding agent binds human LEAP2. In some embodiments, a LEAP2-binding agent binds mouse LEAP2. In some embodiments, a LEAP2-binding agent binds rat LEAP2. In some embodiments, a LEAP2-binding agent binds monkey LEAP2. In some embodiments, a LEAP2-binding agent binds human LEAP2 and mouse LEAP2. In some embodiments, a LEAP2-binding agent binds human LEAP2 and rat LEAP2. In some embodiments, a LEAP2-binding agent binds human LEAP2 and monkey LEAP2.

In some embodiments, a LEAP2-binding agent binds within amino acids 38-77 of human LEAP2. In some embodiments, a LEAP2-binding agent binds within amino acids 45-77 of human LEAP2. In some embodiments, a LEAP2-binding agent binds within amino acids 55-77 of human LEAP2. In some embodiments, a LEAP2-binding agent binds within amino acids 40-55 of human LEAP2. In some embodiments, a LEAP2-binding agent binds within amino acids 55-74 of human LEAP2.

In some embodiments, a LEAP2-binding agent binds within amino acids 38-77 of SEQ ID NO:1. In some embodiments, a LEAP2-binding agent binds within amino acids 45-77 of SEQ ID NO:1. In some embodiments, a LEAP2-binding agent binds within amino acids 50-77 of SEQ ID NO:1. In some embodiments, a LEAP2-binding agent binds within amino acids 40-55 of SEQ ID NO:1. In some embodiments, a LEAP2-binding agent binds within amino acids 55-74 of SEQ ID NO:1.

In some embodiments, a LEAP2-binding agent binds an epitope comprising amino acids within SEQ ID NO:2. In some embodiments, a LEAP2-binding agent binds an epitope comprising amino acids within amino acids 38-77 of SEQ ID NO:1. In some embodiments, a LEAP2-binding agent binds an epitope comprising amino acids within 45-77 of SEQ ID NO:1. In some embodiments, a LEAP2-binding agent binds an epitope comprising amino acids within amino acids 50-77 of SEQ ID NO:1. In some embodiments, a LEAP2-binding agent binds an epitope comprising amino acids within 40-55 of SEQ ID NO:1. In some embodiments, a LEAP2-binding agent binds an epitope comprising amino acids within amino acids 55-74 of SEQ ID NO:1. In some embodiments, a LEAP2-binding agent binds at least one amino acid within SEQ ID NO:2. In some embodiments, a LEAP2-binding agent binds at least one amino acid within amino acids 38-77 of SEQ ID NO:1. In some embodiments, a LEAP2-binding agent binds at least one amino acid within amino acids 45-77 of SEQ ID NO:1. In some embodiments, a LEAP2-binding agent binds at least one amino acid within amino acids 50-77 of SEQ ID NO:1. In some embodiments, a LEAP2-binding agent binds at least one amino acid within amino acids 40-55 of SEQ ID NO:1. In some embodiments, a LEAP2-binding agent binds at least one amino acid within amino acids 55-74 of SEQ ID NO:1.

In some embodiments, a LEAP2-binding agent is an antibody. In some embodiments, the antibody is a recombinant antibody. In some embodiments, the antibody is a monoclonal antibody. In some embodiments, the antibody is a chimeric antibody. In some embodiments, the antibody is a humanized antibody. In some embodiments, the antibody is a human antibody. In some embodiments, the antibody is an IgA, IgD, IgE, IgG, or IgM antibody. In some embodiments, the antibody is an IgG antibody. In some embodiments, the antibody is an IgG1 antibody. In some embodiments, the antibody is an IgG2 antibody. In some embodiments, the antibody is an IgG3 antibody. In some embodiments, the antibody is an IgG4 antibody. In some embodiments, the antibody is an antibody fragment comprising at least one antigen-binding site. In some embodiments, the antibody is a scFv. In some embodiments, the antibody is a disulfide-linked scFv. In some embodiments, the antibody is a Fab. In some embodiments, the antibody is a bispecific antibody or a multispecific antibody. In some embodiments, the antibody is a monovalent antibody. In some embodiments, the antibody is a monospecific antibody. In some embodiments, the antibody is a bivalent antibody.

In some embodiments, the antibody is isolated. In some embodiments, the antibody is substantially pure.

In some embodiments, a LEAP2-binding agent is a polyclonal antibody. Polyclonal antibodies can be prepared by any method known to those of skill in the art. In some embodiments, polyclonal antibodies are produced by immunizing an animal (e.g., a rabbit, rat, mouse, goat, donkey) with an antigen of interest (e.g., a purified peptide fragment, a recombinant protein, or a fusion protein) using multiple subcutaneous or intraperitoneal injections. In some embodiments, the antigen is conjugated to a carrier such as keyhole limpet hemocyanin (KLH), serum albumin, bovine thyroglobulin, or soybean trypsin inhibitor. The antigen (with or without a carrier protein) is diluted in sterile saline and usually combined with an adjuvant (e.g., Complete or Incomplete Freund's Adjuvant) to form a stable emulsion. After a period of time, polyclonal antibodies are recovered from the immunized animal (e.g., from blood or ascites). In some embodiments, the polyclonal antibodies are purified from serum or ascites according to standard methods in the art including, but not limited to, affinity chromatography, ion-exchange chromatography, gel electrophoresis, and/or dialysis.

In some embodiments, a LEAP2-binding agent is a monoclonal antibody. Monoclonal antibodies can be prepared by any method known to those of skill in the art. In some embodiments, monoclonal antibodies are prepared using hybridoma methods known to one of skill in the art. For example, using a hybridoma method, a mouse, rat, rabbit, hamster, or other appropriate host animal, is immunized as described above. In some embodiments, lymphocytes are immunized in vitro. In some embodiments, the immunizing antigen is a human protein or a fragment thereof. In some embodiments, the immunizing antigen is a mouse protein or a fragment thereof. In some embodiments, the immunizing antigen is a cyno protein or a fragment thereof.

Following immunization, lymphocytes are isolated and fused with a suitable myeloma cell line using, for example, polyethylene glycol. The hybridoma cells are selected using specialized media as known in the art and unfused lymphocytes and myeloma cells do not survive the selection process. Hybridomas that produce monoclonal antibodies directed to a chosen antigen can be identified by a variety of methods including, but not limited to, immunoprecipitation, immunoblotting, and in vitro binding assays (e.g., flow cytometry, FACS, ELISA, SPR (e.g., Biacore), and radio-immunoassay). Once hybridoma cells that produce antibodies of the desired specificity, affinity, and/or activity are identified, the clones may be subcloned by limiting dilution or other techniques. The hybridomas can be propagated either in in vitro culture using standard methods or in vivo as ascites tumors in an animal. The monoclonal antibodies can be purified from the culture medium or ascites fluid according to standard methods in the art including, but not limited to, affinity chromatography, ion-exchange chromatography, gel electrophoresis, and dialysis.

In some embodiments, monoclonal antibodies are made using recombinant DNA techniques as known to one skilled in the art. For example, the polynucleotides encoding an antibody are isolated from mature B-cells or hybridoma cells, such as by RT-PCR using oligonucleotide primers that specifically amplify the genes encoding the heavy and light chains of the antibody and their sequence is determined using standard techniques. The isolated polynucleotides encoding the heavy and light chains are then cloned into suitable expression vectors that produce the monoclonal antibodies when transfected into host cells such as E. coli, simian COS cells, Chinese hamster ovary (CHO) cells, or myeloma cells that do not otherwise produce immunoglobulin proteins.

In some embodiments, recombinant monoclonal antibodies are isolated from phage display libraries expressing variable domains or CDRs of a desired species (e.g., mouse or human). Screening of phage libraries can be accomplished by various techniques known in the art.

In some embodiments, a monoclonal antibody is modified by using recombinant DNA technology to generate alternative antibodies. In some embodiments, the constant domains of the light chain and heavy chain of a mouse monoclonal antibody are replaced with the constant regions of a human antibody to generate a chimeric antibody. In some embodiments, the constant regions are truncated or removed to generate a desired antibody fragment of a monoclonal antibody. In some embodiments, site-directed or high-density mutagenesis of the variable region(s) is used to optimize specificity and/or affinity of a monoclonal antibody.

In some embodiments, a LEAP2-binding agent is a humanized antibody. Various methods for generating humanized antibodies are known in the art. In some embodiments, a humanized antibody comprises one or more amino acid residues that have been introduced into its sequence from a source that is non-human. In some embodiments, humanization is performed by substituting one or more amino acids of a CDR sequence of a human antibody with the corresponding amino acids from a non-human antibody (e.g., a mouse antibody). In some embodiments, the humanized antibodies are constructed by substituting all six CDRs of a human antibody with corresponding amino acids from the CDRs of a non-human antibody (e.g., a mouse antibody).

The choice of which human heavy chain variable region and/or light chain variable region are used for generating humanized antibodies can be made based on a variety of factors and by a variety of methods known in the art. In some embodiments, the "best-fit" method is used where the sequence of the variable region of a non-human (e.g., rodent) antibody is screened against the entire library of known human variable region sequences. The human sequence that is most similar to that of the non-human (e.g., rodent) sequence is selected as the human variable region framework for the humanized antibody. In some embodiments, a particular variable region framework derived from a consensus sequence of all human antibodies of a particular subgroup of light or heavy chains is selected as the variable region framework. In some embodiments, the variable region framework sequence is derived from the consensus sequences of the most abundant human subclasses. In some embodiments, human germline genes are used as the source of the variable region framework sequences.

Other methods for humanization include, but are not limited to, (i) a method called "superhumanization" that is described as the direct transfer of CDRs to a human germline framework, (ii) a method termed Human String Content (HSC) that is based on a metric of "antibody humanness", (iii) methods based on generation of large libraries of humanized variants (including phage, ribosomal, and yeast display libraries), and (iv) methods based on framework region shuffling.

In some embodiments, a LEAP2-binding agent is a human antibody. Human antibodies can be prepared using various techniques known in the art. In some embodiments, human antibodies are generated from immortalized human B lymphocytes immunized in vitro. In some embodiments, human antibodies are generated from lymphocytes isolated from an immunized individual. In any case, cells that produce an antibody directed against a target antigen can be generated and isolated. In some embodiments, a human antibody is selected from a phage library, where that phage library expresses human antibodies. Alternatively, phage display technology may be used to produce human antibodies and antibody fragments in vitro, from immunoglobulin variable region gene repertoires from unimmunized donors. Techniques for the generation and use of antibody phage libraries are well-known in the art. Once antibodies are identified, affinity maturation strategies known in the art, including but not limited to, chain shuffling and site-directed mutagenesis, may be employed to generate higher affinity human antibodies. In some embodiments, human antibodies are produced in transgenic mice that contain human immunoglobulin loci. Upon immunization these mice are capable of producing the full repertoire of human antibodies in the absence of endogenous immunoglobulin production.

In some embodiments, a LEAP2-binding agent is a bispecific antibody. Bispecific antibodies are capable of recognizing and binding at least two different antigens or epitopes. The different epitopes can either be within the same molecule (e.g., two epitopes on LEAP2) or on different molecules (e.g., one epitope on LEAP2 and one epitope on a different target). In some embodiments, a bispecific antibody has enhanced potency as compared to an individual antibody or to a combination of more than one antibody. In some embodiments, a bispecific antibody has reduced toxicity as compared to an individual antibody or to a combination of more than one antibody. It is known to those of skill in the art that any therapeutic agent may have unique pharmacokinetics (PK) (e.g., circulating half-life). In some embodiments, a bispecific antibody has the ability to synchronize the PK of two active binding agents wherein the two individual binding agents have different PK profiles. In some embodiments, a bispecific antibody has the ability to concentrate the actions of two agents in a common area (e.g., tissue) in a subject. In some embodiments, a bispecific antibody has the ability to concentrate the actions of two agents to a common target (e.g., a specific cell type). In some embodiments, a bispecific antibody has the ability to target the actions of two agents to more than one biological pathway or function. In some embodiments, a bispecific antibody has the ability to target two different cells and bring them closer together.

In some embodiments, a bispecific antibody has decreased toxicity and/or side effects. In some embodiments, a bispecific antibody has decreased toxicity and/or side effects as compared to a mixture of the two individual antibodies or the antibodies as single agents. In some embodiments, a bispecific antibody has an increased therapeutic index. In some embodiments, a bispecific antibody has an increased therapeutic index as compared to a mixture of the two individual antibodies or the antibodies as single agents.

Several techniques for making bispecific antibodies are known by those skilled in the art. In some embodiments, the bispecific antibodies comprise heavy chain constant regions with modifications in the amino acids that are part of the interface between the two heavy chains. These modifications are made to enhance heterodimer formation and generally reduce or eliminate homodimer formation. In some embodiments, the bispecific antibodies are generated using a knobs-into-holes (KIH) strategy. In some embodiments, the bispecific antibodies comprise variant hinge regions incapable of forming disulfide linkages between identical heavy chains (e.g., reduce homodimer formation). In some embodiments, the bispecific antibodies comprise heavy chains with changes in amino acids that result in altered electrostatic interactions. In some embodiments, the bispecific antibodies comprise heavy chains with changes in amino acids that result in altered hydrophobic/hydrophilic interactions.

Bispecific antibodies can be intact antibodies or antibody fragments comprising antigen-binding sites.

LEAP2-binding agents with more than two valencies are also contemplated. In some embodiments, trispecific or tetraspecific antibodies are generated.

In some embodiments, a LEAP2-binding agent is an antibody that binds LEAP2. In some embodiments, an anti-LEAP2 antibody binds human LEAP2. In some embodiments, an anti-LEAP2 antibody binds mouse LEAP2. In some embodiments, an anti-LEAP2 antibody binds human and mouse LEAP2. In some embodiments, an anti-LEAP2 antibody binds a portion or fragment of LEAP2. In some embodiments, an anti-LEAP2 antibody binds within amino acids 38-77 of human LEAP2. In some embodiments, an anti-LEAP2 antibody binds within amino acids 45-77 of human LEAP2. In some embodiments, an anti-LEAP2 antibody binds within amino acids 50-77 of human LEAP2. In some embodiments, an anti-LEAP2 antibody binds an epitope within amino acids 38-77 of LEAP2.

CDRs of an antibody are defined by those skilled in the art using a variety of methods/systems. These systems and/or definitions have been developed and refined over a number of years and include Kabat, Chothia, IMGT, AbM, and Contact. The Kabat definition is based on sequence variability and is commonly used. The Chothia definition is based on the location of the structural loop regions. The IMGT system is based on sequence variability and location within the structure of the variable domain. The AbM definition is a compromise between Kabat and Chothia. The Contact definition is based on analyses of the available antibody crystal structures. An Exemplary system is a combination of Kabat and Chothia. Software programs (e.g., abYsis) are available and known to those of skill in the art for analysis of antibody sequence and determination of CDRs.

The specific CDR sequences defined herein are generally based on a combination of Kabat and Chothia definitions (Exemplary system). However, it will be understood that reference to a heavy chain CDR or CDRs and/or a light chain CDR or CDRs of a specific antibody will encompass all CDR definitions as known to those of skill in the art.

In some embodiments, a LEAP2-binding agent is an anti-LEAP2 antibody that comprises one, two, three, four, five, and/or six CDRs of any one of the antibodies described herein. In some embodiments, an anti-LEAP2 antibody comprises (i) one, two, and/or three heavy chain CDRs from Table 1, and/or (ii) one, two, and/or three light chain CDRs from Table 1. In some embodiments, an anti-LEAP2 antibody comprises (i) one, two, and/or three heavy chain CDRs from Table 2, and/or (ii) one, two, and/or three light chain CDRs from Table 2.

TABLE 1

| | Antibody M1/M2 | | | | | |
|---|---|---|---|---|---|---|
| | Exemplary | IMGT | Kabat | Chothia | Contact | AbM |
| VH CDR1 | GYTFTSYWMH (SEQ ID NO: 20) | GYTFTSYW (SEQ ID NO: 32) | SYWMH (SEQ ID NO: 33) | GYTFTSY (SEQ ID NO: 34) | TSYWMH (SEQ ID NO: 35) | GYTFTSYWMH (SEQ ID NO: 20) |
| VH CDR2 | AIYPGNSDTSYKQKFKG (SEQ ID NO: 21) | IYPGNSDT (SEQ ID NO: 36) | AIYPGNSDTSYKQKFKG (SEQ ID NO: 21) | PGNS (SEQ ID NO: 37) | WIGAIYPGNSDTS (SEQ ID NO: 38) | AIYPGNSDTS (SEQ ID NO: 39) |
| VH CDR3 | GKEEYLFAMDY (SEQ ID NO: 22) | TYGKEEYLFAMDY (SEQ ID NO: 40) | GKEEYLFAMDY (SEQ ID NO: 22) | KEEYLFAMD (SEQ ID NO: 41) | TYGKEEYLFAMD (SEQ ID NO: 42) | GKEEYLFAMDY (SEQ ID NO: 22) |
| VL CDR1 | KSSQSLLYSSNQKNYLA (SEQ ID NO: 23) | QSLLYSSNQKNY (SEQ ID NO: 43) | KSSQSLLYSSNQKNYLA (SEQ ID NO: 23) | SQSLLYSSNQKNY (SEQ ID NO: 44) | LYSSNQKNYLAWY (SEQ ID NO: 45) | KSSQSLLYSSNQKNYLA (SEQ ID NO: 23) |
| VL CDR2 | WASTRES (SEQ ID NO: 24) | WAS (SEQ ID NO: 46) | WASTRES (SEQ ID NO: 24) | WAS (SEQ ID NO: 46) | LLIYWASTRE (SEQ ID NO: 47) | WASTRES (SEQ ID NO: 24) |
| VL CDR3 | QQYYSYPT (SEQ ID NO: 25) | QQYYSYPT (SEQ ID NO: 25) | QQYYSYPT (SEQ ID NO: 25) | YYSYP (SEQ ID NO: 48) | QQYYSYP (SEQ ID NO: 49) | QQYYSYPT (SEQ ID NO: 25) |

Heavy chain variable region
EVQLQQSGTVLARPGASVKMSCKASGYTFTSYWMHWVKQRPGQGLEWIGAIYPGNSDTSYKQKFKGKAKLTAVTSASTVYMELSSLTDEDSAVYYCTY
GKEEYLFAMDYWGQGTSVTVSS (SEQ ID NO: 7)

Light chain variable region
DIVMSQSPSSLAVSVGEKVTMSCKSSQSLLYSSNQKNYLAWYQQKPGQSPKLLIYWASTRESGVPDRFTGSGSGTDFTLTISSVKAEDLAVYYCQQYY
SYPTFGGGTKLKIK (SEQ ID NO: 8)

TABLE 2

Antibody M18

| | Exemplary | IMGT | Kabat | Chothia | Contact | AbM |
|---|---|---|---|---|---|---|
| VH CDR1 | GYSFTNYYIH (SEQ ID NO: 26) | GYSFTNYY (SEQ ID NO: 50) | NYYIH (SEQ ID NO: 51) | GYSFTNY (SEQ ID NO: 52) | TNYYIH (SEQ ID NO: 53) | GYSFTNYYIH (SEQ ID NO: 26) |
| VH CDR2 | YIDPENGGINYNQKFKG (SEQ ID NO: 27) | IDPFNGGT (SEQ ID NO: 54) | YIDPENGGINYNQKFKG (SEQ ID NO: 27) | PFNG (SEQ ID NO: 55) | WIGYIDPENGGIN (SEQ ID NO: 56) | YIDPENGGIN (SEQ ID NO: 57) |
| VH CDR3 | RGYYYGFTY (SEQ ID NO: 28) | ARRGYYYGFTY (SEQ ID NO: 58) | RGYYYGFTY (SEQ ID NO: 28) | GYYYGFT (SEQ ID NO: 59) | ARRGYYYGFT (SEQ ID NO: 60) | RGYYYGFTY (SEQ ID NO: 28) |
| VL CDR1 | KASQSVDYDGDSYMN (SEQ ID NO: 29) | QSVDYDGDSY (SEQ ID NO: 61) | KASQSVDYDGDSYMN (SEQ ID NO: 29) | SQSVDYDGDSY (SEQ ID NO: 62) | DYDGDSYMNWY (SEQ ID NO: 63) | KASQSVDYDGDSYMN (SEQ ID NO: 29) |
| VL CDR2 | TASNLES (SEQ ID NO: 30) | TAS (SEQ ID NO: 64) | TASNLES (SEQ ID NO: 30) | TAS (SEQ ID NO: 64) | LLIYTASNLE (SEQ ID NO: 65) | TASNLES (SEQ ID NO: 30) |
| VL CDR3 | QQSNEDPYT (SEQ ID NO: 31) | QQSNEDPYT (SEQ ID NO: 31) | QQSNEDPYT (SEQ ID NO: 31) | SNEDPY (SEQ ID NO: 66) | QQSNEDPY (SEQ ID NO: 67) | QQSNEDPYT (SEQ ID NO: 31) |

Heavy chain variable region
EIQLQQSGPELMKPGASVKISCKASGYSFTNYYIHWVKQSHGKSLEWIGYIDPENGGINYNQKFKGKATLTVDKSSSTAYMHLSSLTFEDSAVYYC
ARRGYYYGFTYWGQGTLVTVSA (SEQ ID NO: 9)

Light chain variable region
DIVLTQSPASLAVSLGQRATISCKASQSVDYDGDSYMNWYQQKPGQPPKLLIYTASNLESGIPARFSGSGSGTDFTLNIHPVEEDAATYYCQQSN
EDPYTFGGGTKLEIK (SEQ ID NO: 10)

In some embodiments, a LEAP2-binding agent comprises a heavy chain CDR1, CDR2, and CDR3 and/or a light chain CDR1, CDR2, CDR3 from an antibody described herein. In some embodiments, a LEAP2-binding agent comprises a humanized version or humanized variant of an antibody described herein.

In some embodiments, a LEAP2-binding agent comprises a heavy chain CDR1, CDR2, and CDR3 and/or a light chain CDR1, CDR2, and CDR3 from antibody M1/M2, a humanized version thereof, or variants thereof. In some embodiments, a LEAP2-binding agent comprises a heavy chain CDR1, a heavy chain CDR2, and a heavy chain CDR3 from antibody M1/M2. In other embodiments, a LEAP2-binding agent comprises a light chain CDR1, a light chain CDR2, and a light chain CDR3 from antibody M1/M2. In certain embodiments, a LEAP2-binding agent comprises a heavy chain CDR1, a heavy chain CDR2, a heavy chain CDR3, a light chain CDR1, light chain CDR2, and a light chain CDR3 from antibody M1/M2. In some embodiments, a LEAP2-binding agent is a humanized version of antibody M1/M2 (e.g., HzM1/M2). In some embodiments, a LEAP2-binding agent is a variant of antibody M1/M2. In some embodiments, a LEAP2-binding agent is a variant of antibody HzM1/M2

In some embodiments, a LEAP2-binding agent comprises a heavy chain CDR1, CDR2, and CDR3 and/or a light chain CDR1, CDR2, and CDR3 from antibody M18, a humanized version thereof, or variants thereof. In some embodiments, a LEAP2-binding agent comprises a heavy chain CDR1, a heavy chain CDR2, and a heavy chain CDR3 from antibody M18. In other embodiments, a LEAP2-binding agent comprises a light chain CDR1, a light chain CDR2, and a light chain CDR3 from antibody M18. In certain embodiments, a LEAP2-binding agent comprises a heavy chain CDR1, a heavy chain CDR2, a heavy chain CDR3, a light chain CDR1, light chain CDR2, and a light chain CDR3 from antibody M18. In some embodiments, a LEAP2-binding agent is a humanized version of antibody M18 (e.g., HzM18). In some embodiments, a LEAP2-binding agent is a variant of antibody M18. In some embodiments, a LEAP2-binding agent is a variant of antibody HzM18.

In some embodiments, a LEAP2-binding agent is an antibody. In some embodiments, a variant of an anti-LEAP2 antibody described herein comprises one to thirty conservative amino acid substitutions. In some embodiments, a variant of the anti-LEAP2 antibody comprises one to twenty-five conservative amino acid substitutions. In some embodiments, a variant of the anti-LEAP2 antibody comprises one to twenty conservative amino acid substitutions. In some embodiments, a variant of the anti-LEAP2 antibody comprises one to fifteen conservative amino acid substitutions. In some embodiments, a variant of the anti-LEAP2 antibody comprises one to ten conservative amino acid substitution(s). In some embodiments, a variant of the anti-LEAP2 antibody comprises one to five conservative amino acid substitution(s). In some embodiments, a variant of the anti-LEAP2 antibody comprises one to three conservative amino acid substitution(s). In some embodiments, the conservative amino acid substitution(s) is in a CDR of the antibody. In some embodiments, the conservative amino acid substitution(s) is not in a CDR of the antibody. In some embodiments, the conservative amino acid substitution(s) is in a framework region of the antibody.

In some embodiments, a LEAP2-binding agent (e.g., an antibody) comprises: (a) a heavy chain CDR1 comprising GYTFTSYWMH (SEQ ID NO:20), a heavy chain CDR2 comprising AIYPGNSDTSYKQKFKG (SEQ ID NO:21), and a heavy chain CDR3 comprising GKEEYLFAMDY (SEQ ID NO:22); and/or (b) a light chain CDR1 comprising KSSQSLLYSSNQKNYLA (SEQ ID NO:23), a light chain CDR2 comprising WASTRES (SEQ ID NO:24), and a light chain CDR3 comprising QQYYSYPT (SEQ ID NO:25). In some embodiments, a LEAP2-binding agent comprises a heavy chain CDR1 comprising GYTFTSYWMH (SEQ ID NO:20), a heavy chain CDR2 comprising AIYPGNSDTSYKQKFKG (SEQ ID NO:21), and a heavy chain CDR3 comprising GKEEYLFAMDY (SEQ ID NO:22). In some embodiments, a LEAP2-binding agent comprises a light chain CDR1 comprising KSSQSLLYSSNQKNYLA (SEQ ID NO:23), a light chain CDR2 comprising WASTRES (SEQ ID NO:24), and a light chain CDR3 comprising QQYYSYPT (SEQ ID NO:25). In some embodiments, a LEAP2-binding agent comprises (a) a heavy chain CDR1 comprising GYTFTSYWMH (SEQ ID NO:20), a heavy chain CDR2 comprising AIYPGNSDTSYKQKFKG (SEQ ID NO:21), and a heavy chain CDR3 comprising GKEEYLFAMDY (SEQ ID NO:22); and (b) a light chain CDR1 comprising KSSQSLLYSSNQKNYLA (SEQ ID NO:23), a light chain CDR2 comprising WASTRES (SEQ ID NO:24), and a light chain CDR3 comprising QQYYSYPT (SEQ ID NO:25).

In some embodiments, a LEAP2-binding agent (e.g., an antibody) comprises: (a) a heavy chain CDR1 comprising GYTFTSYWMH (SEQ ID NO:20), or a variant thereof comprising 1, 2, 3, or 4 amino acid substitutions; a heavy chain CDR2 comprising AIYPGNSDTSYKQKFKG (SEQ ID NO:21), or a variant thereof comprising 1, 2, 3, or 4 amino acid substitutions; a heavy chain CDR3 comprising GKEEYLFAMDY (SEQ ID NO:22), or a variant thereof comprising 1, 2, 3, or 4 amino acid substitutions; a light chain CDR1 comprising KSSQSLLYSSNQKNYLA (SEQ ID NO:23), or a variant thereof comprising 1, 2, 3, or 4 amino acid substitutions; a light chain CDR2 comprising WASTRES (SEQ ID NO:24), or a variant thereof comprising 1, 2, 3, or 4 amino acid substitutions; and a light chain CDR3 comprising QQYYSYPT (SEQ ID NO:25), or a variant thereof comprising 1, 2, 3, or 4 amino acid substitutions. In some embodiments, the amino acid substitutions are conservative substitutions. In some embodiments, a CDR comprises one conservative amino acid substitution. In some embodiments, a CDR comprises two conservative amino acid substitutions. In some embodiments, a CDR comprises three conservative amino acid substitutions. In some embodiments, a CDR comprises four conservative amino acid substitutions. In some embodiments, the CDR is a heavy chain CDR1. In some embodiments, the CDR is a heavy chain CDR2. In some embodiments, the CDR is a heavy chain CDR3. In some embodiments, the CDR is a light chain CDR1. In some embodiments, the CDR is a light chain CDR2. In some embodiments, the CDR is a light chain CDR3. In some embodiments, the substitutions are made as part of a humanization process. In some embodiments, the substitutions are made as part of a germline humanization process. In some embodiments, the substitutions are made as part of an affinity maturation process. In some embodiments, the substitutions are made as part of an optimization process.

In some embodiments, a LEAP2-binding agent (e.g., an antibody) comprises a heavy chain variable region having at least about 80% sequence identity to SEQ ID NO:7 and/or a light chain variable region having at least 80% sequence identity to SEQ ID NO:8. In some embodiments, a LEAP2-binding agent (e.g., an antibody) comprises a heavy chain variable region having at least about 85%, at least about 90%, at least about 95%, at least about 97%, or at least about 99% sequence identity to SEQ ID NO:7. In some embodiments, a LEAP2-binding agent (e.g., an antibody) comprises a light chain variable region having at least about 85%, at least about 90%, at least about 95%, at least about 97%, or at least about 99% sequence identity to SEQ ID NO:8.

In some embodiments, a LEAP2-binding agent (e.g., an antibody) comprises a heavy chain variable region having at least about 80% sequence identity to SEQ ID NO:7 and/or a light chain variable region having at least about 80% sequence identity to SEQ ID NO:8. In some embodiments, a LEAP2-binding agent (e.g., an antibody) comprises a heavy chain variable region having at least about 80% sequence identity to SEQ ID NO:7 and a light chain variable region having at least about 80% sequence identity to SEQ ID NO:8. In some embodiments, a LEAP2-binding agent (e.g., an antibody) comprises a heavy chain variable region having at least about 90% sequence identity to SEQ ID NO:7 and/or a light chain variable region having at least about 90% sequence identity to SEQ ID NO:8. In some embodiments, a LEAP2-binding agent (e.g., an antibody) comprises a heavy chain variable region having at least about 90% sequence identity to SEQ ID NO:7 and a light chain variable region having at least about 90% sequence identity to SEQ ID NO:8. In some embodiments, a LEAP2-binding agent (e.g., an antibody) comprises a heavy chain variable region having at least about 95% sequence identity to SEQ ID NO:7 and/or a light chain variable region having at least about 95% sequence identity to SEQ ID NO:8. In some embodiments, a LEAP2-binding agent (e.g., an antibody) comprises a heavy chain variable region having at least about 95% sequence identity to SEQ ID NO:7 and a light chain variable region having at least about 95% sequence identity to SEQ ID NO:8.

In some embodiments, a LEAP2-binding agent (e.g., an antibody) comprises a heavy chain variable region comprising SEQ ID NO:7. In some embodiments, a LEAP2-binding agent comprises a light chain variable region comprising SEQ ID NO:8. In some embodiments, a LEAP2-binding agent (e.g., an antibody) comprises a heavy chain variable region comprising SEQ ID NO:7 and a light chain variable region comprising SEQ ID NO:8.

In some embodiments, a LEAP2-binding agent (e.g., an antibody) comprises a CDR1, CDR2, and CDR3 from a heavy chain variable region having the amino acid sequence of SEQ ID NO:7 and a CDR1, CDR2, and CDR3 from a light chain variable region having the amino acid sequence of SEQ ID NO:8.

In some embodiments, a LEAP2-binding agent (e.g., an antibody) comprises (a) a heavy chain CDR1 comprising GYSFTNYYIH (SEQ ID NO:26), a heavy chain CDR2 comprising YIDPFNGGTNYNQKFKG (SEQ ID NO:27), and a heavy chain CDR3 comprising RGYYYGFTY (SEQ ID NO:28), and/or (b) a light chain CDR1 comprising KASQSVDYDGDSYMN (SEQ ID NO:29), a light chain CDR2 comprising TASNLES (SEQ ID NO:30), and a light chain CDR3 comprising QQSNEDPYT (SEQ ID NO:31). In some embodiments, a LEAP2-binding agent comprises a heavy chain CDR1 comprising GYSFTNYYIH (SEQ ID NO:26), a heavy chain CDR2 comprising YIDPFNGGTNYNQKFKG (SEQ ID NO:27), and a heavy chain CDR3 comprising RGYYYGFTY (SEQ ID NO:28). In some embodiments, a LEAP2-binding agent comprises a light chain CDR1 comprising KASQSVDYDGDSYMN (SEQ ID NO:29), a light chain CDR2 comprising TASNLES (SEQ ID NO:30), and a light chain CDR3 comprising QQSNEDPYT (SEQ ID NO:31). In some embodiments, a LEAP2-binding agent comprises (a) a heavy chain CDR1 comprising GYSFTNYYIH (SEQ ID NO:26), a heavy chain CDR2 comprising YIDPFNGGTNYNQKFKG (SEQ ID NO:27), and a heavy chain CDR3 comprising RGYYYGFTY (SEQ ID NO:28), and (b) a light chain CDR1 comprising KASQSVDYDGDSYMN (SEQ ID NO:29), a light chain CDR2 comprising TASNLES (SEQ ID NO:30), and a light chain CDR3 comprising QQSNEDPYT (SEQ ID NO:31).

In some embodiments, a LEAP2-binding agent (e.g., an antibody) comprises: (a) a heavy chain CDR1 comprising GYSFTNYYIH (SEQ ID NO:26), or a variant thereof comprising 1, 2, 3, or 4 amino acid substitutions; a heavy chain CDR2 comprising YIDPFNGGTNYNQKFKG (SEQ ID NO:27), or a variant thereof comprising 1, 2, 3, or 4 amino acid substitutions; a heavy chain CDR3 comprising RGYYYGFTY (SEQ ID NO:28), or a variant thereof comprising 1, 2, 3, or 4 amino acid substitutions; a light chain CDR1 comprising KASQSVDYDGDSYMN (SEQ ID NO:29), or a variant thereof comprising 1, 2, 3, or 4 amino acid substitutions; a light chain CDR2 comprising TASNLES (SEQ ID NO:30), or a variant thereof comprising 1, 2, 3, or 4 amino acid substitutions; and a light chain CDR3 comprising QQSNEDPYT (SEQ ID NO:31), or a variant thereof comprising 1, 2, 3, or 4 amino acid substitutions. In some embodiments, the amino acid substitutions are conservative substitutions. In some embodiments, a CDR comprises one conservative amino acid substitution. In some embodiments, a CDR comprises two conservative amino acid substitutions. In some embodiments, a CDR comprises three conservative amino acid substitutions. In some embodiments, a CDR comprises four conservative amino acid substitutions. In some embodiments, the CDR is a heavy chain CDR1. In some embodiments, the CDR is a heavy chain CDR2. In some embodiments, the CDR is a heavy chain CDR3. In some embodiments, the CDR is a light chain CDR1. In some embodiments, the CDR is a light chain CDR2. In some embodiments, the CDR is a light chain CDR3. In some embodiments, the substitutions are made as part of a humanization process. In some embodiments, the substitutions are made as part of a germline humanization process. In some embodiments, the substitutions are made as part of an affinity maturation process. In some embodiments, the substitutions are made as part of an optimization process.

In some embodiments, a LEAP2-binding agent (e.g., an antibody) comprises a heavy chain variable region having at least about 80% sequence identity to SEQ ID NO:9 and/or a light chain variable region having at least 80% sequence identity to SEQ ID NO:10. In some embodiments, a LEAP2-binding agent (e.g., an antibody) comprises a heavy chain variable region having at least about 85%, at least about 90%, at least about 95%, at least about 97%, or at least about 99% sequence identity to SEQ ID NO:9. In some embodiments, a LEAP2-binding agent (e.g., an antibody) comprises a light chain variable region having at least about 85%, at least about 90%, at least about 95%, at least about 97%, or at least about 99% sequence identity to SEQ ID NO:10.

In some embodiments, a LEAP2-binding agent (e.g., an antibody) comprises a heavy chain variable region having at least about 80% sequence identity to SEQ ID NO:9 and/or a light chain variable region having at least about 80% sequence identity to SEQ ID NO:10. In some embodiments, a LEAP2-binding agent (e.g., an antibody) comprises a heavy chain variable region having at least about 80% sequence identity to SEQ ID NO:9 and a light chain variable region having at least about 80% sequence identity to SEQ ID NO:10. In some embodiments, a LEAP2-binding agent (e.g., an antibody) comprises a heavy chain variable region having at least about 90% sequence identity to SEQ ID NO:9 and/or a light chain variable region having at least about 90% sequence identity to SEQ ID NO:10. In some embodiments, a LEAP2-binding agent (e.g., an antibody) comprises a heavy chain variable region having at least about 90% sequence identity to SEQ ID NO:9 and a light chain variable region having at least about 90% sequence identity to SEQ ID NO:10. In some embodiments, a LEAP2-binding agent (e.g., an antibody) comprises a heavy chain variable region having at least about 95% sequence identity to SEQ ID NO:9 and/or a light chain variable region having at least about 95% sequence identity to SEQ ID NO:10. In some embodiments, a LEAP2-binding agent (e.g., an antibody) comprises a heavy chain variable region having at least about 95% sequence identity to SEQ ID NO:9 and a light chain variable region having at least about 95% sequence identity to SEQ ID NO:10.

In some embodiments, a LEAP2-binding agent (e.g., an antibody) comprises a heavy chain variable region comprising SEQ ID NO:9. In some embodiments, a LEAP2-binding agent comprises a light chain variable region comprising SEQ ID NO:10. In some embodiments, a LEAP2-binding agent (e.g., an antibody) comprises a heavy chain variable region comprising SEQ ID NO:9 and a light chain variable region comprising SEQ ID NO:10.

In some embodiments, a LEAP2-binding agent (e.g., an antibody) comprises a CDR1, CDR2, and CDR3 from a heavy chain variable region having the amino acid sequence of SEQ ID NO:9 and a CDR1, CDR2, and CDR3 from a light chain variable region having the amino acid sequence of SEQ ID NO:10.

Provided herein are antibodies that compete with one or more of the antibodies described herein for binding to human LEAP2. In some embodiments, antibodies provided herein compete with one or more of the LEAP2-binding agents described herein for binding to human LEAP2. In some embodiments, an antibody provided herein binds the same epitope as one of the antibodies described herein. In some embodiments, an antibody provided herein binds an epitope overlapping with an epitope bound by one of the antibodies described herein. In some embodiments, an antibody that competes with one or more of the antibodies described herein for binding to LEAP2 is identified using a epitope binning method as described herein. Antibodies and antigen-binding fragments that compete with, or bind to the same epitope, as the antibodies described herein are expected to show similar functional properties.

In some embodiments, an agent (e.g., an antibody) competes for binding to LEAP2 with a LEAP2-binding agent (e.g., an antibody) described herein. In some embodiments, an antibody competes for binding to human LEAP2 with a LEAP2-binding agent (e.g., an antibody) described herein. In some embodiments, an antibody is tested against a "reference" antibody in a competitive binding assay. Numerous types of competitive binding assays can be used to determine if a test antibody competes with a reference antibody for binding to a target. Examples of competitive binding assay include, but are not limited to, solid phase direct or indirect radioimmunoassay (RIA), solid phase direct or indirect enzyme immunoassay (EIA), sandwich competition assay, ELISA, solid phase direct biotin-avidin EIA, solid phase direct labeled sandwich assay, solid phase direct label RIA using $1^{125}$ label, and direct labeled RIA. Agents identified by a competitive binding assay (e.g., competing antibodies) include agents that bind the same epitope as the reference antibody and/or agents that bind an adjacent epitope sufficiently proximal to the epitope bound by the reference antibody for steric hindrance to occur, i.e., an overlapping epitope. In some embodiments, a competing agent (e.g., an antibody) will inhibit specific binding of the reference antibody to the target by at least 25%, 30%, 35%, 40%, 45%, 50%, 55%, 60%, 65%, 70% or 75%. In some embodiments, the binding is inhibited by at least 80%, 85%, 90%, 95%, 96%, 97%, 98%, 99% or more.

In some embodiments, an antibody competes for binding to LEAP2 (e.g., human LEAP2) with a reference antibody, wherein the reference antibody comprises: (a) a heavy chain variable region comprising a heavy chain CDR1 comprising GYTFTSYWMH (SEQ ID NO:20), a heavy chain CDR2 comprising AIYPGNSDTSYKQKFKG (SEQ ID NO:21), and a heavy chain CDR3 comprising GKEEYLFAMDY (SEQ ID NO:22); and (b) a light chain variable region comprising a light chain CDR1 comprising KSSQSLLY-SSNQKNYLA (SEQ ID NO:23), a light chain CDR2 comprising WASTRES (SEQ ID NO:24), and a light chain CDR3 comprising QQYYSYPT (SEQ ID NO:25). In some embodiments, an antibody competes for binding to LEAP2 (e.g., human LEAP2) with a reference antibody, wherein the reference antibody comprises a heavy chain variable region comprising SEQ ID NO:7 and a light chain variable region comprising SEQ ID NO:8.

In some embodiments, an antibody competes for binding to LEAP2 (e.g., human LEAP2) with a reference antibody, wherein the reference antibody comprises: (a) a heavy chain variable region comprising a heavy chain CDR1 comprising GYSFTNYYIH (SEQ ID NO:26), a heavy chain CDR2 comprising YIDPFNGGTNYNQKFKG (SEQ ID NO:27), and a heavy chain CDR3 comprising RGYYYGFTY (SEQ ID NO:28); and (b) a light chain variable region comprising a light chain CDR1 comprising KASQSVDYDGDSYMN (SEQ ID NO:29), a light chain CDR2 comprising TASNLES (SEQ ID NO:30), and a light chain CDR3 comprising QQSNEDPYT (SEQ ID NO:31). In some embodiments, an antibody competes for binding to LEAP2 (e.g., human LEAP2) with a reference antibody, wherein the reference antibody comprises a heavy chain variable region comprising SEQ ID NO:9 and a light chain variable region comprising SEQ ID NO:10.

In some embodiments, a LEAP2-binding agent described herein comprises an antibody in which at least one or more of the constant regions has been modified or deleted. In some embodiments, the antibodies may comprise modifications to one or more of the three heavy chain constant regions (CH1, CH2 or CH3) and/or to the light chain constant region (CL). In some embodiments, the heavy chain constant region of the modified antibodies comprises at least one human constant region. In some embodiments, the heavy chain constant region of the modified antibodies comprises more than one human constant region. In some embodiments, modifications to the constant region comprise additions, deletions, or substitutions of one or more amino acids in one or more regions. In some embodiments, one or more regions are partially or entirely deleted from the constant regions of the modified antibodies. In some embodiments, the entire CH2 domain has been removed from an antibody (ΔCH2 constructs). In some embodiments, a deleted constant region is replaced by a short amino acid spacer that provides some of the molecular flexibility typically imparted by the absent constant region. In some embodiments, a modified antibody comprises a CH3 domain directly fused to the hinge region of the antibody. In some embodiments, a modified antibody comprises a peptide spacer inserted between the hinge region and modified CH2 and/or CH3 domains.

It is known in the art that the constant region(s) of an antibody mediates several effector functions and these effector functions can vary depending on the isotype of the antibody. For example, binding of the Cl component of complement to the Fc region of IgG or IgM antibodies (bound to antigen) activates the complement system. Activation of complement is important in the opsonization and lysis of cell pathogens. The activation of complement also stimulates the inflammatory response and can be involved in autoimmune hypersensitivity. In addition, the Fc region of an antibody can bind a cell expressing a Fc receptor (FcR). There are a number of Fc receptors that are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell cytotoxicity or ADCC), release of inflammatory mediators, placental transfer, and control of immunoglobulin production.

In some embodiments, an antibody comprises a variant Fc region. The amino acid sequences of the Fc region of human IgG1, IgG2, IgG3, and IgG4 are known to those of ordinary skill in the art (e.g., representative sequences for human IgG1 and IgG4 are SEQ ID NO:68 and SEQ ID NO:69, respectively). In some cases, Fc regions with amino acid variations have been identified in native antibodies. In some embodiments, a variant Fc region is engineered with a substitution or substitutions at specific amino acid positions as compared to a native Fc region (e.g., SEQ ID NOs:70-71 and 73-77). In some embodiments, a variant Fc region is engineered with a deletion or deletions at specific amino acid positions as compared to a native Fc region. In some embodiments, a variant Fc region is missing the lysine residue at the carboxyl end of the constant region. This variation may be natural or may be engineered (e.g., SEQ ID NO:71, SEQ ID NO:72, SEQ ID NO:77, and SEQ ID NO:78).

In some embodiments, the modified antibodies provide for altered effector functions that, in turn, affect the biological profile of the antibody. For example, in some embodiments, the deletion or inactivation (through point mutations or other means) of a constant region reduces or eliminates Fc receptor binding of the modified antibody as it circulates. In some embodiments, the constant region modifications increase the serum half-life of the antibody. In some embodiments, the constant region modifications reduce the serum half-life of the antibody. In some embodiments, the constant region modifications decrease, reduce, or remove ADCC and/or complement dependent cytotoxicity (CDC) of the antibody. In some embodiments, specific amino acid substitutions in a human IgG1 Fc region with corresponding IgG2 or IgG4 residues may reduce effector functions (e.g., ADCC and CDC) in the modified antibody. In some embodiments, an antibody does not have one or more effector functions. In some embodiments, the antibody has no ADCC activity and/or no CDC activity. In some embodiments, the antibody does not bind an Fc receptor and/or complement factors. In some embodiments, the antibody has no effector function(s) (e.g., "effectorless" antibodies). In some embodiments, the constant region modifications increase or enhance effector functions of the antibody. In some embodiments, the constant region modifications increase or enhance ADCC and/or CDC of the antibody. In some embodiments, the constant region is modified to eliminate disulfide linkages or oligosaccharide moieties. In some embodiments, the constant region is modified to add/substitute one or more amino acids to provide one or more cytotoxin, oligosaccharide, or carbohydrate attachment sites.

Modifications to the constant region of antibodies described herein may be made using well-known biochemical or molecular engineering techniques. In some embodiments, antibody variants are prepared by introducing appropriate nucleotide changes into the encoding DNA, and/or by synthesis of the desired antibody or polypeptide. Using this technique, it may be possible to disrupt the activity or effector function provided by a specific sequence or region while substantially maintaining the structure, binding activity, and other desired characteristics of the modified antibody.

The present disclosure further embraces additional variants and equivalents that are substantially homologous to the recombinant, monoclonal, chimeric, humanized, and human antibodies, or antibody fragments thereof, described herein. In some embodiments, it is desirable to improve the binding affinity of the antibody. In some embodiments, it is desirable to modulate biological properties of the antibody, including but not limited to, specificity, thermostability, expression level, effector function(s), glycosylation, immunogenicity, and/or solubility. Those skilled in the art will appreciate that amino acid changes may alter post-translational processes of an antibody, such as changing the number or position of glycosylation sites or altering membrane anchoring characteristics.

Variations may be a substitution, deletion, or insertion of one or more nucleotides encoding the antibody or polypeptide that results in a change in the amino acid sequence as compared with the native antibody or polypeptide sequence. In some embodiments, amino acid substitutions are the result of replacing one amino acid with another amino acid having similar structural and/or chemical properties, such as the replacement of a leucine with a serine, e.g., conservative amino acid replacements. Insertions or deletions may be in the range of about 1 to 25 amino acids. In some embodiments, the substitution, deletion, or insertion includes less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the parent molecule. In some embodiments, variations in the amino acid sequence that are biologically useful and/or relevant may be determined by systematically making insertions, deletions, or substitutions in the sequence and testing the resulting variant proteins for activity as compared to the parent protein.

In some embodiments, variants may include addition of amino acid residues at the amino- and/or carboxyl-terminal end of the antibody or polypeptide. The length of additional amino acids residues may range from one residue to a hundred or more residues. In some embodiments, a variant comprises an N-terminal methionyl residue. In some embodiments, the variant comprises an additional polypeptide/protein (e.g., Fc region) to create a fusion protein. In some embodiments, a variant is engineered to be detectable and may comprise a detectable label and/or protein (e.g., an enzyme or a fluorescent tag).

In some embodiments, a cysteine residue not involved in maintaining the proper conformation of an antibody is substituted or deleted to modulate the antibody's characteristics, for example, to improve oxidative stability and/or prevent aberrant disulfide crosslinking. Conversely, in some embodiments, one or more cysteine residues are added to create disulfide bond(s) to improve stability.

In some embodiments, an antibody of the present disclosure is "deimmunized". The deimmunization of antibodies generally consists of introducing specific amino acid mutations (e.g., substitutions, deletions, additions) that result in removal of T-cell or B-cell epitopes without significantly reducing the binding affinity or other desired characteristics of the antibody.

The variant antibodies or polypeptides described herein may be generated using methods known in the art, including but not limited to, site-directed mutagenesis, alanine scanning mutagenesis, and PCR mutagenesis.

In some embodiments, a LEAP2-binding agent described herein is chemically modified. In some embodiments, a LEAP2-binding agent is an anti-LEAP2 antibody that has been chemically modified by glycosylation, acetylation, pegylation, phosphorylation, amidation, derivatization by known protecting/blocking groups, proteolytic cleavage, and/or linkage to a cellular ligand or other protein. Any of numerous chemical modifications may be carried out by known techniques.

The present disclosure encompasses LEAP2-binding agents built upon non-immunoglobulin backbones, wherein the agents bind the same epitope or essentially the same epitope as an anti-LEAP2 antibody disclosed herein. In some embodiments, a non-immunoglobulin-based binding agent is an agent that competes with an anti-LEAP2 antibody described herein in a competitive binding assay. In some embodiments, an alternative LEAP2-binding agent comprises a scaffold protein. Generally, scaffold proteins can be assigned to one of three groups based on the architecture of their backbone (1) scaffolds consisting of α-helices; (2) small scaffolds with few secondary structures or an irregular architecture of α-helices and β-sheets; and (3) scaffolds consisting of predominantly β-sheets. Scaffold proteins include, but are not limited to, anticalins, which are based upon the lipocalin scaffold; adnectins, which are based on the $10^{th}$ domain of human fibronectin type 3; affibodies, which are based on the B-domain in the Ig-binding region of *Staphylococcus aureus* protein A; darpins, which are based on ankyrin repeat domain proteins; fynomers, which are based on the SH3 domain of the human Fyn protein kinase; affitins, which are based on Sac7d from *Sulfolobus acidocaldarius*; affilins, which are based on human γ-B-crystallin or human ubiquitin; avimers, which are based on the A-domains of membrane receptor proteins; knottins (cysteine knot miniproteins), which are based upon a stable 30-amino acid anti-parallel β-strand protein fold; and Kunitz domain inhibitor scaffolds, which are based upon a structure that contains three disulfide bonds and three loops.

In some embodiments, a LEAP2-binding agent comprises an engineered scaffold protein comprising a heavy chain CDR1, CDR2, and CDR3 and a light chain CDR1, CDR2, and CDR3 from antibody M1/M2. In some embodiments, a LEAP2-binding agent comprises an engineered scaffold protein comprising a heavy chain CDR1, CDR2, and CDR3 and a light chain CDR1, CDR2, and CDR3 from antibody M18.

Generally speaking, antigen-antibody interactions are non-covalent and reversible, formed by a combination of hydrogen bonds, hydrophobic interactions, electrostatic and van der Waals forces. When describing the strength of an antigen-antibody complex (or other antigen/binding agent complexes), the terms affinity and/or avidity are often used. The binding of an antibody to its antigen is a reversible process, and the affinity of the binding is typically reported as an equilibrium dissociation constant ($K_D$). $K_D$ is the ratio of an antibody dissociation rate ($k_{off}$) (how quickly it dissociates from its antigen) to the antibody association rate ($k_{on}$) (how quickly it binds to its antigen). In some embodiments, $K_D$ values are determined by measuring the $k_{on}$ and $k_{off}$ rates of a specific antibody/antigen interaction and then using a ratio of these values to calculate the $K_D$ value. In some embodiments, $K_D$ values are used to evaluate and rank order the strength of individual antibody/antigen interactions. The lower the $K_D$ of an antibody, the higher the affinity of the antibody for its target. In some embodiments, affinity is measured using SPR technology in a Biacore system. Avidity gives a measure of the overall strength of an antibody-antigen complex. It is dependent on three major parameters: (i) affinity of the antibody for the target, (ii) valency of both the antibody and antigen, and (iii) structural arrangement of the parts that interact.

In some embodiments, a LEAP2-binding agent (e.g., an antibody) binds LEAP2 with a $K_D$ of about 1 μM or less, about 100 nM or less, about 40 nM or less, about 20 nM or less, about 10 nM or less, about 1 nM or less, about 0.1 nM or less, 50 pM or less, 10 pM or less, or 1 pM or less. In some embodiments, a LEAP2-binding agent binds LEAP2 with a $K_D$ of about 20 nM or less. In some embodiments, a LEAP2-binding agent binds LEAP2 with a $K_D$ of about 10 nM or less. In some embodiments, a LEAP2-binding agent binds LEAP2 with a $K_D$ of about 1 nM or less. In some embodiments, a LEAP2-binding agent binds LEAP2 with a $K_D$ of about 0.5 nM or less. In some embodiments, a LEAP2-binding agent binds LEAP2 with a $K_D$ of about 0.1 nM or less. In some embodiments, a LEAP2-binding agent binds LEAP2 with a $K_D$ of about 50 pM or less. In some embodiments, a LEAP2-binding agent binds LEAP2 with a $K_D$ of about 25 pM or less. In some embodiments, a LEAP2-binding agent binds LEAP2 with a $K_D$ of about 10 pM or less. In some embodiments, a LEAP2-binding agent binds LEAP2 with a $K_D$ of about 1 pM or less. In some embodiments, the dissociation constant of the binding agent (e.g., an antibody) to LEAP2 is the dissociation constant determined using a LEAP2 protein or a fragment thereof immobilized on a Biacore chip with the binding agent flowed over the chip. In some embodiments, the dissociation constant of the binding agent (e.g., an antibody) for LEAP2 is the dissociation constant determined using the binding agent captured by an anti-human IgG antibody on a Biacore chip with soluble LEAP2 flowed over the chip.

In some embodiments, the LEAP2-binding agent (e.g., an antibody) binds LEAP2 with a half maximal effective concentration (EC50) of about 1 μM or less, about 100 nM or less, about 40 nM or less, about 20 nM or less, about 10 nM or less, about 1 nM or less, or about 0.1 nM or less. In some embodiments, a LEAP2-binding agent binds to human LEAP2 with an EC50 of about 1 μM or less, about 100 nM or less, about 40 nM or less, about 20 nM or less, about 10 nM or less, about 1 nM or less, or about 0.1 nM or less. In some embodiments, a LEAP2-binding agent binds cyno LEAP2 and/or human LEAP2 with an EC50 of about 40 nM or less, about 20 nM or less, about 10 nM or less, about 1 nM or less or about 0.1 nM or less.

The LEAP2-binding agents (e.g., antibodies) described herein can be produced by any suitable method known in the art. Such methods range from direct protein synthesis methods to constructing a DNA sequence encoding polypeptide sequences and expressing those sequences in a suitable host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional variants thereof. In some embodiments, a DNA sequence encoding a polypeptide of interest is constructed by chemical synthesis using an oligonucleotide synthesizer. Oligonucleotides can be designed based on the amino acid sequence of the desired polypeptide and selecting those codons that are favored in the host cell in which the recombinant polypeptide of interest will be produced. Standard methods can be applied to synthesize a polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis, or another method), the polynucleotide sequences encoding a particular polypeptide of interest can be inserted into an expression vector and operatively linked to an expression control sequence appropriate for expression of the protein in a desired host. Proper assembly can be confirmed by nucleotide sequencing, restriction enzyme mapping, and/or expression of a biologically active polypeptide in a suitable host. As is well-known in the art, in order to obtain high expression levels of a transfected gene in a host, the gene must be operatively linked to transcriptional and translational expression control sequences that are functional in the chosen expression host.

In some embodiments, recombinant expression vectors are used to amplify and express DNA encoding antibodies against human LEAP2. For example, recombinant expression vectors can be replicable DNA constructs that have synthetic or cDNA-derived DNA fragments encoding a polypeptide chain of a LEAP2-binding agent, such as an anti-LEAP2 antibody operatively linked to suitable transcriptional and/or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence that is transcribed into mRNA and translated into protein, and (3) appropriate transcription and translation initiation and termination sequences. Regulatory elements can include an operator sequence to control transcription. The ability to replicate in a host, usually conferred by an origin of replication, and a selection gene to facilitate recognition of transformants can also be included. DNA regions are "operatively linked" when they are functionally related to each other. For example, DNA for a signal peptide (secretory leader) is operatively linked to DNA for a polypeptide if it is expressed as a precursor that participates in the secretion of the polypeptide; a promoter is operatively linked to a coding sequence if it controls the transcription of the sequence; or a ribosome binding site is operatively linked to a coding sequence if it is positioned so as to permit translation. In some embodiments, structural elements intended for use in yeast expression systems include a leader sequence enabling extracellular secretion of translated protein by a host cell. In some embodiments, in situations where recombinant protein is expressed without a leader or transport sequence, a polypeptide may include an N-terminal methionine residue. This residue can optionally be subsequently cleaved from the expressed recombinant protein to provide a final product.

The choice of an expression control sequence and an expression vector generally depends upon the choice of host. A wide variety of expression host/vector combinations can be employed. Useful expression vectors for eukaryotic hosts include, for example, vectors comprising expression control sequences from SV40, bovine papilloma virus, adenovirus, and cytomegalovirus. Useful expression vectors for bacterial hosts include known bacterial plasmids, such as plasmids from *E. coli*, including pCR1, pBR322, pMB9 and their derivatives, and wider host range plasmids, such as M13 and other filamentous single-stranded DNA phages.

In some embodiments, a LEAP2-binding agent (e.g., an antibody) of the present disclosure is expressed from one or more vectors. In some embodiments, a heavy chain polypeptide is expressed by one vector and a light chain polypeptide is expressed by a second vector. In some embodiments, a heavy chain polypeptide and a light chain polypeptide are expressed by one vector.

Suitable host cells for expression of a LEAP2-binding agent (e.g., an antibody) or a LEAP2 protein or fragment thereof to use as an antigen or immunogen include prokaryotes, yeast cells, insect cells, or higher eukaryotic cells under the control of appropriate promoters. Prokaryotes include gram-negative or gram-positive organisms, for example *E. coli* or *Bacillus*. Higher eukaryotic cells include established cell lines of mammalian origin as described herein. Cell-free translation systems may also be employed. Appropriate cloning and expression vectors for use with bacterial, fungal, yeast, and mammalian cellular hosts, as well as methods of protein production, including antibody production are well-known in the art.

Various mammalian culture systems may be used to express recombinant polypeptides. Expression of recombinant proteins in mammalian cells may be desirable because these proteins are generally correctly folded, appropriately modified, and biologically functional. Examples of suitable mammalian host cell lines include, but are not limited to, COS-7 (monkey kidney-derived), L-929 (murine fibroblast-derived), C127 (murine mammary tumor-derived), 3T3 (murine fibroblast-derived), CHO (Chinese hamster ovary-derived), HeLa (human cervical cancer-derived), BHK (hamster kidney fibroblast-derived), HEK-293 (human embryonic kidney-derived) cell lines and variants thereof. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences.

Expression of recombinant proteins in insect cell culture systems (e.g., baculovirus) also offers a robust method for producing correctly folded and biologically functional proteins. Baculovirus systems for production of heterologous proteins in insect cells are well-known to those of skill in the art.

Thus, the present disclosure provides cells comprising the LEAP2-binding agents described herein. In some embodiments, the cells produce the LEAP2-binding agents described herein. In some embodiments, the cells produce an antibody. In some embodiments, the cells produce an antibody that binds human LEAP2. In some embodiments, the cells produce an antibody that binds mouse LEAP2. In some embodiments, the cells produce an antibody that binds monkey (e.g., cyno) LEAP2. In some embodiments, the cells produce an antibody that binds human LEAP2 and monkey LEAP2. In some embodiments, the cells produce an antibody designated M1/M2. In some embodiments, the cells produce a humanized version of antibody M1/M2, referred to as HzM1/M2. In some embodiments, the cells produce an antibody designated M18. In some embodiments, the cells produce a humanized version of antibody designated M18, referred to as HzM18. In some embodiments, the cell is a prokaryotic cell (e.g., *E. coli*). In some embodiments, the cell is an eukaryotic cell. In some embodiments, the cell is a mammalian cell. In some embodiments, the cell is a hybridoma cell.

Proteins produced by a host cell can be purified according to any suitable method. Standard methods include chromatography (e.g., ion exchange, affinity, and sizing column chromatography), centrifugation, differential solubility, or by any other standard technique for protein purification. Affinity tags such as hexa-histidine, maltose binding domain, influenza coat sequence, and glutathione-S-transferase can be attached to the protein to allow easy purification by passage over an appropriate affinity column Affinity chromatography used for purifying immunoglobulins include, but are not limited to, Protein A, Protein G, and Protein L chromatography. Isolated proteins can be physically characterized using techniques known to those of skill in the art, including but not limited to, proteolysis, size exclusion chromatography (SEC), mass spectrometry (MS), nuclear magnetic resonance (NMR), isoelectric focusing (IEF), high performance liquid chromatography (HPLC), and x-ray crystallography. The purity of isolated proteins can be determined using techniques known to those of skill in the art, including but not limited to, SDS-PAGE, SEC, capillary gel electrophoresis, IEF, and capillary isoelectric focusing (cIEF).

In some embodiments, supernatants from expression systems that secrete recombinant protein into culture media are first concentrated using a commercially available protein concentration filter, for example, an Amicon® or Millipore Pellicon® ultrafiltration unit. Following the concentration step, the concentrate can be applied to a suitable purification matrix. In some embodiments, an anion exchange resin is employed, for example, a matrix or substrate having pendant diethylaminoethyl (DEAE) groups. The matrices can be acrylamide, agarose, dextran, cellulose, or other types commonly employed in protein purification. In some embodiments, a cation exchange step is employed. Suitable cation exchangers include various insoluble matrices comprising sulfopropyl or carboxymethyl groups. In some embodiments, a hydroxyapatite media is employed, including but not limited to, ceramic hydroxyapatite (CHT). In some embodiments, one or more reverse-phase HPLC steps employing hydrophobic RP-HPLC media, e.g., silica gel having pendant methyl or other aliphatic groups, are employed to further purify a recombinant protein. In some embodiments, hydrophobic interaction chromatography (HIC) is used to separate recombinant proteins based on their hydrophobicity. HIC is a useful separation technique for purifying proteins while maintaining biological activity due to the use of conditions and matrices that operate under less denaturing conditions than some other techniques. Some or all of the foregoing purification steps, in various combinations, can be employed to provide a homogeneous recombinant protein.

LEAP2-binding agents (e.g., antibodies) of the present disclosure may be analyzed for their physical/chemical properties and/or biological activities by various methods known in the art. In some embodiments, an anti-LEAP2 antibody is tested for its ability to bind LEAP2 (e.g., human LEAP2). Binding assays include, but are not limited to, SPR (e.g., Biacore), ELISA, and FACS. In some embodiments, an anti-LEAP2 antibody is tested for its ability to inhibit, reduce, or block binding of LEAP2 to GHSR. In some embodiments, an anti-LEAP2 antibody is tested for its ability to inhibit, reduce, or block LEAP2 inhibition of gherlin-induced activity. In some embodiments, an anti-LEAP2 antibody is tested for its ability to inhibit, reduce, or block LEAP2 inhibition of GHSR activity. In some embodiments, an anti-LEAP2 antibody is tested for its ability to enhance or increase gherlin-induced GHSR activity. In some embodiments, an anti-LEAP2 antibody is tested for its ability to enhance or increase GHSR activity. In addition, antibodies may be evaluated for solubility, stability, thermostability, viscosity, expression levels, expression quality, and/or purification efficiency.

In some embodiments, monoclonal antibodies generated against LEAP2 are grouped based upon the epitope each individual antibody recognizes, a process known as "epitope binning" Generally, antibodies are tested in a pairwise combinatorial manner and antibodies that compete with each other are grouped together into bins. For example, in a premix binning assay, a first antibody is immobilized on a surface and a premixed solution of the second antibody and antigen is flowed over the immobilized first antibody. In parallel, the target protein is immobilized on a surface and the two antibodies are flowed over the immobilized antigen and compete to bind to the target. From this technique, antibodies that block one another can be identified. A competitive blocking profile is created for each antibody relative to the others. The results determine which bin each antibody is placed in. High-throughput methods of epitope binning are known in the art and allow for screening and characterization of large numbers of antibodies. Antibodies that bind similar epitopes often share a similar function. Conversely, antibodies that bind different epitopes may have different functional activities.

Epitope mapping is the process of identifying the binding site, or epitope on a target protein where an antibody (or other binding agent) binds. A variety of methods are known in the art for mapping epitopes on target proteins. These methods include mutagenesis (e.g., shotgun mutagenesis, site-directed mutagenesis, and alanine scanning); domain or fragment scanning; peptide scanning (e.g., Pepscan technology); display methods (e.g., phage display, microbial display, and ribosome/mRNA display); methods involving proteolysis and mass spectroscopy; and structural determination (e.g., X-ray crystallography and NMR).

In some embodiments, LEAP2-binding agents (e.g., antibodies) described herein are characterized by assays including, but not limited to, N-terminal sequencing, amino acid analysis, HPLC, mass spectrometry, ion exchange chromatography, and papain digestion.

In some embodiments, assays are provided for identifying a LEAP2-binding agent (e.g., antibody) that affects GHSR activity. In some embodiments, assays are provided for identifying a LEAP2-binding agent (e.g., antibody) that affects ghrelin-induced GHSR activity. In some embodiments, a PathHunter® U2OS GHSR β-arrestin cell line is used to assess GHSR activity. In some embodiments, SPR, ELISA, or FACS assays are used to assess the ability of a LEAP2-binding agent to block binding of LEAP2 to GHSR.

In some embodiments, a LEAP2-binding agent (e.g., an antibody) described herein is an antagonist of LEAP2. In some embodiments, a LEAP2-binding agent (e.g., an antibody) described herein is an agonist of GHSR. In some embodiments, a LEAP2-binding agent induces, enhances, and/or increases GHSR activity. The terms "induces," "enhances," and "increases" are used herein interchangeably to refer to a significant change in GHSR activity. In certain embodiments, the LEAP2-binding agent induces, enhances, and/or increases GHSR activity by at least about 10%, at least about 20%, at least about 30%, at least about 50%, at least about 75%, at least about 90%, or about 100%. In some embodiments, a LEAP2-binding agent that induces, enhances, and/or increases GHSR activity is antibody M1/M2, a humanized version of antibody M1/M2, or a variant thereof. In some embodiments, a LEAP2-binding agent that induces, enhances, and/or increases GHSR activity is antibody M18, a humanized version of antibody M18, or a variant thereof. In some embodiments, a LEAP2-binding agent induces, enhances, and/or increases ghrelin-induced GHSR activity. In certain embodiments, the LEAP2-binding agent induces, enhances, and/or increases ghrelin-induced GHSR activity by at least about 10%, at least about 20%, at least about 30%, at least about 50%, at least about 75%, at least about 90%, or about 100%. In some embodiments, a LEAP2-binding agent that induces, enhances, and/or increases ghrelin-induced GHSR activity is antibody M1/M2, a humanized version of antibody M1/M2, or a variant thereof. In some embodiments, a LEAP2-binding agent that induces, enhances, and/or increases ghrelin-induced GHSR activity is antibody M18, a humanized version of antibody M18, or a variant thereof.

The present disclosure also provides conjugates comprising a LEAP2-binding agent (e.g., an antibody) described herein. In some embodiments, an anti-LEAP2 antibody is attached to a second molecule or moiety. In some embodiments, an anti-LEAP2 antibody is conjugated to a molecule or agent to form an ADC (antibody-drug conjugate).

Conjugates comprising a LEAP2-binding agent (e.g., an antibody) described herein may be made using any suitable method known in the art. In some embodiments, conjugates are made using a variety of bifunctional protein-coupling agents such as N-succinimidyl-3-(2-pyridyidithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

In some embodiments, a LEAP2-binding agent (e.g., an antibody) described herein is conjugated to a detectable substance or molecule that allows the agent to be used for diagnosis and/or detection. A detectable substance can include, but is not limited to, enzymes, such as horseradish peroxidase, alkaline phosphatase, beta-galactosidase, and acetylcholinesterase; prosthetic groups, such as biotin and flavine(s); fluorescent materials, such as, umbelliferone, fluorescein, fluorescein isothiocyanate (FITC), rhodamine, tetramethylrhodamine isothiocyanate (TRITC), dichlorotriazinylamine fluorescein, dansyl chloride, cyanine (Cy3), phycoerythrin, and green fluorescent protein (GFP); bioluminescent materials, such as luciferase; radioactive materials, such as $^{212}$Bi, $^{14}$C, $^{57}$Co, $^{51}$Cr, $^{67}$Cu, $^{18}$F, $^{68}$Ga, $^{67}$Ga, $^{153}$Gd, $^{159}$Gd, $^{68}$Ge, $^{3}$H, $^{166}$Ho, $^{131}$I, $^{125}$I, $^{123}$I, $^{121}$I, $^{115}$In, $^{113}$In, $^{112}$In, $^{111}$In, $^{140}$La, $^{177}$Lu, $^{54}$Mn, $^{99}$Mo, $^{32}$P, $^{103}$Pd, $^{149}$Pm, $^{142}$Pr, $^{186}$Re, $^{188}$Re, $^{105}$Rh, $^{97}$Ru, $^{35}$S, $^{47}$Sc, $^{75}$Se, $^{153}$Sm, $^{113}$Sn, $^{117}$Sn, $_{85}$Sr, $^{99m}$Tc, $^{201}$Ti, $^{133}$Xe, $^{90}$Y, $^{69}$Yb, $^{175}$Yb, $^{65}$Zn; positron emitting metals; and metal ions.

In some embodiments, a LEAP2-binding agent (e.g., an antibody) described herein is linked to (either covalently or non-covalently) a "tag" or "marker" that allows the agent to be used for diagnosis, detection, and/or purification. Tags known to those of skill in the art include, but are not limited to, glutathione-S-transferase (GST), hemagglutinin (HA), FLAG™, His-tag®, and c-myc.

An anti-LEAP2 antibody described herein can also be conjugated to a second antibody to form an antibody heteroconjugate.

A LEAP2-binding agent (e.g., an antibody) described herein may be attached to a solid support. Such solid supports include, but are not limited to, glass, cellulose, polyacrylamide, nylon, polystyrene, polyvinyl chloride, or polypropylene. In some embodiments, immobilized anti-LEAP2 antibodies are used in immunoassays. In some embodiments, immobilized anti-LEAP2 antibodies are used in purification of the target antigen (e.g., human LEAP2).

III. Polynucleotides

In some embodiments, the disclosure encompasses polynucleotides comprising polynucleotides that encode a polypeptide (e.g., LEAP2 or a variant thereof or a LEAP2-binding agent) described herein. The term "polynucleotides that encode a polypeptide" encompasses a polynucleotide which includes only coding sequences for the polypeptide as well as a polynucleotide which includes additional coding and/or non-coding sequences. The polynucleotides of the disclosure can be in the form of RNA or in the form of DNA. DNA includes cDNA, genomic DNA, and synthetic DNA; and can be double-stranded or single-stranded, and if single stranded can be the coding strand or non-coding (anti-sense) strand.

In some embodiments, the polynucleotide comprises a polynucleotide (e.g., a nucleotide sequence) encoding a polypeptide comprising an amino acid sequence selected from the group consisting of: SEQ ID NOs:1, 2, and 7-19. In some embodiments, the polynucleotide comprises a polynucleotide encoding a polypeptide comprising an amino acid sequence of SEQ ID NO:1. In some embodiments, the polynucleotide comprises a polynucleotide encoding a polypeptide comprising an amino acid sequence of SEQ ID NO:2. In some embodiments, the polynucleotide comprises a polynucleotide encoding a polypeptide comprising an amino acid sequence of SEQ ID NO:7. In some embodiments, the polynucleotide comprises a polynucleotide encoding a polypeptide comprising an amino acid sequence of SEQ ID NO:8. In some embodiments, the polynucleotide comprises a polynucleotide encoding a polypeptide comprising an amino acid sequence of SEQ ID NO:9. In some embodiments, the polynucleotide comprises a polynucleotide encoding a polypeptide comprising an amino acid sequence of SEQ ID NO:10. In some embodiments, the polynucleotide comprises a polynucleotide (e.g., a nucleotide sequence) encoding a polypeptide comprising more than one amino acid sequence selected from the group consisting of: SEQ ID NOs:7-10. In some embodiments, the polynucleotide comprises a polynucleotide encoding (i) a polypeptide comprising an amino acid sequence of SEQ ID NO:7 and (ii) a polypeptide comprising an amino acid sequence of SEQ ID NO:8. In some embodiments, the polynucleotide comprises a polynucleotide encoding (i) a polypeptide comprising an amino acid sequence of SEQ ID NO:9 and (ii) a polypeptide comprising an amino acid sequence of SEQ ID NO:10.

In some embodiments, a polynucleotide comprises a polynucleotide having a nucleotide sequence at least about 80% identical, at least about 85% identical, at least about 90% identical, at least about 95% identical, and in some embodiments, at least about 96%, 97%, 98%, or 99% identical to a polynucleotide encoding an amino acid sequence selected from the group consisting of: SEQ ID NOs:1, 2, and 7-19. Also provided is a polynucleotide that comprises a polynucleotide that hybridizes to a polynucleotide encoding an amino acid sequence selected from the group consisting of: SEQ ID NOs:1, 2, and 7-19. In some embodiments, the hybridization is under conditions of high stringency as is known to those skilled in the art.

In some embodiments, a polynucleotide comprises the coding sequence for a polypeptide that is a proprotein or propeptide (e.g., a sequence that is modified, such as cleaved, to produce a mature peptide).

In some embodiments, a polynucleotide comprises the coding sequence for a polypeptide (e.g., a peptide or an antibody) fused in the same reading frame to a polynucleotide that aids in expression and secretion of a polypeptide from a host cell (e.g., a leader sequence that functions as a secretory sequence for controlling transport of a polypeptide). The polypeptide can have the leader sequence cleaved by the host cell to form a "mature" form of the polypeptide.

In some embodiments, a polynucleotide comprises the coding sequence for a polypeptide (e.g., a peptide or an antibody) fused in the same reading frame to a marker or tag sequence. For example, in some embodiments, a marker sequence is a hexa-histidine tag (HIS-tag®) that allows for efficient purification of the polypeptide fused to the marker. In some embodiments, a marker sequence is a hemagglutinin (HA) tag derived from the influenza hemagglutinin protein when a mammalian host (e.g., COS-7 cells) is used. In some embodiments, the marker sequence is a FLAG™ tag. In some embodiments, a marker may be used in conjunction with other markers or tags.

The present disclosure also provides variants of the polynucleotides described herein, wherein the variant encodes, for example, fragments, analogs, and/or derivatives of a polypeptide. In some embodiments, the present disclosure provides a polynucleotide comprising a polynucleotide having a nucleotide sequence at least about 80% identical, at least about 85% identical, at least about 90% identical, at least about 95% identical, and in some embodiments, at least about 96%, 97%, 98% or 99% identical to a polynucleotide sequence encoding a polypeptide described herein.

As used herein, the phrase "a polynucleotide having a nucleotide sequence at least about 95% identical to a polynucleotide sequence" is intended to mean that the nucleotide sequence of the polynucleotide is identical to a reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

The polynucleotide variants can contain alterations in the coding regions, non-coding regions, or both. In some embodiments, a polynucleotide variant contains alterations that produce silent substitutions, additions, or deletions, but does not alter the properties or activities of the encoded polypeptide. In some embodiments, a polynucleotide variant comprises silent substitutions that result in no change to the amino acid sequence of the polypeptide (due to the degeneracy of the genetic code). Polynucleotide variants can be produced for a variety of reasons, for example, to optimize codon expression for a particular host (e.g., change codons in the human mRNA to those preferred by a bacterial host such as $E.\ coli$). In some embodiments, a polynucleotide variant comprises at least one silent mutation in a non-coding or a coding region of the sequence.

In some embodiments, a polynucleotide variant is produced to modulate or alter expression (or expression levels) of the encoded polypeptide. In some embodiments, a polynucleotide variant is produced to increase expression of the encoded polypeptide. In some embodiments, a polynucleotide variant is produced to decrease expression of the encoded polypeptide. In some embodiments, a polynucleotide variant has increased expression of the encoded polypeptide as compared to a parental polynucleotide sequence. In some embodiments, a polynucleotide variant has decreased expression of the encoded polypeptide as compared to a parental polynucleotide sequence.

In some embodiments, a polynucleotide is isolated. In some embodiments, a polynucleotide is substantially pure.

Vectors and cells comprising the polynucleotides described herein are also provided. In some embodiments, an expression vector comprises a polynucleotide molecule encoding a LEAP2 peptide or variant thereof described herein. In some embodiments, an expression vector comprises a polynucleotide molecule encoding a polypeptide that is part of a LEAP2 peptide or variant thereof described herein. In some embodiments, a host cell comprises an expression vector comprising a polynucleotide molecule encoding a LEAP2 peptide or variant thereof described herein. In some embodiments, a host cell comprises an expression vector comprising a polynucleotide molecule encoding a polypeptide that is part of a LEAP2 peptide or variant thereof described herein. In some embodiments, a host cell comprises a polynucleotide molecule encoding a LEAP2 peptide or variant thereof described herein.

In some embodiments, an expression vector comprises a polynucleotide molecule encoding a LEAP2-binding agent described herein. In some embodiments, an expression vector comprises a polynucleotide molecule encoding a polypeptide that is part of a LEAP2-binding agent described herein. In some embodiments, a host cell comprises an expression vector comprising a polynucleotide molecule encoding a LEAP2-binding agent described herein. In some embodiments, a host cell comprises an expression vector comprising a polynucleotide molecule encoding a polypeptide that is part of a LEAP2-binding agent described herein. In some embodiments, a host cell comprises a polynucleotide molecule encoding a LEAP2-binding agent described herein.

IV. Methods of Use and Pharmaceutical Compositions

A binding agent (e.g., LEAP2 or variant thereof or an anti-LEAP2 antibody) of the present disclosure may be used in, for example, in vitro, ex vivo, and in vivo therapeutic methods. In some embodiments, the present disclosure provides methods, either in vivo or in vitro, comprising exposing a cell to a LEAP2-binding agent (e.g., an anti-LEAP2 antibody) or a GHSR-binding agent (e.g., LEAP2 or variant thereof).

The binding agents (e.g., peptides or antibodies) described herein are useful in a variety of applications including, but not limited to, therapeutic treatment of a variety of syndromes, disorders, and/or diseases. In some embodiments, a method is provided for treating a disease, disorder or condition in a subject, wherein the method comprises administering to the subject a therapeutically effective amount of LEAP2 or a variant thereof described herein. In certain embodiments, a method for treating a disease, disorder, or condition in a subject comprises administering to a subject a therapeutically effective amount of a pharmaceutical formulation comprising LEAP2 or a variant thereof described herein. In some embodiments, a method is provided for treating a disease, disorder or condition in a subject, wherein the method comprises administering to the subject a therapeutically effective amount of an anti-LEAP2 antibody described herein. In certain embodiments, a method for treating a disease, disorder, or condition in a subject comprises administering to a subject a therapeutically effective amount of a pharmaceutical formulation comprising an anti-LEAP2 antibody described herein. In some embodiments, a method comprises administration of at least one additional therapeutic agent.

In some embodiments, a binding agent (e.g., a peptide or an antibody) described herein is administered to a human for therapeutic purposes. In some embodiments, a binding agent described herein is administered to a non-human mammal (e.g., a primate, dog, cat, pig, rat, or mouse). In some embodiments, a binding agent is administered to a non-human mammal for veterinary purposes or for testing in an animal model of human disease. In some embodiments, animal models are useful for evaluating the therapeutic efficacy of a binding agent (e.g., an antibody or peptide) described herein (e.g., studying pharmacokinetics, testing of dosages, and/or time courses of administration).

In some embodiments, a binding agent (e.g., LEAP2 or a variant thereof) described herein is useful in methods for inhibiting or reducing ghrelin activity. In some embodiments, a method of inhibiting or reducing ghrelin activity in a subject comprises administering to the subject a therapeutically effective amount of a binding agent (e.g., LEAP2 or a variant thereof) described herein. In some embodiments, a binding agent (e.g., LEAP2 or a variant thereof) described herein is useful in methods of inhibiting, reducing, or blocking GHSR activity. The terms "inhibiting," "reducing," and "blocking" in the context of an activity of a protein are used herein interchangeably to refer to a negative change in the activity of the protein. In some embodiments, a method of inhibiting, reducing, or blocking GHSR activity in a subject comprises administering to the subject a therapeutically effective amount of a binding agent (e.g., LEAP2 or a variant thereof) described herein. In some embodiments, the GHSR activity is mediated or induced by ghrelin. In some embodiments, a binding agent (e.g., LEAP2 or a variant thereof) described herein is useful in methods of inhibiting, reducing, or blocking ghrelin-induced growth hormone release. In some embodiments, a method of inhibiting, reducing, or blocking ghrelin-induced growth hormone release in a subject comprises administering to the subject a therapeutically effective amount of a binding agent (e.g., LEAP2 or a variant thereof) described herein. In some embodiments, a binding agent (e.g., LEAP2 or a variant thereof) described herein is useful in methods of suppressing appetite and/or reducing food intake. In some embodiments, a method of suppressing appetite in a subject comprises administering to the subject a therapeutically effective amount of a binding agent (e.g., LEAP2 or a variant thereof) described herein. In some embodiments, a method of reducing food intake in a subject comprises administering to the subject a therapeutically effective amount of a binding agent (e.g., LEAP2 or a variant thereof) described herein. In some embodiments, a binding agent (e.g., LEAP2 or a variant thereof) described herein is useful in methods for weight loss. In some embodiments, a method for weight loss in a subject comprises administering to the subject a therapeutically effective amount of a binding agent (e.g., LEAP2 or a variant thereof) described herein. In some embodiments, the subject is obese, diabetic, has hyperglycemia, acromegaly, gigantism, and/or Prader-Willi syndrome.

In some embodiments, a binding agent (e.g., LEAP2 or a variant thereof) described herein is useful in methods of treating a neuroendocrine and/or metabolic disease. In some embodiments, a method of treating a neuroendocrine disease in a subject comprises administering to the subject a therapeutically effective amount of a binding agent (e.g., LEAP2 or a variant thereof) described herein. In some embodiments, a method of treating a metabolic disease in a subject comprises administering to the subject a therapeutically effective amount of a binding agent (e.g., LEAP2 or a variant thereof) described herein. In some embodiments, the neuroendocrine and/or metabolic disease is obesity, diabetes, acromegaly, gigantism, or Prader-Willi syndrome. In some embodiments, the neuroendocrine disease is acromegaly or gigantism. In some embodiments, the metabolic disease is obesity. In some embodiments, the metabolic disease is Prader-Willi syndrome. In some embodiments, the neuroendocrine and/or metabolic disease is diabetes. In some embodiments, the diabetes is Type 1 diabetes. In some embodiments, the diabetes is Type 2 diabetes.

In some embodiments, a binding agent (e.g., LEAP2 or a variant thereof) described herein is useful in methods of treating obesity. In some embodiments, a method of treating obesity in a subject comprises administering to the subject a therapeutically effective amount of a binding agent (e.g., LEAP2 or a variant thereof) described herein.

In some embodiments, a binding agent (e.g., LEAP2 or a variant thereof) described herein is useful in methods of treating diabetes. In some embodiments, a method of treating diabetes in a subject comprises administering to the subject a therapeutically effective amount of a binding agent (e.g., LEAP2 or a variant thereof) described herein. In some embodiments, the diabetes is Type 1 diabetes. Type 1 diabetes is an autoimmune disease condition characterized by high blood glucose levels resulting from a loss of pancreatic beta cell mass and/or function and a loss of insulin production. Type 1 diabetes symptoms are generally the result of hyperglycemia and a breakdown of body fat. Symptoms include, but are not limited to, excessive thirst (polydipsia), frequent urination (polyuria), extreme hunger (polyphagia), extreme fatigue, weight loss, and ketones present in their urine. In some embodiments, the Type 1 diabetes is latent autoimmune diabetes of adults (LADA).

In some embodiments, the diabetes is Type 2 diabetes. Generally, Type 2 diabetes results from insulin resistance and/or reduced insulin secretion. Symptoms of Type 2 diabetes include, but are not limited to, hyperglycemia, fatigue, dry or itchy skin, blurred vision, increased thirst, frequent urination, slow healing cuts or sores, high rate of infections, and numbness or tingling in the feet. If left untreated, more serious symptoms can result, including severe hyperglycemia (e.g., glucose levels over 600 mg/dL), lethargy, confusion, shock, and/or a hyperosmolar hyperglycemic nonketotic coma.

In some embodiments, a binding agent (e.g., LEAP2 or a variant thereof) described herein is useful in methods of treating hyperglycemia. In some embodiments, a method of treating hyperglycemia in a subject comprises administering to the subject a therapeutically effective amount of a binding agent (e.g., LEAP2 or a variant thereof) described herein. As used herein, the term "hyperglycemia" or "hyperglycemic" refers to a transient or chronic abnormally high level of glucose present in the blood of a subject. The hyperglycemia may be caused by a delay in glucose metabolism or absorption such that the subject exhibits glucose intolerance or a state of elevated glucose not typically found in normal subjects. Fasting blood glucose levels are considered to be in a "normal" range at less than about 100 mg/dL, for impaired glucose metabolism, between about 100 and 126 mg/dL, and for diabetics greater than about 126 mg/dL.

In some embodiments, a binding agent (e.g., LEAP2 or a variant thereof) described herein is useful in methods for reducing or lowering blood glucose levels. In some embodiments, a method of reducing or lowering blood glucose levels in a subject comprises administering to the subject a therapeutically effective amount of a binding agent (e.g., LEAP2 or a variant thereof) described herein. In some embodiments, a binding agent (e.g., LEAP2 or a variant thereof) described herein is useful in methods for reducing or lowering growth hormone levels. In some embodiments, a method of reducing or lowering growth hormone levels in a subject comprises administering to the subject a therapeutically effective amount of a binding agent (e.g., LEAP2 or a variant thereof) described herein.

In some embodiments of the methods described herein, the binding agent comprises amino acids 38-77 of SEQ ID NO:1. In some embodiments of the methods described herein, the binding agent comprises SEQ ID NO:2. In some embodiments of the methods described herein, the binding agent consists of SEQ ID NO:2. In some embodiments of the methods described herein, the binding agent comprises a variant of SEQ ID NO:2. In some embodiments of the methods described herein, the binding agent comprises SEQ ID NO:2 and a heterologous polypeptide. In some embodiments of the methods described herein, the binding agent comprises a variant of SEQ ID NO:2 and a heterologous polypeptide.

In some embodiments, a binding agent (e.g., an anti-LEAP2 antibody) described herein is useful in methods of increasing, enhancing, and/or promoting ghrelin activity. In some embodiments, a method of increasing, enhancing, and/or promoting ghrelin activity in a subject comprises administering to the subject a therapeutically effective amount of a binding agent (e.g., an anti-LEAP2 antibody) described herein. In some embodiments, a binding agent (e.g., an anti-LEAP2 antibody) described herein is useful in methods for increasing, enhancing, and/or promoting GHSR activity. In some embodiments, a method of increasing, enhancing, and/or promoting GHSR activity in a subject comprises administering to the subject a therapeutically effective amount of a binding agent (e.g., an anti-LEAP2 antibody) described herein. In some embodiments, the GHSR activity is mediated or induced by ghrelin. In some embodiments, a binding agent (e.g., an anti-LEAP2 antibody) described herein is useful in methods of increasing, enhancing, and/or promoting ghrelin-induced growth hormone release. In some embodiments, a method of increasing, enhancing, and/or promoting ghrelin-induced growth hormone release in a subject comprises administering to the subject a therapeutically effective amount of a binding agent (e.g., an anti-LEAP2 antibody) described herein. The terms "increasing," "enhancing," and "promoting" in the context of an activity of a protein are used herein interchangeably to refer to a positive change in the activity of the protein. In some embodiments, a binding agent (e.g., an anti-LEAP2 antibody) described herein is useful in methods of stimulating appetite and/or increasing food intake. In some embodiments, a method of stimulating appetite in a subject comprises administering to the subject a therapeutically effective amount of a binding agent (e.g., an anti-LEAP2 antibody) described herein. In some embodiments, a method of increasing food intake in a subject comprises administering to the subject a therapeutically effective amount of a binding agent (e.g., an anti-LEAP2 antibody) described herein. In some embodiments, a binding agent (e.g., an anti-LEAP2 antibody) described herein is useful in methods of weight gain. In some embodiments, a method of weight gain in a subject comprises administering to the subject a therapeutically effective amount of a binding agent (e.g., an anti-LEAP2 antibody) described herein. In certain embodiments, the subject may have a neuroendocrine and/or metabolic disease such as cachexia, anorexia, and/or other wasting syndromes.

In some embodiments, a binding agent (e.g., an anti-LEAP2 antibody) described herein is useful in methods of treating a neuroendocrine and/or metabolic disease. In some embodiments, a method of treating a neuroendocrine disease in a subject comprises administering to the subject a therapeutically effective amount of a binding agent (e.g., an anti-LEAP2 antibody) described herein. In some embodiments, a method of treating a metabolic disease in a subject comprises administering to the subject a therapeutically effective amount of a binding agent (e.g., an anti-LEAP2 antibody) described herein. In some embodiments, the neuroendocrine and/or metabolic disease is cachexia, anorexia, or other wasting syndromes. In some embodiments, a binding agent (e.g., an anti-LEAP2 antibody) described herein is useful in methods of treating cachexia. In some embodiments, a method of treating cachexia in a subject comprises administering to the subject a therapeutically effective amount of a binding agent (e.g., an anti-LEAP2 antibody) described herein. In some embodiments, the cachexia is cancer cachexia. In some embodiments, a binding agent (e.g., an anti-LEAP2 antibody) described herein is useful in methods of treating anorexia. In some embodiments, a method of treating anorexia in a subject comprises administering to the subject a therapeutically effective amount of a binding agent (e.g., an anti-LEAP2 antibody) described herein.

In some embodiments, a binding agent (e.g., an anti-LEAP2 antibody) described herein is useful in methods of stabilizing blood glucose levels under conditions of fasting or a restricted calorie diet. In some embodiments, a method of stabilizing blood glucose levels in a subject under conditions of fasting or a restricted calorie diet comprises administering to the subject a therapeutically effective amount of a binding agent (e.g., an anti-LEAP2 antibody) described herein. In some embodiments, a method of stabilizing fasting blood glucose levels in a subject comprises administering to the subject a therapeutically effective amount of a binding agent (e.g., an anti-LEAP2 antibody) described herein. In some embodiments, a binding agent (e.g., an anti-LEAP2 antibody) described herein is useful in methods for increasing growth hormone levels. In some embodiments, a method of increasing growth hormone levels in a subject comprises administering to the subject a therapeutically effective amount of a binding agent (e.g., an anti-LEAP2 antibody) described herein.

In some embodiments of the methods described herein, a binding agent is an anti-LEAP2 antibody that comprises: a heavy chain CDR1 comprising GYTFTSYWMH (SEQ ID NO:20), a heavy chain CDR2 comprising AIYPGNSDT-SYKQKFKG (SEQ ID NO:21), and a heavy chain CDR3 comprising GKEEYLFAMDY (SEQ ID NO:22); and/or a light chain CDR1 comprising KSSQSLLYSSNQKNYLA (SEQ ID NO:23), a light chain CDR2 comprising WAST-RES (SEQ ID NO:24), and a light chain CDR3 comprising QQYYSYPT (SEQ ID NO:25). In some embodiments of the methods described herein, a binding agent is an antibody that comprises: a heavy chain CDR1 comprising GYSFTNYYIH (SEQ ID NO:26), a heavy chain CDR2 comprising YIDPFNGGTNYNQKFKG (SEQ ID NO:27), and a heavy chain CDR3 comprising RGYYYGFTY (SEQ ID NO:28); and/or a light chain CDR1 comprising KASQSVDYDGDSYMN (SEQ ID NO:29), a light chain CDR2 comprising TASNLES (SEQ ID NO:30), and a light chain CDR3 comprising QQSNEDPYT (SEQ ID NO:31). In some embodiments of the methods described herein, a binding agent is an anti-LEAP2 antibody that comprises a heavy chain variable region comprising SEQ ID NO:7 and a light chain variable region comprising SEQ ID NO:8. In some embodiments of the methods described herein, a binding agent is an anti-LEAP2 antibody that comprises a heavy chain variable region comprising SEQ ID NO:9 and a light chain variable region comprising SEQ ID NO:10. In some embodiments of the methods described herein, a binding agent is anti-LEAP2 antibody M1/M2. In some embodiments of the methods described herein, a binding agent is a humanized version of antibody M1/M2. In some embodiments of the methods described herein, a binding agent is anti-LEAP2 antibody M18. In some embodiments of the methods described herein, a binding agent is a humanized version of antibody M18.

In some embodiments of the methods described herein, a method comprises administering a binding agent (e.g., LEAP2 or a variant thereof or an anti-LEAP2 antibody) described herein in combination with at least one additional therapeutic agent or therapeutic therapy. Treatment with two or more therapeutic agents often uses agents that work by different mechanisms of action, although this is not required. Combination therapy using agents with different mechanisms of action may result in additive or synergetic effects. Combination therapy may allow for a lower dose of each agent than is used in monotherapy, thereby reducing toxic side effects and/or increasing the therapeutic index of the agent(s). Combination therapy may decrease the likelihood that resistance to an agent will develop.

In some embodiments, the combination of a binding agent (e.g., LEAP2 or a variant thereof or an anti-LEAP2 antibody) described herein and at least one additional therapeutic agent results in additive or synergistic results. In some embodiments, the combination therapy results in an increase in the therapeutic index of the binding agent (e.g., LEAP2 or a variant thereof or an anti-LEAP2 antibody). In some embodiments, the combination therapy results in an increase in the therapeutic index of the additional therapeutic agent(s). In some embodiments, the combination therapy results in a decrease in the toxicity and/or side effects of the binding agent (e.g., LEAP2 or a variant thereof or an anti-LEAP2 antibody). In some embodiments, the combination therapy results in a decrease in the toxicity and/or side effects of the additional therapeutic agent(s).

In some embodiments, an additional therapeutic agent can be administered prior to, concurrently with, and/or subsequently to, administration of the binding agent (e.g., LEAP2 or a variant thereof or an anti-LEAP2 antibody). In some embodiments, the at least one additional therapeutic agent comprises 1, 2, 3, or more additional therapeutic agents.

Combined administration can include co-administration, either in a single pharmaceutical formulation or using separate formulations, or consecutive administration in either order but generally within a time period such that all active agents can exert their biological activities. Preparation and dosing schedules for additional therapeutic agents can be used according to manufacturers' instructions or as determined empirically by the skilled practitioner.

In some embodiments of the methods described herein, a method comprises administering LEAP2 or variant thereof described herein in combination with an additional therapeutic agent. In some embodiments, the additional therapeutic agent is a hyperglycemia or diabetes drug. Hyperglycemia or diabetes drugs include, but are not limited to, insulin and insulin mimetics; PPAR (peroxisome proliferator-activated receptor) γ-agonists, such as pioglitazone, troglitazone, ciglitazone, rivoglitazone, rosiglitazone, and other 2,4-thiazolidinedione derivatives; DPP-4 inhibitors, such as sitagliptin (JANUVIA), vildagliptin, saxagliptin, linagliptin (TRADJENTA), dutogliptin, gemigliptin, and alogliptin (NESINA); GLP-1 analogs, such as exenatide, liraglutide, taspoglutide, albiglutide, and lixisenatide; biguanidine derivatives, such as metformin (GLUMETZA, GLUCOPHAGE), buformin, and phenformin; ATP-sensitive potassium channel modulators, such as mitiglinide, repaglinide, and nateglinide; sulfonylurea derivatives, such as tolbutamide, chlorpropamide, tolazamide, acetohexamide, glipizide, gliclazide, glimepiride, gliquidone, glibornuride, glisoxepid, glibenclamide, glisentide, glisolamide, glybuzole, and glyclopyramide; α-glucosidase inhibitors, such as miglitol (GLYSET), acarbose (PRECOSE), and voglibose; and SGLT2 inhibitors, such as canagliflozin (INVOKANA), dapagliflozin (FARXIGA), and empagliflozin (JARDIANCE).

In some embodiments, the additional therapeutic agent is an obesity drug. Obesity drugs include, but are not limited to, orlistat (XENICAL), phentermine/topiramate (QSYMIA), lorcaserin (BELVIQ), naltrexone/bupropion (CONTRAVE) and liraglutide (SAXENDA).

In some embodiments, the additional therapeutic agent is a lipid-lowering drug or a cholesterol-lowering drug. Lipid-lowering drugs include, but are not limited to, fibrates, statins, omega-3 fatty acids, and niacin. In some embodiments, an additional therapeutic agent is a fibrate. Fibrates are a class of amphipathic carboxylic acids and include, but are not limited to, aluminum clofibrate, bezafibrate, ciprofibrate, choline fenofibrae, clinofibrate, clofibrate (e.g., ATROMID-S), clofibride, fenofibrate (e.g., FIBRICOR, LOFIBRA, TRICOR), gemfibrozil (e.g., LOPID), ronifibrate, simfibrate, and fenofibric acid. In some embodiments, an additional therapeutic agent is a statin. Statins are HMG-CoA reductase inhibitors and include, but are not limited to, atorvastatin (LIPITOR), fluvastatin (LESCOL), lovastatin (MEVACOR), pravastatin (PRAVACHOL), rosuvastatin (ZOCOR), and pitavastatin (LIVALO). In some embodiments, the additional therapeutic agent is niacin (vitamin B3). In some embodiments, the additional therapeutic agent is an omega-3 fatty acid.

In some embodiments, the additional therapeutic agent is selected from the group including, but to limited to, glucagon receptor antagonists; GLP-1, GLP-1 mimetics, and GLP-1 receptor agonists; GIP, GIP mimetics, and GIP receptor agonists; PACAP, PACAP mimetics, and PACAP receptor 3 agonists; cholesterol-lowering agents such as HMG-CoA reductase inhibitors, sequestrants, nicotinyl alcohol, nicotinic acid and salts thereof, PPAR alpha agonists, PPAR alpha/gamma dual agonists, inhibitors of cholesterol absorption, acyl CoA: cholesterol acyltransferase inhibitors, anti-oxidants, and LXR modulators; PPAR delta agonists; anti-obesity compounds; ileal bile acid transporter inhibitors; anti-inflammatory agents excluding glucocorticoids; protein tyrosine phosphatase-1B (PTP-1B) inhibitors, and CB1 antagonists/inverse agonists.

In some embodiments of the methods described herein, a method comprises administering an anti-LEAP2 antibody described herein in combination with an additional therapeutic agent. In some embodiments, the additional therapeutic agent is a progestogen. Progestogens include but are not limited to, dydrogesterone, medroxyprogesterone acetate (PROVERA), megestrol acetate, cyproterone acetate, nomegestrol acetate (NOMAC), trimegestone, promegestone, norethisterone, dienogest, norgestrel, levonorgestrel, desogestrel, norgestimate, gestodene, chlormadinone acetate, and cyproterone acetate. In some embodiments, the additional therapeutic agent is a corticosteroid. Corticosteroids include but are not limited to, prednisone, hydrocortisone, cortisone, bethamethasone, prednisolone, triamcinolone, and methylprednisolone. In some embodiments, the additional therapeutic agent is eicosapentaenoic acid. In some embodiments, the additional therapeutic agent is a cannabinoid. In some embodiments, the additional therapeutic agent is β-hydroxy β-methylbutyrate (HMB).

In some embodiments of the methods described herein, an additional therapeutic agent is an immunomodulatory agent. Generally, the term "immunomodulatory agent" as used herein refers to an agent that modulates an immune response. In some embodiments, an immunomodulatory agent is an immunostimulatory agent. In some embodiments, an immunomodulatory agent is an immunosuppressive agent.

It will be appreciated that the combination of a binding agent (e.g., LEAP2 or a variant thereof or an anti-LEAP2 antibody) described herein and at least one additional therapeutic agent may be administered in any order or concurrently. In some embodiments, the binding agent is administered to a subject that has previously undergone treatment with a therapeutic agent. In some embodiments, the binding agent and a second therapeutic agent are administered substantially simultaneously or concurrently. For example, a subject may be given a binding agent (e.g., LEAP2 or a variant thereof) while undergoing a course of treatment with a second therapeutic agent (e.g., anti-diabetic agent). In some embodiments, a binding agent is administered within 1 year of the treatment with a second therapeutic agent. In some embodiments, a binding agent is administered within 10, 8, 6, 4, or 2 months of any treatment with a second therapeutic agent. In some embodiments, a binding agent is administered within 4, 3, 2, or 1 weeks of any treatment with a second therapeutic agent. In some embodiments, a binding agent is administered within 5, 4, 3, 2, or 1 days of any treatment with a second therapeutic agent. It will further be appreciated that the two (or more) agents or treatments may be administered to the subject within a matter of hours or minutes (i.e., substantially simultaneously).

For the treatment of a disease, the appropriate dosage of a binding agent (e.g., LEAP2 or a variant thereof or an anti-LEAP2 antibody) described herein depends on the disorder or disease to be treated, the severity and course of the disorder or disease, the responsiveness of the disorder or disease, whether the agent is administered for therapeutic or preventative purposes, previous therapy, the patient's clinical history, and so on. The binding agent can be administered one time or over a series of treatments lasting from several days to several months, or until a cure is effected or a diminution of the disease state is achieved.

In some embodiments, dosage of the agent is from 0.01 μg to 100 mg/kg of body weight, from 0.1 μg to 100 mg/kg of body weight, from 1 μg to 100 mg/kg of body weight, from 1 mg to 100 mg/kg of body weight, 1 mg to 80 mg/kg of body weight from 10 mg to 100 mg/kg of body weight, from 10 mg to 75 mg/kg of body weight, or from 10 mg to 50 mg/kg of body weight. In some embodiments, dosage of the agent is from about 0.1 mg to about 20 mg/kg of body weight. In some embodiments, dosage of the agent is about 0.5 mg/kg of body weight. In some embodiments, dosage of the agent is about 1 mg/kg of body weight. In some embodiments, dosage of the agent is about 1.5 mg/kg of body weight. In some embodiments, dosage of the agent is about 2 mg/kg of body weight. In some embodiments, dosage of the agent is about 2.5 mg/kg of body weight. In some embodiments, dosage of the agent is about 5 mg/kg of body weight. In some embodiments, dosage of the agent is about 7.5 mg/kg of body weight. In some embodiments, dosage of the agent is about 10 mg/kg of body weight. In some embodiments, dosage of the agent is about 12.5 mg/kg of body weight. In some embodiments, dosage of the agent is about 15 mg/kg of body weight. In some embodiments, the agent is dosed once or more daily, weekly, monthly, or yearly. In some embodiments, the agent is dosed once every week, once every two weeks, once every three weeks, or once every four weeks.

The present disclosure provides compositions comprising a binding agent (e.g., LEAP2 or a variant thereof or an anti-LEAP2 antibody) described herein. In some embodiments, a composition comprises SEQ ID NO:2. In some embodiments, a composition consists of SEQ ID NO:2. In some embodiments, a composition comprises LEAP2. In some embodiments, a composition comprises a LEAP2 variant. In some embodiments, a composition comprises an anti-LEAP2 antibody selected from antibodies M1/M2 and M18. In some embodiments, a composition comprises an anti-LEAP2 antibody that comprises a heavy chain CDR1 comprising GYTFTSYWMH (SEQ ID NO:20), a heavy chain CDR2 comprising AIYPGNSDTSYKQKFKG (SEQ ID NO:21), and a heavy chain CDR3 comprising GKEEY-LFAMDY (SEQ ID NO:22); and a light chain CDR1 comprising KSSQSLLYSSNQKNYLA (SEQ ID NO:23), a light chain CDR2 comprising WASTRES (SEQ ID NO:24), and a light chain CDR3 comprising QQYYSYPT (SEQ ID NO:25). In some embodiments, a composition comprises an anti-LEAP2 antibody that comprises a heavy chain variable region comprising SEQ ID NO:7 and a light chain variable region comprising SEQ ID NO:8. In some embodiments, a composition comprises the anti-LEAP2 antibody M1/M2. In some embodiments, a composition comprises a humanized version of antibody M1/M2. In some embodiments, a composition comprises an anti-LEAP2 antibody that comprises a heavy chain CDR1 comprising GYSFTNYYIH (SEQ ID NO:26), a heavy chain CDR2 comprising YIDPFNGGTNYNQKFKG (SEQ ID NO:27), and a heavy chain CDR3 comprising RGYYYGFTY (SEQ ID NO:28); and a light chain CDR1 comprising KASQSVDYDGDSYMN (SEQ ID NO:29), a light chain CDR2 comprising TASNLES (SEQ ID NO:30), and a light chain CDR3 comprising QQSNEDPYT (SEQ ID NO:31). In some embodiments, a composition comprises an anti-LEAP2 antibody that comprises a heavy chain variable region comprising SEQ ID NO:9 and a light chain variable region comprising SEQ ID NO:10. In some embodiments, a composition comprises the anti-LEAP2 antibody M18. In some embodiments, a composition comprises a humanized version of antibody M18.

The present disclosure also provides pharmaceutical compositions comprising a binding agent (e.g., LEAP2 or a variant thereof or an anti-LEAP2 antibody) described herein and at least one pharmaceutically acceptable vehicle. In some embodiments, a pharmaceutical composition comprises SEQ ID NO:2 and at least one pharmaceutically acceptable vehicle. In some embodiments, a pharmaceutical composition consists of SEQ ID NO:2 and at least one pharmaceutically acceptable vehicle. In some embodiments, a composition comprises LEAP2 and at least one pharmaceutically acceptable vehicle. In some embodiments, a composition comprises a LEAP2 variant and at least one pharmaceutically acceptable vehicle. In some embodiments, a pharmaceutical composition comprises an anti-LEAP2 antibody that comprises a heavy chain CDR1 comprising GYTFTSYWMH (SEQ ID NO:20), a heavy chain CDR2 comprising AIYPGNSDTSYKQKFKG (SEQ ID NO:21), and a heavy chain CDR3 comprising GKEEYLFAMDY (SEQ ID NO:22); and a light chain CDR1 comprising KSSQSLLYSSNQKNYLA (SEQ ID NO:23), a light chain CDR2 comprising WASTRES (SEQ ID NO:24), and a light chain CDR3 comprising QQYYSYPT (SEQ ID NO:25) and at least one pharmaceutically acceptable vehicle. In some embodiments, a pharmaceutical composition comprises an anti-LEAP2 antibody that comprises a heavy chain variable region comprising SEQ ID NO:7 and a light chain variable region comprising SEQ ID NO:8. In some embodiments, a pharmaceutical composition comprises the anti-LEAP2 antibody M1/M2. In some embodiments, a pharmaceutical composition comprises a humanized version of antibody M1/M2. In some embodiments, a pharmaceutical composition comprises an anti-LEAP2 antibody that comprises a heavy chain CDR1 comprising GYSFTNYYIH (SEQ ID NO:26), a heavy chain CDR2 comprising YIDPFNGGTNYNQKFKG (SEQ ID NO:27), and a heavy chain CDR3 comprising RGYYYGFTY (SEQ ID NO:28); and a light chain CDR1 comprising KASQSVDYDGDSYMN (SEQ ID NO:29), a light chain CDR2 comprising TASNLES (SEQ ID NO:30), and a light chain CDR3 comprising QQSNEDPYT (SEQ ID NO:31). In some embodiments, a pharmaceutical composition comprises an anti-LEAP2 antibody that comprises a heavy chain variable region comprising SEQ ID NO:9 and a light chain variable region comprising SEQ ID NO:10. In some embodiments, a pharmaceutical composition comprises the anti-LEAP2 antibody M18. In some embodiments, a pharmaceutical composition comprises a humanized version of antibody M18.

Formulations are prepared for storage and/or use by combining a purified protein or antibody of the present disclosure with a pharmaceutically acceptable vehicle (e.g., a carrier or excipient). Those of skill in the art generally consider pharmaceutically acceptable carriers, excipients, and/or stabilizers to be inactive ingredients of a formulation or pharmaceutical composition. A formulation prepared for storage of a binding agent may be different or distinct from a formulation or composition prepared for use in a subject, for example, a preparation for intravenous injection.

Suitable pharmaceutically acceptable vehicles include, but are not limited to, nontoxic buffers such as phosphate, citrate, and other organic acids; salts such as sodium chloride; antioxidants including ascorbic acid and methionine; preservatives such as octadecyldimethylbenzyl ammonium chloride, hexamethonium chloride, benzalkonium chloride, benzethonium chloride, phenol, butyl or benzyl alcohol, alkyl parabens, such as methyl or propyl paraben, catechol, resorcinol, cyclohexanol, 3-pentanol, and m-cresol; low molecular weight polypeptides (e.g., less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosaccharides, disaccharides, glucose, mannose, or dextrins; chelating agents such as EDTA; sugars such as sucrose, mannitol, trehalose or sorbitol; salt-forming counter-ions such as sodium; metal complexes such as Zn-protein complexes; and non-ionic surfactants such as TWEEN or polyethylene glycol (PEG). (*Remington: The Science and Practice of Pharmacy*, $22^{nd}$ Edition, 2012, Pharmaceutical Press, London). In some embodiments, the formulation is in the form of an aqueous solution. In some embodiments, the formulation is lyophilized or in an alternative dried form.

The therapeutic formulation can be in unit dosage form. Such formulations include tablets, pills, capsules, powders, granules, solutions or suspensions in water or non-aqueous media, or suppositories. In solid compositions such as tablets the principal active ingredient is mixed with a pharmaceutical carrier. Conventional tableting ingredients include corn starch, lactose, sucrose, sorbitol, talc, stearic acid, magnesium stearate, dicalcium phosphate or gums, and diluents (e.g., water). These can be used to form a solid preformulation composition containing a homogeneous mixture of a compound of the present disclosure, or a non-toxic pharmaceutically acceptable salt thereof. The solid preformulation composition is then subdivided into unit dosage forms of a type described above. The tablets, pills, etc. of the formulation or composition can be coated or otherwise compounded to provide a dosage form affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, such materials include a number of polymeric acids and mixtures of polymeric acids with such materials as shellac, cetyl alcohol, and cellulose acetate.

The binding agents of the present disclosure may be formulated in any suitable form for delivery to a target cell/tissue. In some embodiments, a binding agent (e.g., LEAP2 or a variant thereof or an anti-LEAP2 antibody) is formulated as a liposome, microparticle, microcapsule, albumin microsphere, microemulsion, nano-particle, nanocapsule, or macroemulsion. In some embodiments, the pharmaceutical formulation includes an agent of the present disclosure complexed with liposomes. Methods to produce liposomes are known to those of skill in the art. For example, some liposomes are generated by reverse phase evaporation with a lipid composition comprising phosphatidylcholine, cholesterol, and PEG-derivatized phosphatidylethanolamine (PEG-PE).

In some embodiments, a binding agent (e.g., LEAP2 or a variant thereof or an anti-LEAP2 antibody) is formulated as a sustained-release preparation. Suitable examples of sustained-release preparations include semi-permeable matrices of solid hydrophobic polymers containing an agent, where the matrices are in the form of shaped articles (e.g., films or microcapsules). Sustained-release matrices include but are not limited to polyesters, hydrogels such as poly(2-hydroxyethyl-methacrylate) or poly(vinyl alcohol), polylactides, copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The pharmaceutical compositions or formulations of the present disclosure can be administered in any number of ways for either local or systemic treatment. Administration can be topical by epidermal or transdermal patches, ointments, lotions, creams, gels, drops, suppositories, sprays, liquids and powders; pulmonary by inhalation or insufflation of powders or aerosols, including by nebulizer, intratracheal, and intranasal; oral; or parenteral including intravenous, intraarterial, intratumoral, subcutaneous, intraperitoneal, intramuscular (e.g., injection or infusion), or intracranial (e.g., intrathecal or intraventricular).

Various delivery systems are known and can be used to administer a binding agent (e.g., LEAP2 or a variant thereof or an anti-LEAP2 antibody) described herein. In some embodiments, a binding agent (e.g., LEAP2 or a variant thereof or an anti-LEAP2 antibody) or a composition described herein is delivered in a controlled release or sustained release system. In some embodiments, a pump is used to achieve a controlled or sustained release. In some embodiments, polymeric materials are used to achieve a controlled or sustained release of a binding agent (e.g., LEAP2 or a variant thereof or an anti-LEAP2 antibody) described herein. Examples of polymers used in sustained release formulations include, but are not limited to, poly-2-hydroxyethyl methacrylate, polymethyl methacrylate, polyacrylic acid, polyethylene-co-vinyl acetate, polymethacrylic acid, polyglycolides (PLG), polyanhydrides, poly N-vinyl pyrrolidone, polyvinyl alcohol (PVA), polyacrylamide, polyethylene glycol (PEG), polylactides (PLA), polylactide-co-glycolides (PLGA), and polyorthoesters. Any polymer used in a sustained release formulation should be inert, free of leachable impurities, stable on storage, sterile, and biodegradable.

In some embodiments, additional delivery systems are used to administer a binding agent (e.g., LEAP2 or a variant thereof or an anti-LEAP2 antibody) described herein including, but not limited to, injectable drug delivery devices and osmotic pumps. Injectable drug delivery devices include, for example, hand-held devices (e.g., autoinjectors) or wearable devices. Different types of osmotic pump systems may include single compartment systems, dual compartment systems, and multiple compartment systems.

V. Methods of Detection

In some embodiments, binding agents (e.g., anti-LEAP2 antibodies) of the present disclosure are useful for detecting the presence of LEAP2 in a biological sample. In some embodiments, an anti-LEAP2 antibody is an antibody that binds human and/or monkey LEAP2, but does not inhibit ghrelin-induced GHSR activity. The term "detecting" as used herein encompasses quantitative and qualitative detection. In certain embodiments, a biological sample comprises a cell or tissue.

In some embodiments, the present disclosure provides a method of detecting the presence of LEAP2 in a biological sample. In some embodiments, a method comprises contacting a biological sample with an anti-LEAP2 antibody under conditions permissive for binding of the anti-LEAP2 antibody to LEAP2, and detecting whether a complex is formed between the anti-LEAP2 antibody and LEAP2.

In certain embodiments, a method of detection, such as described above, comprises detecting binding of an anti-LEAP2 antibody to LEAP2 in a tissue, in a cell, or in a membrane preparation. In certain embodiments, a method comprises contacting a cell with an anti-LEAP2 antibody under conditions permissive for binding of the anti-LEAP2 antibody to LEAP2, and detecting whether a complex is formed between the anti-LEAP2 antibody and LEAP2 on the cell surface or within a cell.

A variety of methods known to those of skill in the art can be used to detect binding of anti-LEAP2 antibodies to LEAP2. Such methods include, but are not limited to, antigen-binding assays that are well known in the art, such as western blots, radioimmunoassays, ELISA, FACS, SPR (e.g., Biacore), sandwich immunoassays, immunoprecipitation assays, fluorescent immunoassays, protein A immunoassays, and immunohistochemistry (IHC).

In some embodiments, anti-LEAP2 antibodies are labeled. Labels may include, but are not limited to, moieties that are detected directly (such as fluorescent, chromophoric, electron-dense, chemiluminescent, and radioactive labels), and moieties that are detected indirectly through an enzymatic reaction or molecular interaction (such as enzymes or ligands). Exemplary labels include, but are not limited to, radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luciferases, such as firefly luciferase and bacterial luciferase; 2,3-dihydrophthalazinediones, horseradish peroxidase (HRP), alkaline phosphatase, β-galactosidase, glucoamylase, lysozyme, saccharide oxidases, such as glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Any of the above embodiments of diagnosis or detection may be carried out using an immunoconjugate of the present disclosure in place of or in addition to an anti-LEAP2 antibody.

VI. Kits

The present disclosure also contemplates kits comprising the disclosed binding agents (e.g., peptides or antibodies) and pharmaceutical compositions thereof. The kits are generally in the form of a physical structure housing various components, as described below, and may be utilized in practicing the methods described herein (e.g., administration of an anti-LEAP2 antibody to a subject in need of treatment).

Kits with unit doses of a binding agent (e.g., a peptide or antibody) of the present disclosure, for example, in oral or injectable doses, are provided. In some embodiments, a kit comprises one or more containers containing a unit dose(s) and an informational package insert or reference to an internet web site, describing the use and benefits of the agent in treating the pathological condition of interest.

In some embodiments, a kit includes one or more of a binding agent (e.g., a peptide or antibody) disclosed herein in the form of a pharmaceutical composition suitable for administration to a subject. In some embodiments, the binding agent (e.g., a peptide or antibody) is provided in an appropriate container, e.g., a sterile container. In some embodiments, the binding agent (e.g., a peptide or antibody) is provided in a form that is ready for use. In some embodiments, the binding agent (e.g., a peptide or antibody) is provided in a form requiring reconstitution or dilution prior to administration. When the binding agent (e.g., a peptide or antibody) is in a form that needs to be reconstituted by a user, the kit may also include buffers, pharmaceutically acceptable excipients, and the like, packaged with or separately from the binding agent. When combination therapy is contemplated, the kit may contain one or more additional therapeutic agents. In some embodiments, each component of the kit is enclosed within an individual container and all of the various containers are within a single kit package. A kit of the present disclosure can be designed for conditions necessary to properly maintain the biological properties of the components housed therein (e.g., refrigeration or freezing).

In some embodiments, a kit contains a label or packaging insert that includes identifying information for the components therein and instructions for their use (e.g., dosing parameters, clinical pharmacology of the active ingredient(s), mechanism of action, pharmacokinetics, pharmacodynamics, adverse effects, contraindications, etc.). Labels or inserts can include manufacturer information such as lot numbers and expiration dates.

Examples

Since the discovery of ghrelin, regulated secretion has been the sole mechanism described for controlling the action of this hormone. The present studies reveal a surprising and hitherto unknown mechanism of ghrelin regulation and GHSR activity. As described herein, LEAP2 was discovered to be a regulatory peptide that acts as an endogenous antagonist of GHSR. LEAP2 inhibited ghrelin-induced GHSR activity in a non-competitive manner, and inhibited or blocked ghrelin-induced growth hormone release (FIG. 4) and food intake (FIG. 6). Anti-LEAP2 antibodies enhanced ghrelin's activation of GHSR in vivo (see FIG. 10). In addition, LEAP2 inhibited the function of the ghrelin-GHSR axis to maintain glucose levels and viability during chronic calorie restriction (FIGS. 7 and 8). This discovery revealed a novel regulatory mechanism modulating ghrelin/GHSR activity. Thus, these studies identified LEAP2 as both a potential therapeutic target and a therapeutic molecule for neuroendocrine, metabolic, or ghrelin-related diseases, including obesity, diabetes, anorexia, cachexia, and Prader-Willi Syndrome.

Studies have indicated that high concentrations of LEAP2 exhibited antimicrobial activity (Howard, et al., 2010, *Cell. Immunol.*, 261:128-133; Krause, et al., 2003, *Prot. Sci.*, 12:143-152). The effective antimicrobial concentration reported in these studies is much higher than the physiological concentration of LEAP2 (~11 ng/ml, equivalent to 2.1 nM). The present disclosure identifies a role for LEAP2 that occurs at physiological levels of the peptide.

Another notable finding of the present disclosure is that LEAP2 may suppress ghrelin action through additional mechanisms beyond inhibiting ghrelin binding with GHSR. After chronic calorie restriction, ghrelin levels exhibited a smaller increase in LEAP2-expressing mice as compared to the control group. A similar inverse relationship was found between circulating levels of LEAP2 and ghrelin in response to nutritional conditions. After fasting, serum LEAP2 decreased, while serum ghrelin increased, whereas upon re-feeding, serum LEAP2 increased, while serum ghrelin decreased. This suggests that LEAP2 may act to inhibit the production or secretion of ghrelin. This double inhibition (antagonizing GHSR and inhibiting ghrelin production) makes LEAP2 a particularly strong regulator of ghrelin activity in vivo. Thus, the studies disclosed herein indicate that LEAP2 is a peptide that connects the gut, brain, and metabolic control. Furthermore, modulating the level of LEAP2 in the ghrelin/GHSR pathway may be a potential therapy for a number of neuroendocrine and/or metabolic diseases.

EXAMPLES

Example 1

Effects of VSG Surgery in Mouse Model

Bariatric surgery, an effective treatment for obesity and diabetes, leads to profound remodeling of whole body energy homeostasis (Miras and le Roux, 2013, *Nat. Rev. Gastroenterol. Hepatol.*, 10:575-584; Seeley, et al., 2015, *Cell Metab.*, 21:369-378). Obese subjects with poorly controlled diabetes who underwent either gastric bypass or sleeve gastrectomy combined with medical therapy were significantly more likely to achieve a glycated hemoglobin level of 6.0% or less 12 months after randomization than were subjects receiving medical therapy alone (Schauer, et al., 2012, *N Engl. J. Med.*, 366:1567-1576).

To understand the molecular changes that mediate the metabolic reprogramming after bariatric surgery, a mouse model of vertical sleeve gastrectomy (VSG) was established and used as a tool to study glucose levels and gene expression profiles in mice with and without VSG surgery. C57BL/6 mice were purchased from The Jackson Laboratory. Mice were kept in accordance with welfare guidelines under controlled light, temperature, and humidity conditions. The mice had free access to water and were fed ad libitum on a commercial diet (Harlan Laboratories, Irradiated 2018 Teklad Global 18% Protein Rodent Diet) containing 18 kcal % fat, 24 kcal % protein and 58 kcal % carbohydrate. In some studies, mice were fed a high-fat diet (D12492, Research Diets) containing 60 kcal % fat, 20 kcal % protein and 20 kcal % carbohydrate. All animal studies were approved by the NGM Institutional Animal Care and Use Committee. Seventeen week old male C57BL/6J mice were fasted overnight prior to surgery. VSG and sham surgeries were performed under isoflurane anesthesia as described previously (Wilson-Perez, et al., 2013, *Diabetes*, 62:2380-85). Briefly, sterile 7 French polyethylene tubing was used to size the gastric pouch remnant from the esophagus to the pylorus and the lateral 80% of the stomach was excised. The stomach was closed at the edge using a single interrupted suture through both layers of stomach wall. The remaining stomach pouch had a lumen diameter sized to the polyethylene tubing and was approximately 20% of the original stomach area. The sham procedure involved the opening of the peritoneal cavity and applying a gentle pressure using a pair of hemostats at a location that is approximately ⅔ cranial to the greater curvature, along a vertical line between the esophageal sphincter and the pylorus. All mice consumed Osmolite 1 Cal liquid diet (Abbott Laboratories) for the first three days post-surgery and were gradually reintroduced to a high-fat diet on Day 3 (diet-induced obesity). The surgery survival rate was 100%.

VSG or sham surgery was performed as described above on two groups of mice (n=3 mice). After three weeks, an intraperitoneal glucose tolerance test (IPGTT) was performed on each mouse. Blood glucose levels were measured every 30 minutes over the course of two hours. Blood was taken from the mice by nicking the tail vein and glucose levels were measured using Accu-Chek® Active test strips read on an Accu-Chek® Active meter (Roche Diagnostics) following the manufacturer's instructions. All readings were performed in duplicate and averaged.

Glucose levels were observed to be significantly reduced in mice having undergone VSG surgery as compared to mice having undergone sham surgery (data not shown).

As a tool to identify novel secreted protein and peptides that might act as important metabolic regulators, gene expression in the stomach and intestines following VSG or sham surgery in diet-induced obese mice was analyzed.

Four weeks after surgeries, tissues were harvested from three VSG mice and three sham surgery mice. Total RNA was prepared by homogenizing tissues in TRIzol® Reagent (Thermo-Fisher) according to the manufacturer's protocol. RNA quality was assessed using an Agilent Bioanalyzer (Agilent Technologies). RNA from the three animals in each group was pooled for RNA sequencing, but an aliquot of RNA from each animal was retained for qPCR follow-up. A RNA library was constructed using a TruSeq RNA Library Prep Kit (Illumina). RNA was sequenced using 50 bp paired-end reads on a HiSeq2000 platform (Illumina). Raw sequence data was aligned against the mouse reference genome using GSNAP/CUFFLINKS. The assembled data set was annotated using CUFFCOMPARE.

RNA sequencing and analysis revealed that the expression level of 1041 genes in the stomach increased or decreased by at least 2-fold. 169 of these genes encoded secreted proteins/peptides. Interestingly, 69 of these genes were found to exhibit expression in the duodenum that was opposite of the expression seen in the stomach. Amongst the 69 genes, Leap2 was identified as a gut-derived peptide differentially expressed in the stomach and duodenum after VSG surgery. As shown in FIG. 1, Leap2 expression levels increased approximately 52-fold in the stomach tissue of mice following VSG surgery as compared to mice after sham surgery. In addition, Leap2 decreased by approximately 94.3% in the duodenum of mice following VSG surgery as compared to its expression in sham surgery controls. In contrast, Ghrl expression levels decreased by approximately 85% in the stomach tissue of mice following VSG surgery as compared to mice following sham surgery.

Example 2

Receptor Identification

LEAP2 is a secreted peptide originally purified from human blood ultrafiltrate (Krause, et al., 2003, *Prot. Sci.*, 12:143-152). The mature form of LEAP2 found in circulation is a 40 amino acid cationic bicyclic peptide containing two disulfide bridges (FIG. 2A). The amino acid sequence of mature LEAP2 is evolutionarily conserved and the four cysteine residues that form the disulfide bonds are highly conserved among vertebrate species (FIG. 2C). Although the bicyclic structure of LEAP2 is reminiscent of many peptide hormones (Joo, 2012, *Biomol. Ther.*, 20:19-26), the biological function of LEAP2 is not understood.

A synthetic LEAP2 peptide (SEQ ID NO:2) was screened against a panel of 168 engineered stable cell lines each expressing a single GPCR. LEAP2 peptide was tested in an agonist format (i.e., LEAP2 peptide was added to each receptor in the absence of ligand) and an antagonist format (i.e., LEAP2 peptide was added to each receptor in the presence of an EC80 concentration of the receptor's known ligand or agonist). The GPCR-expressing cell lines were engineered using the PathHunter® β-arrestin enzyme fragment complementation (EFC) technology (DiscoverX). This platform monitors GPCR activation through measurement of the reconstitution of a β-galactosidase enzyme split into complementary enzyme acceptor and enzyme donor fragments. The enzyme acceptor is fused to β-arrestin and the enzyme donor to a GPCR. GPCR activation leads to β-arrestin recruitment to the active receptor, resulting in β-galactosidase complementation.

Cells for each assay were seeded into white walled, 384-well microplates and incubated at 37° C. In agonist format, the cells were incubated with 3 µM synthetic LEAP2 peptide or DMSO vehicle control for 90 or 180 minutes. Responses were measured through chemiluminescent signal detection using the PathHunter Detection reagent cocktail (DiscoverX) and the plates were read using an Envision instrument (PerkinElmer). In antagonist format, the cells were pre-incubated with 3 µM synthetic LEAP2 peptide or DMSO vehicle for 30 min, followed by addition of a known agonist for the given receptor at the EC80 concentration. The plates were incubated for an additional 90 or 180 minutes and responses were measured as described above.

In agonist mode, no receptors were found to be activated by physiological concentrations of LEAP2 peptide (EC50≤100 nM). In contrast, in antagonist mode LEAP2 peptide fully inhibited the activity of GHSR, the receptor for ghrelin.

Example 3

LEAP2 Peptide Inhibs GHSR Activity

To gain additional insight regarding the function of LEAP2, GHSR activity assays were performed using the PathHunter® U2OS GHSR β-Arrestin Cell Line (DiscoverX) according to the manufacturer's instructions. As described above, cells were dispensed into 384-well plates, 5000 cells per well. In agonist format, cells were incubated with a dilution series of human ghrelin for 90 min. PathHunter detection reagent cocktail was added to the wells and the plates were incubated at room temperature for 1 hour. Chemiluminescence was read using an EnSpire® multimode plate reader (PerkinElmer). In antagonist format, cells were pre-incubated with a dilution series of LEAP2 peptide for 30 min, followed by incubation with ghrelin at 13 nM (EC80) for 90 minutes. Signals were detected and measured as described above.

For agonist format, percentage activity was calculated using the following formula: % Activity=100%×(mean RLU of test sample−mean RLU of vehicle control)/(mean MAX control ligand−mean RLU of vehicle control). For antagonist format, percentage inhibition was calculated using the following formula: % Inhibition=100%×(1−(mean RLU of test sample−mean RLU of vehicle control)/(mean RLU of EC80 control−mean RLU of vehicle control).

Ghrelin was shown to activate GHSR with an EC50 of 7.09±0.07 nM, similar to the potency that has been reported previously (Kojima, et al., 1999, *Nature*, 402:656-660). In contrast to ghrelin, LEAP2 peptide did not affect signaling through GHSR either positively or negatively, indicating that it is neither an agonist nor an inverse agonist of GHSR. Importantly, in antagonist format, LEAP2 fully inhibited ghrelin-induced GHSR activation with an IC50 of 6.74 nM.

LEAP2 binding to GHSR was further validated in an independent GHSR-expressing cell line in which activation was detected by calcium mobilization. In this assay, cells stably-express wild-type GHSR. Activation of GHSR triggers Gaq activation, resulting in phospholipase C activation, and ultimately, mobilization of calcium from intracellular stores. Calcium concentration is detected by the calcium-sensitive dye FLUO-3.

The results from this assay paralleled the previous study, i.e., ghrelin-induced GHSR activity was demonstrated by calcium mobilization. Ghrelin-induced GHSR activity was found to be dose-dependent with an EC50 of 4.25±0.67 nM. LEAP2 peptide was shown to completely abrogate the ghrelin-induced GHSR activity with an IC50 of 11.62 nM.

These results indicated that LEAP2 was an antagonist of GHSR and that LEAP2 was capable of inhibiting the receptor with a potency similar to that with which ghrelin activates the receptor.

Example 4

Competition Assays

Competitive antagonists bind to, but do not activate a receptor. Generally, a competitive antagonist competes with an agonist for the ligand-binding pocket of a receptor, impacting agonist potency but not the magnitude of maximal receptor response. In contrast, a non-competitive antagonist generally causes insurmountable inhibition that reduces the magnitude of the maximal response and cannot be overcome by excess agonist (Whiteley, 2000, *Cell Biochem Biophys.*, 33:217-25).

To identify the mode of antagonism employed by LEAP2 peptide, ghrelin-induced GHSR activation was measured in the presence of increasing concentrations of LEAP2 peptide. The results showed that LEAP2 peptide reduced the magnitude of maximal GHSR activation by ghrelin and that this inhibition could not be overcome by increasing concentrations of ghrelin. In a parallel experiment, the ability of ghrelin to activate GHSR in the presence of a known GHSR competitive antagonist, [D-Arg$^1$, D-Phe$^5$, D-Trp$^{7,9}$, Leu$^{11}$]-Substance P, was evaluated. The competitive antagonist shifted the ghrelin dose-dependent response curve to the right but had no impact on maximal GHSR activation by ghrelin.

These results demonstrated that LEAP2 peptide was a non-competitive antagonist of GHSR.

Example 5

LEAP2 Binds GHSR

To examine the binding of LEAP2 to GHSR, COST cells were transiently transfected with human GHSR using Lipofectamine 2000 (Thermo Fisher), and a binding assay was performed with LEAP2 peptide. 24 hours after transfection, GHSR-expressing cells and control cells were washed in DMEM medium, and incubated with Alexa 647-labeled LEAP2 peptide (3 μg/ml) for 30 minutes at room temperature. Cells were washed three times with PBS and fixed with 4% paraformaldehyde for 10 minutes at room temperature. Cells were washed following fixation, blocked, and mixed with an anti-GHSR antibody (rabbit-anti-GHSR, AbCam, 1:200) diluted in blocking solution. The mixture was incubated for 2 hours at room temperature. Cells were washed three times with PBS and incubated with anti-rabbit IgG secondary antibody conjugated to Alexa 488 (diluted 1:500, Jackson ImmunoResearch). Cells were counterstained with Hoechst 33342 (Sigma), and mounted on slides using Pro-Long Antifade reagent (Thermo Fisher). Confocal fluorescence microscopy was performed using a Zeiss LSM880 confocal microscope. Z-sections were superimposed into single images.

LEAP2 co-localized with GHSR in GHSR-transfected cells, but not in non-transfected cells. These data suggest that LEAP2 peptide binds directly to GHSR.

Example 6

Tissue Expression of LEAP2

Ghrelin is notable for its highly localized expression in the stomach and its regulation in response to feeding status and to surgical procedures that remodel the gastrointestinal tract (Kojima and Kangawa, 2005, *Physiol. Rev.*, 85:495-522; Cummings et al., 2002, *N. Engl. J. Med.*, 346:1623-1630; Miras and le Roux, 2013, *Nat. Rev. Gastroentero. Hepatol.*, 10:575-584). Given the discovery of interplay between ghrelin and LEAP2 described herein, the localization of Leap2 expression and its regulation in response to feeding and bariatric surgery was examined.

Total RNA was isolated from 24 tissues of adult mice and the RNA concentrations were normalized. qPCR was run using a QuantStudio™ 7 Flex Real-Time PCR System (Thermo Fisher). The relative amount of mRNA was calculated by the comparative threshold cycle ($\Delta C_T$) method. GAPDH mRNA was used as an internal control.

Figure 3:
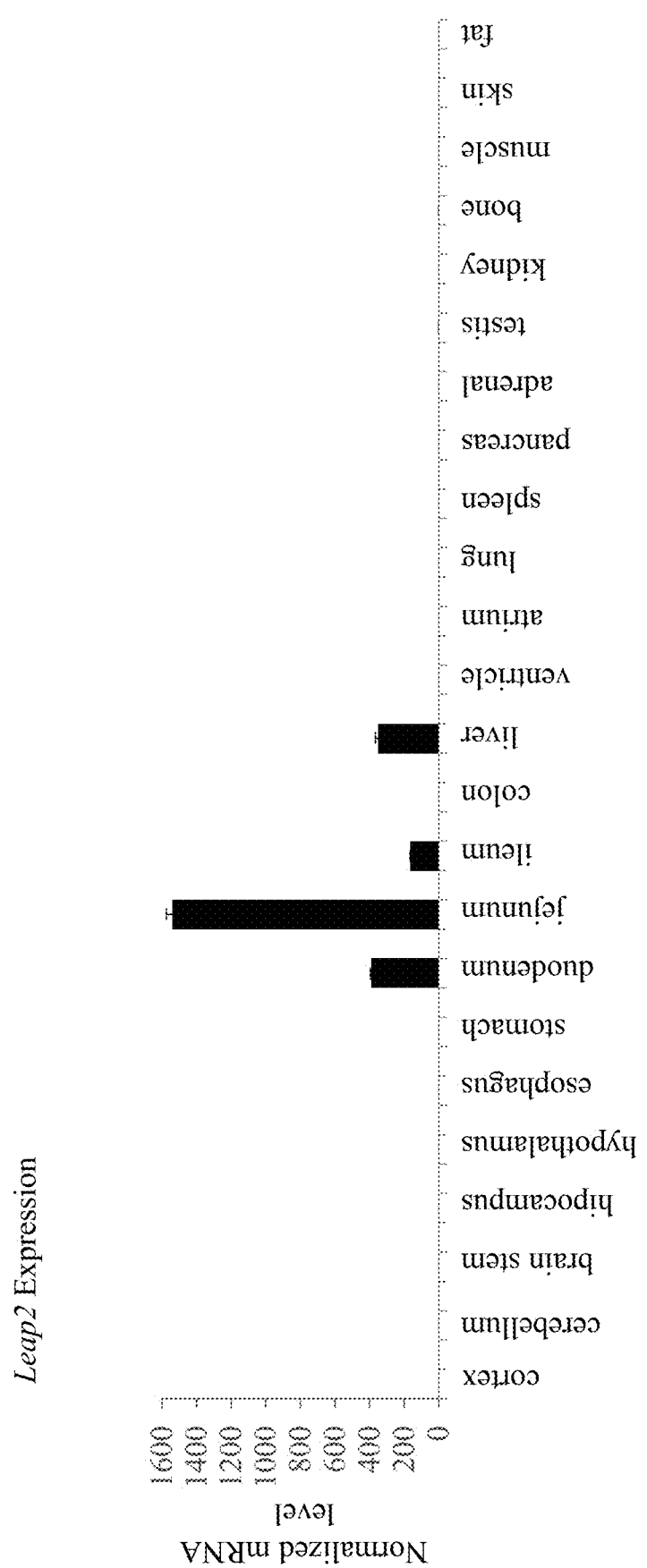
FIG. 3. Expression of LEAP2 mRNA in a panel of human tissues.

As shown in FIG. 3, the highest expression of Leap2 was found in the jejunum. Duodenum, ileum, and liver also expressed Leap2, whereas all other tissues showed minimal or no detectable expression.

Subsequently, studies were set up to identify the cell types that produce LEAP2. Since LEAP2 is a secreted protein, the localization of Leap2 transcripts was studied using RNAScope®, a well-established in situ hybridization method (Wang et al., 2012, *J. Mol. Diagnostics*, 14:22-29).

Consistent with the qPCR results, in situ hybridization showed the highest expression of Leap2 in jejunum and a lower level of expression in the liver. In liver, Leap2 showed moderate expression in hepatocytes. Within the jejunum, Leap2 was highly and specifically expressed in enterocytes along the luminal surface of the villi, but not in lamina propria or crypts. The increased expression of Leap2 in enterocytes may indicate the potential for LEAP2 regulation in response to nutrient status.

Example 7

LEAP2 Activity In Vivo

To investigate whether LEAP2 antagonizes ghrelin in vivo, two well-established actions of ghrelin in the mouse were evaluated, growth hormone (GH) release and food intake. Studies have shown that activation of GHSR by ghrelin in pituitary cells leads to robust growth hormone release. (Kojima, et al., 1999, *Nature*, 402:656-660; McFarlane, et al., 2014, *Cell Metab.*, 20:54-60; Sun, et al., 2004, *PNAS*, 101:4679-4684; Thomas, et al., 2016, *Am. J. Physiol. Regul. Integr. Comp. Physiol.*, 310:275-285).

To measure ghrelin-induced growth hormone release, three- to four-month-old male mice were anesthetized with isoflurane and blood samples were obtained through retro-orbital bleeding. Following a baseline blood collection (time 0), mice were injected intravenously with rat ghrelin (R&D Systems) or vehicle (PBS) through the tail vein, and blood samples were obtained at 5, 10, 15, 30, 60 min. Mice were euthanized at the end of the experiment.

Previous experiments had shown that a low dose of ghrelin administered intravenously induced a pulse of growth hormone release at about 5 minutes. To determine the effect of LEAP2 peptide on ghrelin-induced growth hormone release, LEAP2 (dosages of 0.72 to 360 μg/kg) or vehicle (10% DMSO in PBS) was injected intraperitoneally immediately after blood samples were taken at time 0. Ten minutes after LEAP2 injection, ghrelin (6 nmol/kg) was administrated intravenously. Blood samples were obtained at 5, 10, 15, 30, and 60 minutes after ghrelin injection. Growth hormone levels were measured from the serum samples.

Figure 4:
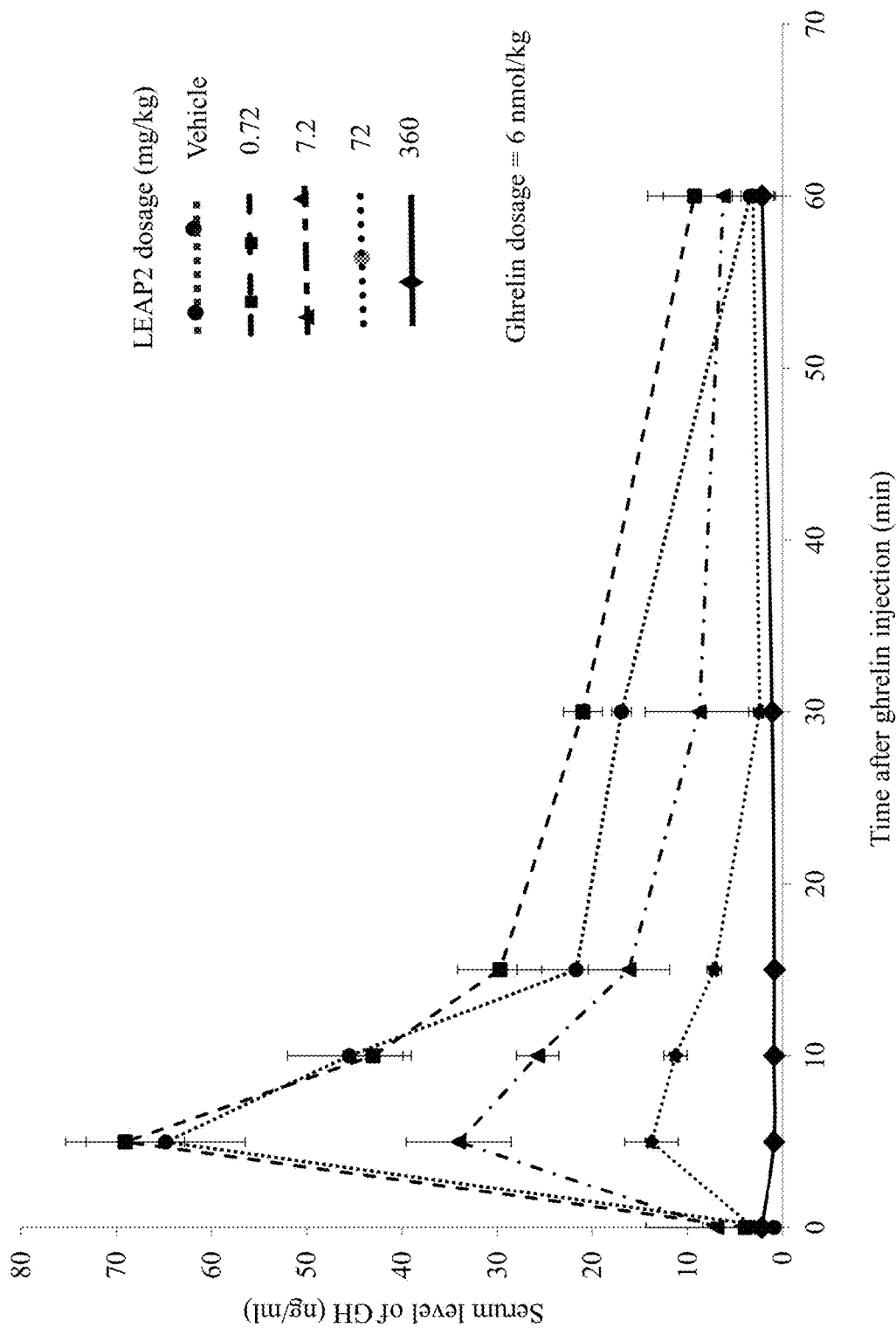
FIG. 4. LEAP2 inhibits ghrelin-induced growth hormone production in mice.

As shown in FIG. 4, the vehicle only treatment induced a pulse of growth hormone release. Strikingly, LEAP2 peptide attenuated ghrelin-induced growth hormone release in a dose-dependent manner. Starting from 7.2 nmol/kg, LEAP2 peptide significantly reduced the peak of growth hormone release as well as the total amount of growth hormone released as determined by the area under the curve. Notably, this dose of LEAP2 peptide is similar to the dose of ghrelin used in the experiment (6 nmol/kg), consistent with the in vitro pharmacology demonstrating that the IC50 of LEAP2 peptide on GHSR activity is similar to the EC50 of ghrelin. These results may suggest that the binding of LEAP2 peptide to GHSR on pituitary cells inhibits ghrelin-induced growth hormone release from these cells.

To measure endogenous LEAP2 levels, a "sandwich ELISA" was developed. Briefly, 96-well plates were coated with a goat-anti-LEAP2 antibody (Santa Cruz Biotechnology) and incubated for 72 hours at 4° C. Plates were washed 3 times with PBST (0.05% Tween® 20 in PBS) and blocked in 5% BSA-PBS. 10 µl of LEAP2 standard (synthetic LEAP2 peptide) or serum was mixed with 90 µl assay buffer (2% BSA-PBS) and added to appropriate wells. Samples were incubated for 15 min at room temperature on an orbital shaker, followed by an incubation for 2 hours at 37° C. Plates were washed 3 times in PBST, rabbit anti-LEAP2 capture antibody (AbCam) was added and the plates were incubated for 1 hour at room temperature. After 3 washes, HRP-goat-anti-rabbit secondary antibody was added to the wells and incubated for 1 hr at room temperature. Excess secondary antibody was washed away, followed by addition of KPL peroxidase substrate solution and plates were incubated until development of blue color was apparent. Stop solution (2N $H_2SO_4$) was added to the wells and the plates were read using an EnSpire 2000 multimode plate reader (PerkinElmer). Standard curves were fitted using a $2^{nd}$ order polynomial and LEAP2 levels were interpolated from the standard curve.

Figure 5:
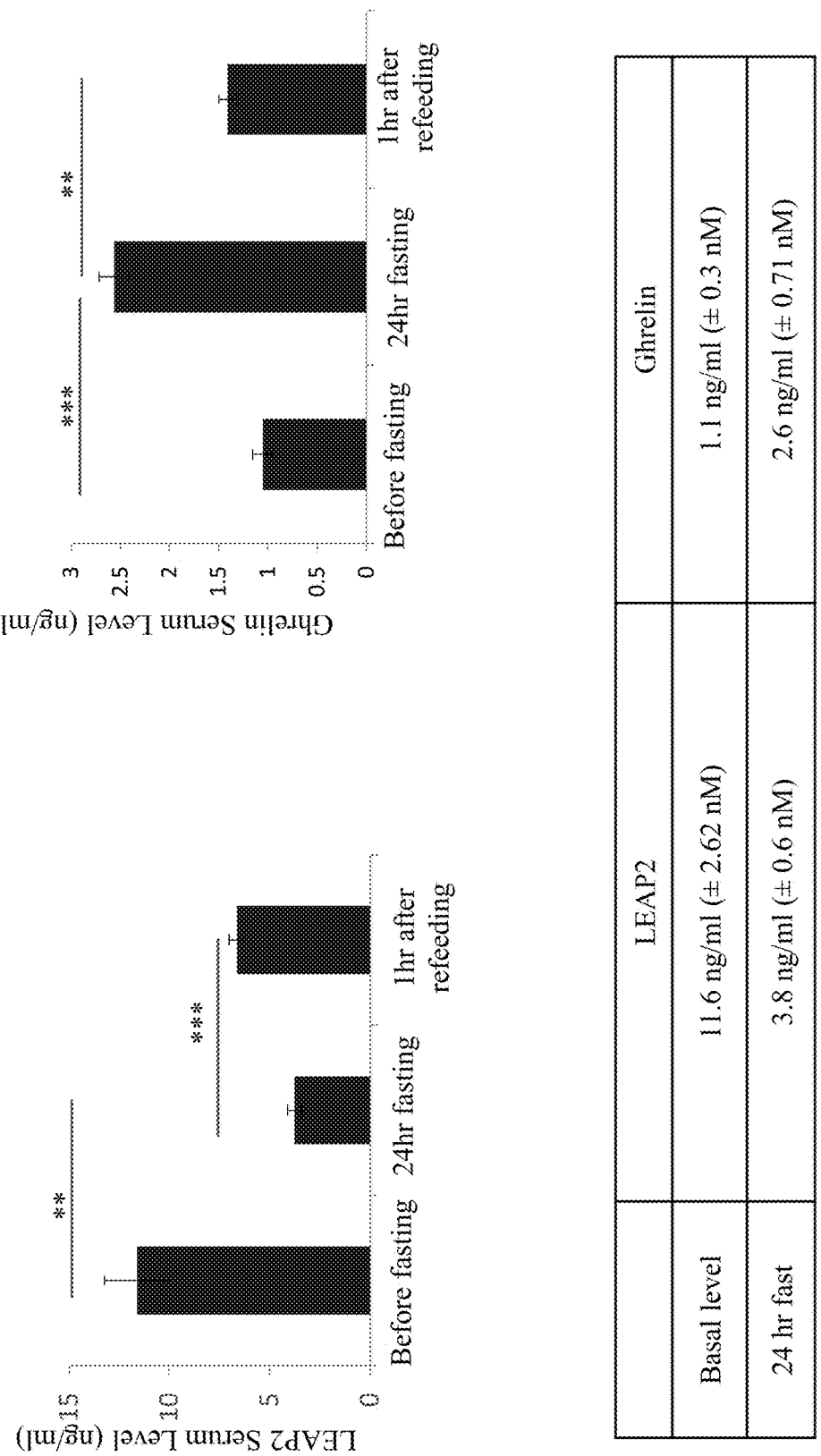
FIG. 5. LEAP2 and ghrelin serum levels before fasting, after fasting, and after refeeding.

Mature LEAP2 peptide (SEQ ID NO:2) was administered intravenously into mice and used to construct a standard curve for measurement of serum levels of LEAP2 peptide. Subsequently, the effects of fasting and refeeding on serum levels of LEAP2 peptide and ghrelin were measured in mice. As shown in FIG. 5, the baseline level of LEAP2 peptide in mouse serum averaged 11.6 ng/mL and after a 24 hour fast LEAP2 peptide levels were significantly decreased to 3.8 ng/mL, a decrease of 67%. One hour after refeeding, serum LEAP2 peptide levels were partially restored to 6.6 ng/mL. Serum ghrelin levels exhibited an inverse regulatory pattern, increasing from 1.1 ng/mL to 2.6 ng/mL after fasting and decreasing to near pre-fast levels after refeeding. This opposing regulation of LEAP2 and ghrelin in response to food intake aligns with the action of LEAP2 in opposing ghrelin signaling through GHSR. As discussed herein, a similar pattern of counter-regulation between LEAP2 and ghrelin was observed in Leap2 and Ghrl expression in the stomach following VSG surgery (FIG. 1).

Example 8

Effects of Ghrelin and LEAP2 on Food Intake

Activation of GHSR in hypothalamic neurons stimulates an orexigenic neural pathway, resulting in increased food intake (Nakazato, et al., 2001, Nature, 409:194-198). This appetite-stimulatory effect is induced by supraphysiological levels of ghrelin (Sun, et al., 2004, PNAS, 101:4679-4684; McFarlane, et al., 2014, Cell Metab., 20:54-60; Lippl, et al., 2012, Regul. Pept., 174:26-31). Therefore, the effects of ghrelin and LEAP2 on food intake were examined.

Mice were anesthetized with isoflurane and injected subcutaneously with ghrelin (0.03 or 0.15 µmol/kg) or vehicle (PBS). Mice were housed in individual cages and food intake was measured at 0.5, 1, and 2 hours.

Figure 6A:
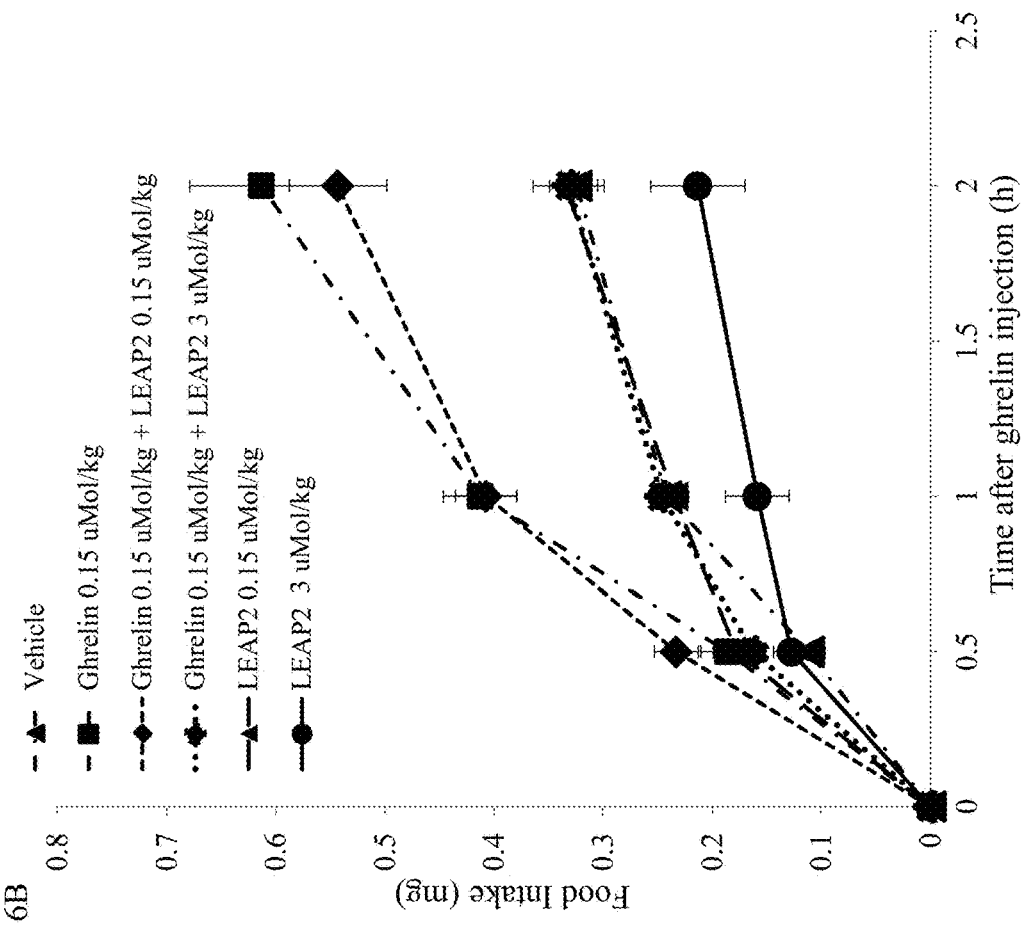
FIGS. 6A-6B.
Figure 7:
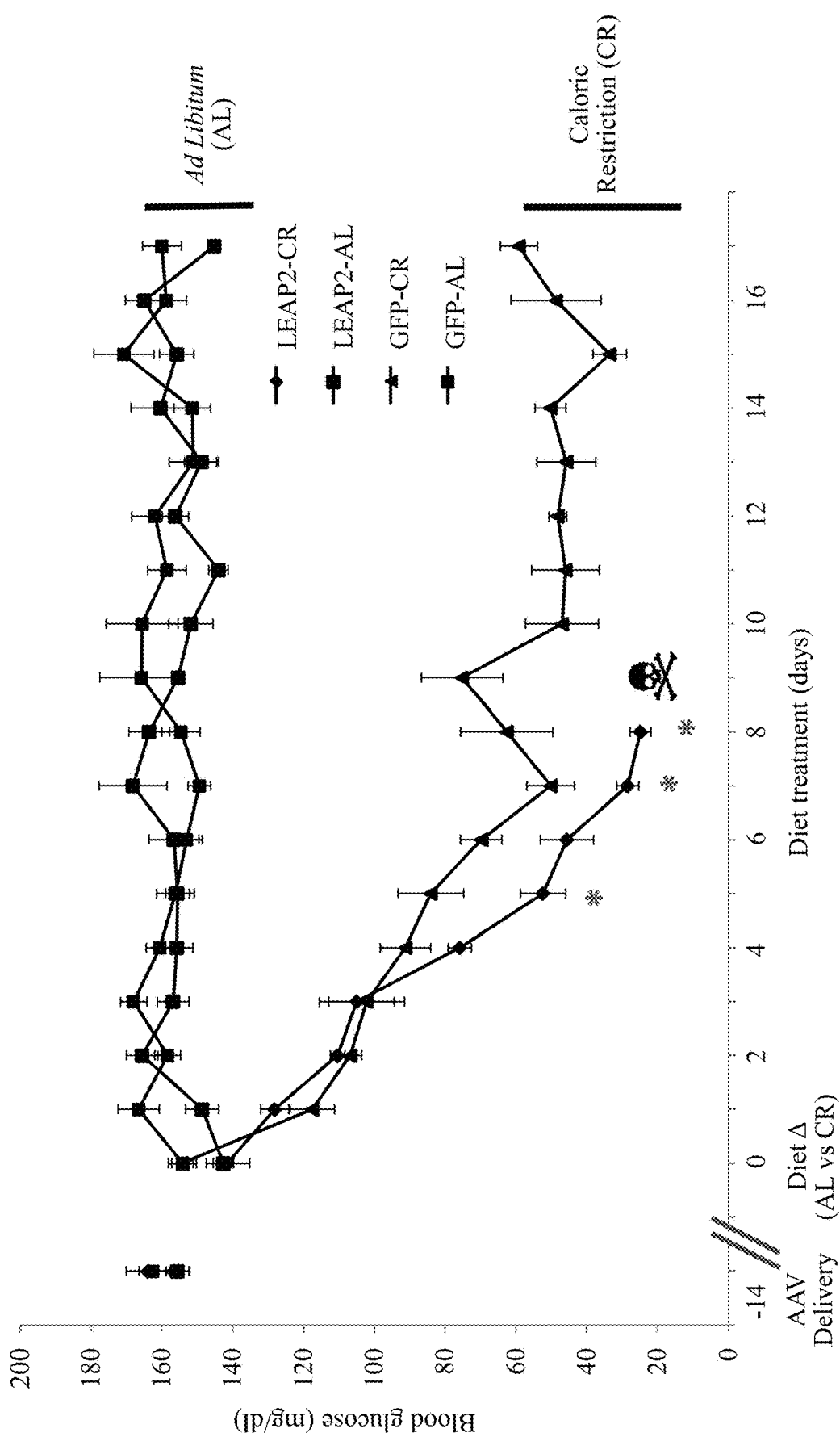
FIG. 7. Blood glucose levels in mice under conditions of chronic caloric restriction (CR) or free food intake (ad libitum; AL) in mice expressing LEAP2 or GFP.

As shown in FIG. 6A, subcutaneous administration of ghrelin at 0.15 µmol/kg was found to significantly promote food intake in mice at the 1 and 2 hour time points. Food intake was only slightly increased at the lower dose of 0.03 µmol/kg.

Figure 6B:
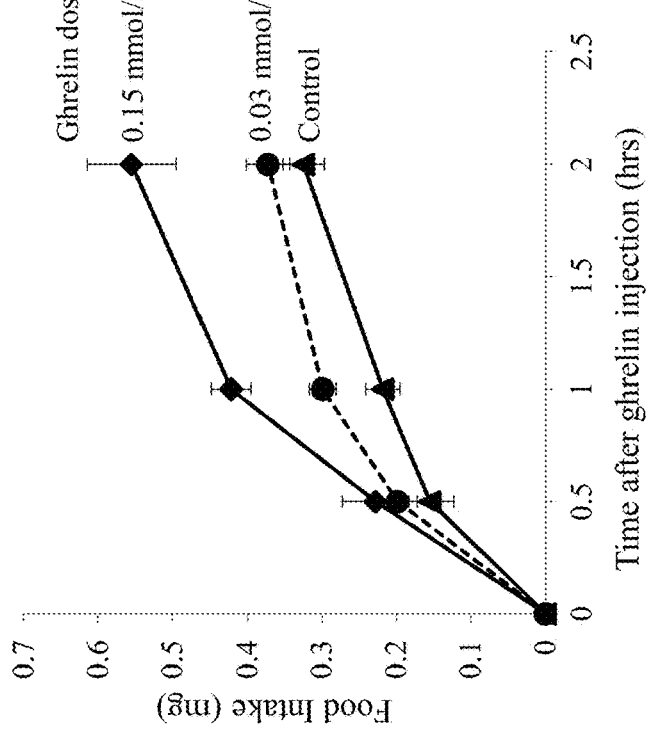

Next, to determine whether LEAP2 affects ghrelin-induced food intake, mice were pre-treated with LEAP2 peptide before being administered ghrelin. Mice were subcutaneously injected with 0.15 µmol/kg or 3 µmol/kg LEAP2. After 20 minutes, ghrelin was subcutaneously injected at a dose of 0.15 µmol/kg and food intake was measured at 0.5, 1, and 2 hours after ghrelin administration. Surprisingly, when mice were pre-treated with a high dose of LEAP2 peptide (3 µmol/kg) the increase in food intake induced by ghrelin was completely abolished (FIG. 6B). Mice treated with the same dose of LEAP2 peptide alone consumed significantly less food than vehicle-treated mice. These results suggest that LEAP2 antagonizes ghrelin and/or ghrelin activity. Low dose LEAP2 (0.15 µmol/kg) had no effect on ghrelin-induced food intake, nor did it affect food intake when administered alone. Taken together, these results suggest that LEAP2 inhibits and/or blocks ghrelin-induced food intake.

Example 9

Effect of LEAP2 Expression Under Diet Treatment Conditions

Recent studies in ghrelin-deficient mice revealed that a key physiological role of ghrelin is to maintain viable blood glucose levels during chronic calorie restriction (Li, et al., 2012, JBC, 287:17942-17950; Zhao, et al., 2010, PNAS, 107:7467-7472). To evaluate the effect of LEAP2 during such a physiological challenge, a mouse model of chronic calorie restriction (CR) was set up.

An adeno-associated virus (AAV) 'minigene' system was employed to drive lasting systemic expression of LEAP2 or a control (secreted GFP) in CR and AL mice (Galon-Tilleman, et al., 2017, JBC, 292:1925-1933). The method of producing and purifying AAV is as follows. AAV-293 cells were cultured in DMEM media supplemented with 10% fetal bovine serum and 1X antibiotic-antimycotic solution. Cells were plated at 50% density on day 1 in 150 mm cell culture plates and transfected after day 2, using the calcium phosphate precipitation method. The plasmids (20 µg/plate of each) were (i) AAV-LEAP2 or AAV-GFP, (ii) pHelper plasmids, and (iii) AAV2/9 plasmid. 48 hours after transfection, the cells were scraped off the plates, pelleted by centrifugation at 3000 xg, and resuspended in buffer containing 20 mM Tris pH 8.5, 100 mM NaCl and 1 mM $MgCl_2$. The cell suspension was frozen in an alcohol dry ice bath and then thawed in a 37° C. water bath. The freeze and thaw cycles were repeated for a total of three times. Benzonase (Sigma-Aldrich) was added to 50 units/mL and deoxycholate was added to a final concentration of 0.25%. After an incubation at 37° C. for 30 min, cell debris was removed by centrifugation at 5000 xg for 20 min. Viral particles in the supernatant were purified using a discontinuous iodixanol gradient as previously described (Zolotukhin, 1999, Gene Ther., 6:973-985). The viral stock was concentrated using Vivaspin 20 (MW cutoff 100,000 Dalton, Sartorius Stedim Biotech) and re-suspended in PBS with 10% glycerol and stored at −80° C. To determine the viral genome copy number, 2 µl of viral stock was incubated in 6 µl of solution containing 50 units/ml benzonase, 50 mM Tris-HCl pH 7.5, 10 mM $MgCl_2$ and 10 mM $CaCl_2$ for at 37° C. for 30 min. 15 µl of the solution containing 2 mg/mL of Proteinase K, 0.5% SDS, and 25 mM EDTA were added and the mixture was incubated for additional 20 min at 55° C. to release viral DNA. Viral DNA was purified using a mini DNeasy Kit (Qiagen) and eluted with 40 µl of water. Viral genome copy was determined using quantitative PCR. Viral stocks were diluted with phosphate buffered saline (PBS) to the desired concentration. 200 µl of viral working solution was delivered into mice via tail vein injection.

Mice were injected with AAV-LEAP2 or AAV-GFP, kept in individual cages, and fed chow diet ad libitum (AL) for 2 weeks. 2 weeks after injection AAV-LEAP2 was found to increase circulating LEAP2 levels by 3-fold. Baseline measurements of all mice were taken to assess body weight and blood glucose. Food intake was monitored daily to determine baseline food intake. Thereafter, the mice were separated into four groups. The GFP-AL and LEAP2-AL groups continued to receive the chow diet ad libitum. Mice in the GFP-CR and LEAP2-CR groups were fed 40% of the daily food intake consumed by the same mouse during the baseline period. Body weight and blood glucose were measured daily, immediately before feeding.

After one week of calorie restriction, both GFP- and LEAP2-expressing mice lost about 28% of their body weight. As shown in FIG. 7, blood glucose levels declined within the first week in both CR groups. GFP-expressing mice in the CR group had blood glucose levels that remained relatively constant at approximately 50 mg/dL after day 8. In contrast, LEAP2-expressing mice in the CR group had blood glucose levels that continued to decline until they dropped below 30 mg/dL. While GFP-expressing mice undergoing calorie restriction appeared active and healthy throughout the course of the experiment, LEAP2-expressing mice undergoing calorie restriction were too moribund and lethargic to consume their food by day 8. These mice were euthanized in accordance with institutional animal care and use guidelines. Body weight measurements of the mice in these treatment groups paralleled the blood glucose results (data not shown).

These results suggested that over-expression of LEAP2 leads to lack of survival under chronic calorie restriction.

At the end of the experiment, ghrelin and growth hormone levels were assessed. Circulating levels of ghrelin were approximately 8-fold higher in the blood of GFP-expressing mice under calorie-restricted conditions as compared with GFP-expressing control mice under ad libitum conditions. Interestingly, although calorie restriction also increased circulating ghrelin levels in LEAP2-expressing mice, the fold increase was much lower than in GFP-expressing mice under calorie-restricted conditions. Under ad libitum conditions, growth hormone levels were low in both GFP- and LEAP2-expressing mice. Calorie restriction increased growth hormone levels, but the growth hormone levels were higher in GFP-expressing mice than LEAP2-expressing mice.

These results suggested that inhibition of ghrelin by LEAP2 may prevent maximal release of growth hormone. Decreased growth hormone production may lead to hypoglycemia and ultimately lack of survival in the face of calorie restriction.

It was found that calorie restriction depleted body fat in all four groups, as indicted by magnetic resonance imaging (MRI). Both the GFP- and LEAP2-expressing groups of mice exhibited significant decreases in fat mass (losing ~54% of their fat mass) rather than lean mass, indicating that calorie restriction burns body fat but has minimal effect on lean mass. Consequently, the levels of free fatty acids and ketone bodies decreased dramatically in both the GFP- and LEAP2-expressing mice at the end of the calorie restriction treatment.

Previous studies have shown that under calorie-restricted conditions, the main source of blood glucose is gluconeogenesis, a process dependent on growth hormone. To further evaluate the involvement of growth hormone in LEAP2-mediated hypoglycemia during chronic calorie restriction, growth hormone was continuously delivered to calorie-restricted mice.

As described above, two weeks before initiation of calorie restriction, 2-3 month-old male mice were administered AAV-LEAP2 or AAV-GFP by tail vein injection. Diet treatment groups and measurements were the same as above. For growth hormone infusion, Alzet® osmotic mini-pumps filled with recombinant rat growth hormone (GroPep Bioreagents) or vehicle were implanted subcutaneously in the interscapular region. Growth hormone concentration in the pumps was 2 mg/ml and the growth hormone was delivered at a rate of 0.25 µl/hr (0.5 µg/hr).

Figure 8A:
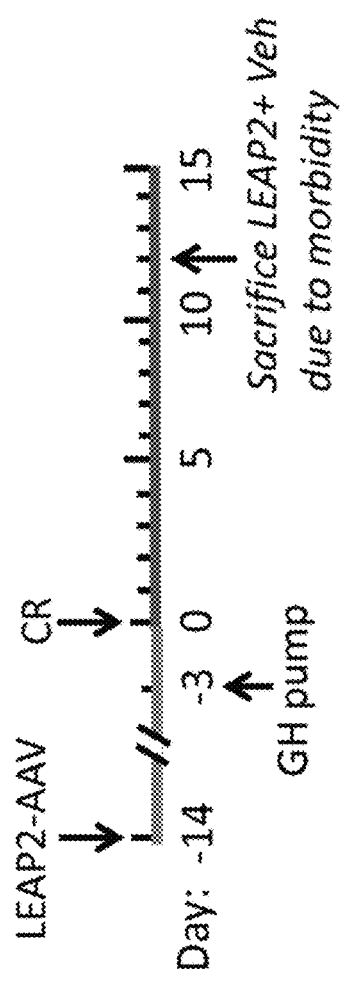
FIGS. 8A-8C.
Figure 8C:
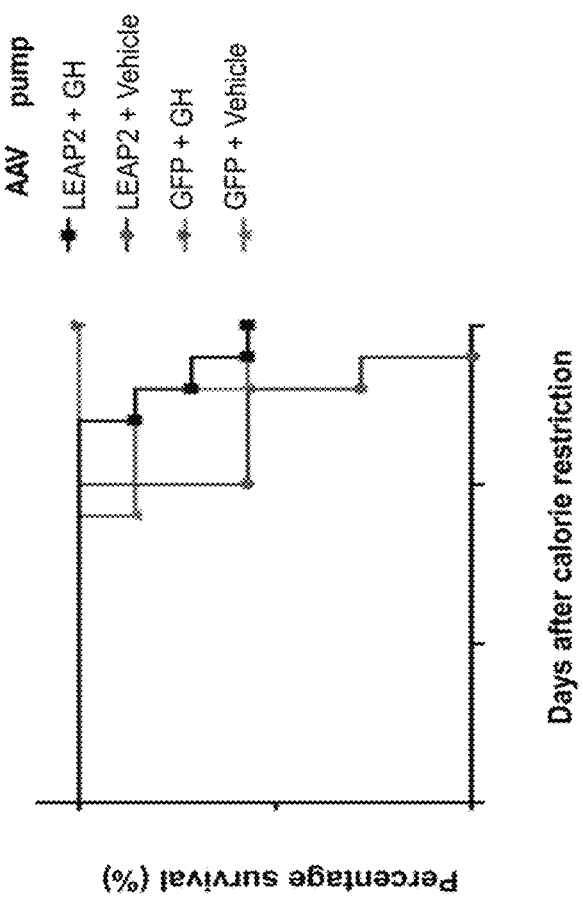
Figure 8B:
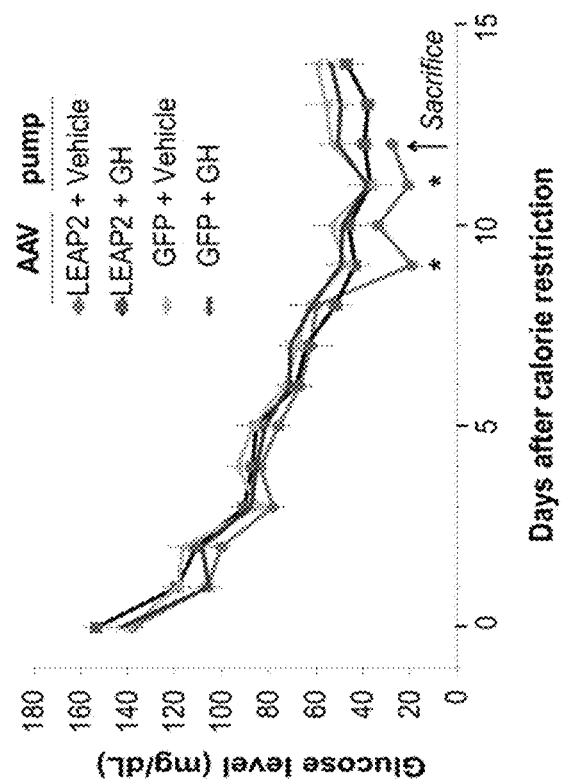
Figure 11B:
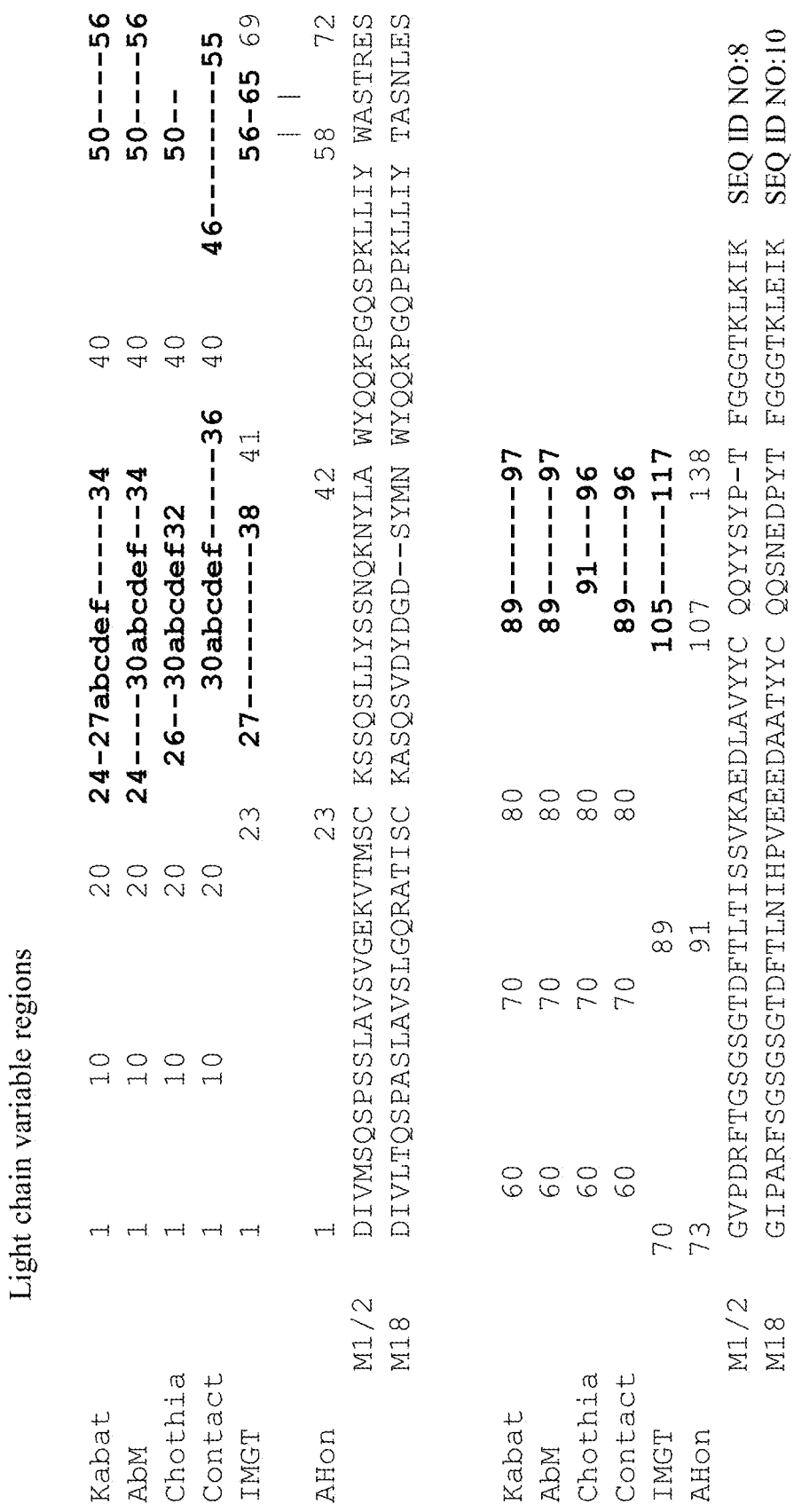

FIG. 8A illustrates the experimental design for growth hormone infusion during chronic calorie restriction. The delivery efficiency of growth hormone was confirmed in a separate group of naïve mice kept in ad libitum conditions over 2 weeks. FIG. 9A shows serum levels of growth hormone, demonstrating that the Alzet pump stably and efficiently delivered growth hormone. Osmotic pumps were implanted 3 days before initiation of calorie restriction. As shown in FIG. 8B, glucose levels decreased in all groups during calorie restriction with little difference in mice receiving growth hormone as compared to mice receiving vehicle. In LEAP2-expressing mice implanted with growth hormone pumps, 60% were able to maintain stable levels of blood glucose and survived to the end of the experiment. In contrast, LEAP2-expressing mice not receiving growth hormone failed to maintain viable glucose levels and the entire group had to be euthanized by day 12. FIG. 8C presents a Kaplan-Meier survival curve of the mice from this experiment.

FIGS. 9B-9E show additional data of the above study. FIGS. 9B-9D show blood levels of LEAP2, growth hormone, and ghrelin at the end of the experiment. FIG. 9E shows the ratio of fat mass or lean mass to body weight at the end of the study. These results demonstrated that body fat was decreased over the course of chronic calorie restriction and that delivery of growth hormone had no effect.

These data suggested that delivery of growth hormone bypasses LEAP2 inhibition of ghrelin-induced GHSR activity. This allowed for survival of LEAP2-expressing mice in the face of calorie restriction.

Example 10

Anti-LEAP2 Antibody Generation

To evaluate loss of endogenous LEAP2 function in adult mice, LEAP2 neutralizing monoclonal antibodies were developed. Anti-LEAP2 antibodies were generated using mouse hybridoma technology. Briefly, synthetic LEAP2 peptide was conjugated to bovine serum albumin carrier protein and used to immunize NZB/NZW and BALB/c mice. Following measurement of positive antibody titers, spleens were harvested from immunized mice and spleen cells were fused with myeloma cells to generate hybridomas. Individual hybridoma clones were isolated and hybridoma supernatants were screened for binding to LEAP2 peptide by ELISA. Positive hybridoma clones were scaled up and antibodies were purified from hybridoma culture supernatant using two-dimensional chromatography implemented on an AKTA™ Pure chromatography system (GE Healthcare Life Sciences). Briefly, the hybridoma media was clarified by centrifugation (6000×g, 15 min), filtered through a 0.22 μm filter, and pH adjusted by addition of 1/20 volume of a neutralizing stock solution (500 mM Tris pH 8.0, 400 mM NaCl, 20 mM EDTA). The antibodies were captured on a 5 mL MabSelect SuRe™ column (GE Healthcare Life Sciences), washed in PBS (20 column volumes), and eluted with 100 mM acetic acid, 100 mM NaCl, pH 3.5 onto a 10 mL sample collection loop. Immediately after elution, the eluted protein was reinjected onto a Superdex 200 pg 26/600 size-exclusion column (GE Healthcare Life Sciences) equilibrated in PBS buffer. For each antibody, the fractions corresponding to the monomeric peak were pooled together. Protein purity was assessed by SDS-PAGE. The hydrodynamic properties of the purified antibodies were analyzed by HPLC (Agilent 1200) equipped with a Yarra™ 3000 column. Samples were compared to molecular weight standards.

Approximately 2000 hybridoma clones were screened by ELISA and 25 clones were identified as producing antibodies capable of binding LEAP2. These 25 anti-LEAP2 antibodies were screened for their ability to block LEAP2 inhibition of ghrelin-induced GHSR activity. Each individual antibody was mixed with LEAP2 and assayed in an antagonist format using the GHSR-stable cell line described herein as illustrated in FIG. 10A. While a control antibody had no impact on LEAP2 inhibition of GHSR activity, anti-LEAP2 antibodies reversed the inhibition as shown by exemplary antibodies M2 and M18 (FIG. 10B). Antibodies M2 and M18 blocked LEAP2 inhibition of GHSR activity (EC50 of M2=0.17 μM and EC50 of M18=0.68 μM). The monoclonal antibody referred to herein as "M1/M2" refers to an exemplary antibody that represents two hybridomas (M1 and M2) that were found to have identical sequences. The two anti-LEAP2 monoclonal antibodies, M1/M2 and M18, were chosen for further studies.

The effect of blocking endogenous LEAP2 on ghrelin's activity in vivo was investigated. To study this biological activity under the most physiological conditions possible, mice were challenged through fasting, which stimulates ghrelin secretion in rodents. Growth hormone release is an important physiological response induced by ghrelin and is very sensitive to changes in ghrelin levels, thus this parameter was used as the assay readout.

FIG. 10C illustrates the experimental design for evaluating the impact of anti-LEAP2 antibodies on growth hormone release. Following a 24 hour fasting period, a baseline blood sample was taken, and anti-LEAP2 antibodies (10 mg/kg) were administered by intraperitoneal injection. Growth hormone levels were determined at 5, 10, 30, 60, 90, and 120 minutes post-injection.

As shown in FIG. 10D, anti-LEAP2 antibodies M2 and M18 increased the peak of growth hormone secretion as compared to a control antibody. Antibodies M2 and M18 increased the total amount of growth hormone released as determined by AUC (FIG. 10E).

These data indicated that blocking LEAP2 function increases fasting-induced ghrelin responses that lead to increased growth hormone release. Importantly, the results demonstrate that blocking endogenous LEAP2 promotes ghrelin-induced GHSR activity in vivo.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

All publications, patents, patent applications, internet sites, and accession numbers/database sequences including both polynucleotide and polypeptide sequences cited herein are hereby incorporated by reference in their entirety for all purposes to the same extent as if each individual publication, patent, patent application, internet site, or accession number/database sequence were specifically and individually indicated to be so incorporated by reference.

Following are the sequences disclosed in the application with the exception of the CDR sequences defined in Tables 1 and 2 (SEQ ID NOs:20-67).

```
Human LEAP2
                                                          (SEQ ID NO: 1)
MWHLKLCAVLMIFLLLLGQIDGSPIPEVSSAKRRPRRMTPFWRGVSLRPIGASCRDDSEC
ITRLCRKRRCSLSVAQE Mature peptide of human LEAP2
                                                          (SEQ ID NO: 2)
MTPFWRGVSLRPIGASCRDDSECITRLCRKRRCSLSVAQE Amino acids 44-55 of human LEAP2
                                                          (SEQ ID NO: 3)
GVSLRPIGASCR Amino acids 44-63 of human LEAP2
                                                          (SEQ ID NO: 4)
GVSLRPIGASCRDDSECITR
```

-continued

```
Human GHSR1a
                                                             (SEQ ID NO: 5)
MWNATPSEEPGFNLTLADLDWDASPGNDSLGDELLQLFPAPLLAGVTATCVALFVVGIAG

NLLTMLVVSRFRELRTTTNLYLSSMAFSDLLIFLCMPLDLVRLWQYRPWNFGDLLCKLFQ

FVSESCTYATVLTITALSVERYFAICFPLRAKVVVTKGRVKLVIFVIWAVAFCSAGPIFV

LVGVEHENGTDPWDTNECRPTEFAVRSGLLTVMVWVSSIFFFLPVFCLTVLYSLIGRKLW

RRRRGDAVVGASLRDQNHKQTVKMLAVVVFAFILCWLPFHVGRYLFSKSFEPGSLEIAQI

SQYCNLVSFVLFYLSAAINPILYNIMSKKYRVAVFRLLGFEPFSQRKLSTLKDESSRAWT

ESSINT

Human GHSR1b
                                                             (SEQ ID NO: 6)
MWNATPSEEPGFNLTLADLDWDASPGNDSLGDELLQLFPAPLLAGVTATCVALFVVGIAG

NLLTMLVVSRFRELRTTTNLYLSSMAFSDLLIFLCMPLDLVRLWQYRPWNFGDLLCKLFQ

FVSESCTYATVLTITALSVERYFAICFPLRAKVVVTKGRVKLVIFVIWAVAFCSAGPIFV

LVGVEHENGTDPWDTNECRPTEFAVRSGLLTVMVWVSSIFFFLPVFCLTVLYSLIGRKLW

RRRRGDAVVGASLRDQNHKQTVKMLGGSQRALRLSLAGPILSLCLLPSL

M1/M2 Heavy chain variable region
                                                             (SEQ ID NO: 7)
EVQLQQSGTVLARPGASVKMSCKASGYTFTSYWMHWVKQRPGQGLEWIGAIYPGNSDTSY
KQKFKGKAKLTAVTSASTVYMELSSLTDEDSAVYYCTYGKEEYLFAMDYWGQGTSVTVSS M1/M2 Light chain variable region
                                                             (SEQ ID NO: 8)
DIVMSQSPSSLAVSVGEKVTMSCKSSQSLLYSSNQKNYLAWYQQKPGQSPKLLIYWASTR
ESGVPDRFTGSGSGTDFTLTISSVKAEDLAVYYCQQYYSYPTFGGGTKLKIK M18 Heavy chain variable region
                                                             (SEQ ID NO: 9)
EIQLQQSGPELMKPGASVKISCKASGYSFTNYYIHWVKQSHGKSLEWIGYIDPFNGGTNY
NQKFKGKATLTVDKSSSTAYMHLSSLTFEDSAVYYCARRGYYYGFTYWGQGTLVTVSA M18 Light chain variable region
                                                             (SEQ ID NO: 10)
DIVLTQSPASLAVSLGQRATISCKASQSVDYDGDSYMNWYQQKPGQPPKLLIYTASNLESGIPARFSGSG
SGTDFTLNIHPVEEEDAATYYCQQSNEDPYTFGGGTKLEIK Chimpanzee LEAP2
                                                             (SEQ ID NO: 11)
MWHLKLCAVLMIFLLLLGQIDGSPIPEVSSAKRRPRRMTPFWRGVSLRPIGASCRDDSEC
ITRLCRKRRCSLSVAQE Rhesus macaque LEAP2
                                                             (SEQ ID NO: 12)
MWHLKLCAVLMIFLLLLGQTDGSPIPEVSSAKRRPRRMTPFWRGVSLRPIGASCRDDSEC
ITRLCRKRRCSLSVAQE Cynomolgus monkey
                                                             (SEQ ID NO: 13)
MWHLKLCAVLMIFLLLLGQTDGSPIPEVSSAKRRPRRMTPFWRGVSLRPIGASCRDDSEC
ITRLCRKRRCSLSVAQE Guinea pig LEAP2
                                                             (SEQ ID NO: 14)
SVVLLICLLLLGQVDGSPVPEKSSVKKRLRRMTPFWRGVSLRPIGASCRDDSECITRLCK
KRRCSLSVAQE Cow LEAP2
                                                             (SEQ ID NO: 15)
MWHLKLFAVLMICLLLLAQVDGSPIPQQSSAKRRPRRMTPFWRAVSLRPIGASCRDDSEC
ITRLCRKRRCSLSVAQE Mouse LEAP2
                                                             (SEQ ID NO: 16)
MLQLKLFAVLLTCLLLLGQVNSSPVPEVSSAKRSRRMTPFWRGVSLRPIGASCRDDSECI
TRLCRKRRCSLSVAQE
```

-continued

Rabbit LEAP2
(SEQ ID NO: 17)
MWHLKLFAVLMICLLLLGQVDGSPVPELSSAKRRPRRMTPFWRGVSLRPIGASCRDNAEC
VTRLCRKRRCSLSVAQE Rat LEAP2
(SEQ ID NO: 18)
LQLKLFAVLLTCLLLLGQAQSSPVPELSSAKRTRRMTPFWRGVSLRPIGASCRDDSECIT
RLCKRRRCSLSVAQE Chicken LEAP2
(SEQ ID NO: 19)
MHCLKIMAFLLFFSLLLSQVCCASLHQPQPLLRLKRMTPFWRGVSLRPVGASCRDNSECI
TMLCRKNRCFLRTASE Human IgG1 Heavy chain constant region
(SEQ ID NO: 68)
ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFFLYSKLTVDKSRW

QQGNVFSCSVMHEALHNHYTQKSLSLSPGK

Human IgG4 Heavy chain constant region
(SEQ ID NO: 69)
ASTKGPSVFPLAPCSRSTSESTAALGCLVKDYFPEPVTVSWNSGALTSGVHTFPAVLQSS

GLYSLSSVVTVPSSSLGTKTYTCNVDHKPSNTKVDKRVESKYGPPCPSCPAPEFLGGPSV

FLFPPKPKDTLMISRIPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYTLPPSQEEMTK

NQVSLTCLVKGFYPSDIAVEWESNGQPENNYKTTPPVLDSDGSFFLYSRLTVDKSRWQEG

NVFSCSVMHEALHNHYTQKSLSLSLGK

Human IgG1 Heavy chain constant region E233A/L235A
(SEQ ID NO: 70)
ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPALAGG

PSVFLFPPKPKDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQVYTLPPSREE

MTKNQVSLTCLVKGFYPSDIAVEWESNGQPENNYKTTPPVLDSDGSFFLYSKLTVDKSRW

QQGNVFSCSVMHEALHNHYTQKSLSLSPGK

Human IgG1 Heavy chain constant region E233A/L235A/ΔK447
(SEQ ID NO: 71)
ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPALAGG

PSVFLFPPKPKDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQVYTLPPSREE

MTKNQVSLTCLVKGFYPSDIAVEWESNGQPENNYKTTPPVLDSDGSFFLYSKLTVDKSRW

QQGNVFSCSVMHEALHNHYTQKSLSLSPG

Human IgG1 Heavy chain constant region ΔK447
(SEQ ID NO: 72)
ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQVYTLPPSRDE

LTKNQVSLTCLVKGFYPSDIAVEWESNGQPENNYKTTPPVLDSDGSFFLYSKLTVDKSRW

QQGNVFSCSVMHEALHNHYTQKSLSLSPG

Human IgG1 Heavy chain constant region N297Q
(SEQ ID NO: 73)
ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPELLGG

PSVFLFPPKPKDTLMISRTPEVTCVVVDVSHEDPEVKFNWYVDGVEVHNAKTKPREEQYQ

STYRVVSVLTVLHQDWLNGKEYKCKVSNKALPAPIEKTISKAKGQPREPQVYTLPPSREE

MTKNQVSLTCLVKGFYPSDIAVEWESNGQPENNYKTTPPVLDSDGSFFLYSKLTVDKSRW

QQGNVFSCSVMHEALHNHYTQKSLSLSPGK

Human IgG1 constant region L234A/L235A
(SEQ ID NO: 74)
ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPEAAGG

PSVFLFPPKPKDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQVYTLPPSREE

MTKNQVSLTCLVKGFYPSDIAVEWESNGQPENNYKTTPPVLDSDGSFFLYSKLTVDKSRW

QQGNVFSCSVMHEALHNHYTQKSLSLSPGK

Human IgG1 constant region L234A/L235A/P329G
(SEQ ID NO: 75)
ASTKGPSVFPLAPSSKSTSGGTAALGCLVKDYFPEPVTVSWNSGALTSGVHTFPAVLQSS

GLYSLSSVVTVPSSSLGTQTYICNVNHKPSNTKVDKKVEPKSCDKTHTCPPCPAPEAAGG

PSVFLFPPKPKDTLMISRTPEVTCVVVDVSHEDPEVKFNWYVDGVEVHNAKTKPREEQYN

STYRVVSVLTVLHQDWLNGKEYKCKVSNKALGAPIEKTISKAKGQPREPQVYTLPPSREE

MTKNQVSLTCLVKGFYPSDIAVEWESNGQPENNYKTTPPVLDSDGSFFLYSKLTVDKSRW

QQGNVFSCSVMHEALHNHYTQKSLSLSPGK

Human IgG4 Heavy chain constant region S228P
(SEQ ID NO: 76)
ASTKGPSVFPLAPCSRSTSESTAALGCLVKDYFPEPVTVSWNSGALTSGVHTFPAVLQSS

GLYSLSSVVTVPSSSLGTKTYTCNVDHKPSNTKVDKRVESKYGPPCPPCPAPEFLGGPSV

FLFPPKPKDTLMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYTLPPSQEEMTK

NQVSLTCLVKGFYPSDIAVEWESNGQPENNYKTTPPVLDSDGSFFLYSRLTVDKSRWQEG

NVFSCSVMHEALHNHYTQKSLSLSLGK

Human IgG4 Heavy chain constant region S228P/ΔK447
(SEQ ID NO: 77)
ASTKGPSVFPLAPCSRSTSESTAALGCLVKDYFPEPVTVSWNSGALTSGVHTFPAVLQSS

GLYSLSSVVTVPSSSLGTKTYTCNVDHKPSNTKVDKRVESKYGPPCPPCPAPEFLGGPSV

FLFPPKPKDTLMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYTLPPSQEEMTK

NQVSLTCLVKGFYPSDIAVEWESNGQPENNYKTTPPVLDSDGSFFLYSRLTVDKSRWQEG

NVFSCSVMHEALHNHYTQKSLSLSLG

Human IgG4 Heavy chain constant region ΔK447
(SEQ ID NO: 78)
ASTKGPSVFPLAPCSRSTSESTAALGCLVKDYFPEPVTVSWNSGALTSGVHTFPAVLQSS

GLYSLSSVVTVPSSSLGTKTYTCNVDHKPSNTKVDKRVESKYGPPCPSCPAPEFLGGPSV

-continued

FLFPPKPKDTLMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYTLPPSQEEMTK

NQVSLTCLVKGFYPSDIAVEWESNGQPENNYKTTPPVLDSDGSFFLYSRLTVDKSRWQEG

NVFSCSVMHEALHNHYTQKSLSLSLGK

---

The invention claimed is:

1. A method of treating a wasting syndrome in a human subject, the method comprising administering to the human subject a therapeutically effective amount of an antibody that specifically binds liver-expressed antimicrobial peptide 2 (LEAP2), wherein the antibody comprises: (1) a first heavy chain variable region (VH) comprising a first VH complementarity determining region (CDR)1, a first VH CDR2, and a first VH CDR3 from the amino acid sequence of SEQ ID NO:7 and a first light chain variable region (VL) comprising a first VL CDR1, a first VL CDR2, and a first VL CDR3 from the amino acid sequence of SEQ ID NO: 8; or (2) a second VH comprising a second VH CDR1, a second VH CDR2, and a second VH CDR3 from the amino acid sequence of SEQ ID NO:9 and a second VL comprising a second VL CDR1, a second VL CDR2, and a second VL CDR3 from the amino acid sequence of SEQ ID NO: 10.

2. The method of claim 1, wherein the antibody is an antibody fragment comprising at least one antigen-binding site.

3. The method of claim 1, wherein the antibody is a monoclonal antibody, a chimeric antibody, a humanized antibody, a bispecific antibody, a multispecific antibody, a Fab, Fab', F(ab')$_2$, Fv, scFv, (scFv)$_2$, a single chain antibody, or a dual variable region antibody.

4. The method of claim 1, wherein the antibody is an IgG1 antibody, an IgG2 antibody, or an IgG4 antibody.

5. The method of claim 1, wherein the antibody:
(i) is an antagonist of LEAP2;
(ii) inhibits the binding of LEAP2 to GHSR; and/or
(iii) increases food intake.

6. The method of claim 1, wherein: (1) the first VH has least 90% sequence identity to the amino acid sequence of SEQ ID NO:7 and the first VL has at least 90% identity to the amino acid sequence of SEQ ID NO:8, or (2) the second VH has at least 90% sequence identity to the amino acid sequence of SEQ ID NO:9 and the second VL has at least 90% identity to the amino acid sequence of SEQ ID NO:10.

7. The method of claim 1, wherein: (1) the first VH comprises the amino acid sequence of SEQ ID NO:7 and the first VL comprises the amino acid sequence of SEQ ID NO:8, or (2) the second VH comprises the amino acid sequence of SEQ ID NO: 9 and the second VL comprises the amino acid sequence of SEQ ID NO:10.

8. The method of claim 7, wherein the antibody is an IgG1 antibody, an IgG2 antibody, or an IgG4 antibody.

9. The method of claim 1, wherein the antibody is humanized.

10. The method of claim 1, wherein the wasting syndrome is anorexia.

11. The method of claim 1, wherein the wasting syndrome is cachexia.

12. The method of claim 1, wherein:
(a) the first VH CDR1 comprises the amino acid sequence of SEQ ID NO:20, the first VH CDR2 comprises the amino acid sequence of SEQ ID NO:21, the first VH CDR3 comprises the amino acid sequence of SEQ ID NO:22, the first VL CDR1 comprises the amino acid sequence of SEQ ID NO:23, the first VL CDR2 comprises the amino acid sequence of SEQ ID NO:24, and the first VL CDR3 comprises the amino acid sequence of SEQ ID NO:25;
(b) the first VH CDR1 comprises the amino acid sequence of SEQ ID NO:32, the first VH CDR2 comprises the amino acid sequence of SEQ ID NO:36, the first VH CDR3 comprises the amino acid sequence of SEQ ID NO:40, the first VL CDR1 comprises the amino acid sequence of SEQ ID NO:43, the first VL CDR2 comprises the amino acid sequence of SEQ ID NO:46, and the first VL CDR3 comprises the amino acid sequence of SEQ ID NO:25;
(c) the first VH CDR1 comprises the amino acid sequence of SEQ ID NO:33, the first VH CDR2 comprises the amino acid sequence of SEQ ID NO:21, the first VH CDR3 comprises the amino acid sequence of SEQ ID NO:22, the first VL CDR1 comprises the amino acid sequence of SEQ ID NO:23, the first VL CDR2 comprises the amino acid sequence of SEQ ID NO:24, and the first VL CDR3 comprises the amino acid sequence of SEQ ID NO:25;
(d) the first VH CDR1 comprises the amino acid sequence of SEQ ID NO:34, the first VH CDR2 comprises the amino acid sequence of SEQ ID NO:37, the first VH CDR3 comprises the amino acid sequence of SEQ ID NO:41, the first VL CDR1 comprises the amino acid sequence of SEQ ID NO:44, the first VL CDR2 comprises the amino acid sequence of SEQ ID NO:46, and the first VL CDR3 comprises the amino acid sequence of SEQ ID NO:48;
(e) the first VH CDR1 comprises the amino acid sequence of SEQ ID NO:35, the first VH CDR2 comprises the amino acid sequence of SEQ ID NO:38, the first VH CDR3 comprises the amino acid sequence of SEQ ID NO:42, the first VL CDR1 comprises the amino acid sequence of SEQ ID NO:45, the first VL CDR2 comprises the amino acid sequence of SEQ ID NO:47, and the first VL CDR3 comprises the amino acid sequence of SEQ ID NO:49; or
(f) the first VH CDR1 comprises the amino acid sequence of SEQ ID NO:20, the first VH CDR2 comprises the amino acid sequence of SEQ ID NO:39, the first VH CDR3 comprises the amino acid sequence of SEQ ID NO:22, the first VL CDR1 comprises the amino acid sequence of SEQ ID NO:23, the first VL CDR2 comprises the amino acid sequence of SEQ ID NO:24, and the first VL CDR3 comprises the amino acid sequence of SEQ ID NO:25;
  (g) the second VH CDR1 comprises the amino acid sequence of SEQ ID NO:26, the second VH CDR2 comprises the amino acid sequence of SEQ ID NO:27, the second VH CDR3 comprises the amino acid sequence of SEQ ID NO:28, the second VL CDR1 comprises the amino acid sequence of SEQ ID NO:29, the second VL CDR2 comprises the amino acid sequence of SEQ ID NO:30, and the second VL CDR3 comprises the amino acid sequence of SEQ ID NO:31;
  (h) the second VH CDR1 comprises the amino acid sequence of SEQ ID NO:50, the second VH CDR2 comprises the amino acid sequence of SEQ ID NO:54, the second VH CDR3 comprises the amino acid sequence of SEQ ID NO:58, the second VL CDR1 comprises the amino acid sequence of SEQ ID NO:61, the second VL CDR2 comprises the amino acid sequence of SEQ ID NO:64, and the second VL CDR3 comprises the amino acid sequence of SEQ ID NO:31;
  (i) the second VH CDR1 comprises the amino acid sequence of SEQ ID NO:51, the second VH CDR2 comprises the amino acid sequence of SEQ ID NO:27, the second VH CDR3 comprises the amino acid sequence of SEQ ID NO:28, the second VL CDR1 comprises the amino acid sequence of SEQ ID NO:29, the second VL CDR2 comprises the amino acid sequence of SEQ ID NO:30, and the second VL CDR3 comprises the amino acid sequence of SEQ ID NO:31;
  (j) the second VH CDR1 comprises the amino acid sequence of SEQ ID NO:52, the second VH CDR2 comprises the amino acid sequence of SEQ ID NO:55, the second VH CDR3 comprises the amino acid sequence of SEQ ID NO:59, the second VL CDR1 comprises the amino acid sequence of SEQ ID NO:62, the second VL CDR2 comprises the amino acid sequence of SEQ ID NO:64, and the second VL CDR3 comprises the amino acid sequence of SEQ ID NO:66;
  (k) the second VH CDR1 comprises the amino acid sequence of SEQ ID NO:53, the second VH CDR2 comprises the amino acid sequence of SEQ ID NO:56, the second VH CDR3 comprises the amino acid sequence of SEQ ID NO:60, the second VL CDR1 comprises the amino acid sequence of SEQ ID NO:63, the second VL CDR2 comprises the amino acid sequence of SEQ ID NO:65, and the second VL CDR3 comprises the amino acid sequence of SEQ ID NO:67; or
  (l) the second VH CDR1 comprises the amino acid sequence of SEQ ID NO:26, the second VH CDR2 comprises the amino acid sequence of SEQ ID NO:57, the second VH CDR3 comprises the amino acid sequence of SEQ ID NO:28, the second VL CDR1 comprises the amino acid sequence of SEQ ID NO:29, the second VL CDR2 comprises the amino acid sequence of SEQ ID NO:30, and the second VL CDR3 comprises the amino acid sequence of SEQ ID NO:31.

13. A method of increasing growth hormone levels in a human subject, the method comprising administering to the human subject a therapeutically effective amount of an antibody that specifically binds liver-expressed antimicrobial peptide 2 (LEAP2), wherein the antibody comprises: (1) a first heavy chain variable region (VH) comprising a first VH complementarity determining region (CDR)1, a first VH CDR2, and a first VH CDR3 from the amino acid sequence of SEQ ID NO:7 and a first light chain variable region (VL) comprising a first VL CDR1, a first VL CDR2, and a first VL CDR3 from the amino acid sequence of SEQ ID NO: 8; or (2) a second VH comprising a second VH CDR1, a second VH CDR2, and a second VH CDR3 from the amino acid sequence of SEQ ID NO:9 and a second VL comprising a second VL CDR1, a second VL CDR2, and a second VL CDR3 from the amino acid sequence of SEQ ID NO: 10.

14. The method of claim 13, wherein the antibody is an antibody fragment comprising at least one antigen-binding site.

15. The method of claim 13, wherein the antibody is a monoclonal antibody, a chimeric antibody, a humanized antibody, a bispecific antibody, a multispecific antibody, a Fab, Fab', F(ab')$_2$, Fv, scFv, (scFv)$_2$, a single chain antibody, or a dual variable region antibody.

16. The method of claim 13, wherein the antibody is an IgG1 antibody, an IgG2 antibody, or an IgG4 antibody.

17. The method of claim 13, wherein the antibody:
  (i) is an antagonist of LEAP2;
  (ii) inhibits the binding of LEAP2 to GHSR; and/or
  (iii) increases food intake.

18. The method of claim 13, wherein: (1) the first VH has least 90% sequence identity to the amino acid sequence of SEQ ID NO:7 and the first VL has at least 90% identity to the amino acid sequence of SEQ ID NO:8; or (2) the second VH has at least 90% sequence identity to the amino acid sequence of SEQ ID NO:9 and the second VL has at least 90% identity to the amino acid sequence of SEQ ID NO:10.

19. The method of claim 13, wherein: (1) the first VH comprises the amino acid sequence of SEQ ID NO:7 and the first VL comprises the amino acid sequence of SEQ ID NO:8; or (2) the second VH comprises the amino acid sequence of SEQ ID NO: 9 and the second VL comprises the amino acid sequence of SEQ ID NO:10.

20. The method of claim 19, wherein the antibody is an IgG1 antibody, an IgG2 antibody, or an IgG4 antibody.

21. The method of claim 13, wherein the antibody is humanized.

22. The method of claim 13, wherein:
  (a) the first VH CDR1 comprises the amino acid sequence of SEQ ID NO:20, the first VH CDR2 comprises the amino acid sequence of SEQ ID NO:21, the first VH CDR3 comprises the amino acid sequence of SEQ ID NO:22, the first VL CDR1 comprises the amino acid sequence of SEQ ID NO:23, the first VL CDR2 comprises the amino acid sequence of SEQ ID NO:24, and the first VL CDR3 comprises the amino acid sequence of SEQ ID NO:25;
  (b) the first VH CDR1 comprises the amino acid sequence of SEQ ID NO:32, the first VH CDR2 comprises the amino acid sequence of SEQ ID NO:36, the first VH CDR3 comprises the amino acid sequence of SEQ ID NO:40, the first VL CDR1 comprises the amino acid sequence of SEQ ID NO:43, the first VL CDR2 comprises the amino acid sequence of SEQ ID NO:46, and the first VL CDR3 comprises the amino acid sequence of SEQ ID NO:25;
  (c) the first VH CDR1 comprises the amino acid sequence of SEQ ID NO:33, the first VH CDR2 comprises the amino acid sequence of SEQ ID NO:21, the first VH CDR3 comprises the amino acid sequence of SEQ ID NO:22, the first VL CDR1 comprises the amino acid sequence of SEQ ID NO:23, the first VL CDR2 comprises the amino acid sequence of SEQ ID NO:24, and the first VL CDR3 comprises the amino acid sequence of SEQ ID NO:25;

(d) the first VH CDR1 comprises the amino acid sequence of SEQ ID NO:34, the first VH CDR2 comprises the amino acid sequence of SEQ ID NO:37, the first VH CDR3 comprises the amino acid sequence of SEQ ID NO:41, the first VL CDR1 comprises the amino acid sequence of SEQ ID NO:44, the first VL CDR2 comprises the amino acid sequence of SEQ ID NO:46, and the first VL CDR3 comprises the amino acid sequence of SEQ ID NO:48;

(e) the first VH CDR1 comprises the amino acid sequence of SEQ ID NO:35, the first VH CDR2 comprises the amino acid sequence of SEQ ID NO:38, the first VH CDR3 comprises the amino acid sequence of SEQ ID NO:42, the first VL CDR1 comprises the amino acid sequence of SEQ ID NO:45, the first VL CDR2 comprises the amino acid sequence of SEQ ID NO:47, and the first VL CDR3 comprises the amino acid sequence of SEQ ID NO:49; or (f) the first VH CDR1 comprises the amino acid sequence of SEQ ID NO:20, the first VH CDR2 comprises the amino acid sequence of SEQ ID NO:39, the first VH CDR3 comprises the amino acid sequence of SEQ ID NO:22, the first VL CDR1 comprises the amino acid sequence of SEQ ID NO:23, the first VL CDR2 comprises the amino acid sequence of SEQ ID NO:24, and the first VL CDR3 comprises the amino acid sequence of SEQ ID NO:25;

(g) the second VH CDR1 comprises the amino acid sequence of SEQ ID NO:26, the second VH CDR2 comprises the amino acid sequence of SEQ ID NO:27, the second VH CDR3 comprises the amino acid sequence of SEQ ID NO:28, the second VL CDR1 comprises the amino acid sequence of SEQ ID NO:29, the second VL CDR2 comprises the amino acid sequence of SEQ ID NO:30, and the second VL CDR3 comprises the amino acid sequence of SEQ ID NO:31;

(h) the second VH CDR1 comprises the amino acid sequence of SEQ ID NO:50, the second VH CDR2 comprises the amino acid sequence of SEQ ID NO:54, the second VH CDR3 comprises the amino acid sequence of SEQ ID NO:58, the second VL CDR1 comprises the amino acid sequence of SEQ ID NO:61, the second VL CDR2 comprises the amino acid sequence of SEQ ID NO:64, and the second VL CDR3 comprises the amino acid sequence of SEQ ID NO:31;

(i) the second VH CDR1 comprises the amino acid sequence of SEQ ID NO:51, the second VH CDR2 comprises the amino acid sequence of SEQ ID NO:27, the second VH CDR3 comprises the amino acid sequence of SEQ ID NO:28, the second VL CDR1 comprises the amino acid sequence of SEQ ID NO:29, the second VL CDR2 comprises the amino acid sequence of SEQ ID NO:30, and the second VL CDR3 comprises the amino acid sequence of SEQ ID NO:31;

(j) the second VH CDR1 comprises the amino acid sequence of SEQ ID NO:52, the second VH CDR2 comprises the amino acid sequence of SEQ ID NO:55, the second VH CDR3 comprises the amino acid sequence of SEQ ID NO:59, the second VL CDR1 comprises the amino acid sequence of SEQ ID NO:62, the second VL CDR2 comprises the amino acid sequence of SEQ ID NO:64, and the second VL CDR3 comprises the amino acid sequence of SEQ ID NO:66;

(k) the second VH CDR1 comprises the amino acid sequence of SEQ ID NO:53, the second VH CDR2 comprises the amino acid sequence of SEQ ID NO:56, the second VH CDR3 comprises the amino acid sequence of SEQ ID NO:60, the second VL CDR1 comprises the amino acid sequence of SEQ ID NO:63, the second VL CDR2 comprises the amino acid sequence of SEQ ID NO:65, and the second VL CDR3 comprises the amino acid sequence of SEQ ID NO:67; or (l) the second VH CDR1 comprises the amino acid sequence of SEQ ID NO:26, the second VH CDR2 comprises the amino acid sequence of SEQ ID NO:57, the second VH CDR3 comprises the amino acid sequence of SEQ ID NO:28, the second VL CDR1 comprises the amino acid sequence of SEQ ID NO:29, the second VL CDR2 comprises the amino acid sequence of SEQ ID NO:30, and the second VL CDR3 comprises the amino acid sequence of SEQ ID NO:31.

23. A method of increasing growth hormone secretagogue receptor (GHSR) activity in a human subject, the method comprising administering to the human subject a therapeutically effective amount of an antibody that specifically binds liver-expressed antimicrobial peptide 2 (LEAP2), wherein the antibody comprises: (1) a first heavy chain variable region (VH) comprising a first VH complementarity determining region (CDR)1, a first VH CDR2, and a first VH CDR3 from the amino acid sequence of SEQ ID NO:7 and a first light chain variable region (VL) comprising a first VL CDR1, a first VL CDR2, and a first VL CDR3 from the amino acid sequence of SEQ ID NO: 8; or (2) a second VH comprising a second VH CDR1, a second VH CDR2, and a second VH CDR3 from the amino acid sequence of SEQ ID NO:9 and a second VL comprising a second VL CDR1, a second VL CDR2, and a second VL CDR3 from the amino acid sequence of SEQ ID NO: 10.

24. The method of claim 23, wherein the antibody is an antibody fragment comprising at least one antigen-binding site.

25. The method of claim 23, wherein the antibody is a monoclonal antibody, a chimeric antibody, a humanized antibody, a bispecific antibody, a multispecific antibody, a Fab, Fab', F(ab')$_2$, Fv, scFv, (scFv)$_2$, a single chain antibody, or a dual variable region antibody.

26. The method of claim 23, wherein the antibody is an IgG1 antibody, an IgG2 antibody, or an IgG4 antibody.

27. The method of claim 23, wherein the antibody:
(i) is an antagonist of LEAP2;
(ii) inhibits the binding of LEAP2 to GHSR; and/or
(iii) increases food intake.

28. The method of claim 23, wherein: (1) the first VH has least 90% sequence identity to the amino acid sequence of SEQ ID NO:7 and the first VL has at least 90% identity to the amino acid sequence of SEQ ID NO:8; or (2) the second VH has at least 90% sequence identity to the amino acid sequence of SEQ ID NO:9 and the second VL has at least 90% identity to the amino acid sequence of SEQ ID NO:10.

29. The method of claim 23, wherein: (1) the first VH comprises the amino acid sequence of SEQ ID NO:7 and the first VL comprises the amino acid sequence of SEQ ID NO:8; or (2) the second VH comprises the amino acid sequence of SEQ ID NO: 9 and the second VL comprises the amino acid sequence of SEQ ID NO:10.

30. The method of claim 29, wherein the antibody is an IgG1 antibody, an IgG2 antibody, or an IgG4 antibody.

31. The method of claim 23, wherein the antibody is humanized.

32. The method of claim 23, wherein:
(a) the first VH CDR1 comprises the amino acid sequence of SEQ ID NO:20, the first VH CDR2 comprises the amino acid sequence of SEQ ID NO:21, the first VH CDR3 comprises the amino acid sequence of SEQ ID NO:22, the first VL CDR1 comprises the amino acid sequence of SEQ ID NO:23, the first VL CDR2 comprises the amino acid sequence of SEQ ID NO:24, and the first VL CDR3 comprises the amino acid sequence of SEQ ID NO:25;
(b) the first VH CDR1 comprises the amino acid sequence of SEQ ID NO:32, the first VH CDR2 comprises the amino acid sequence of SEQ ID NO:36, the first VH CDR3 comprises the amino acid sequence of SEQ ID NO:40, the first VL CDR1 comprises the amino acid sequence of SEQ ID NO:43, the first VL CDR2 comprises the amino acid sequence of SEQ ID NO:46, and the first VL CDR3 comprises the amino acid sequence of SEQ ID NO:25;
(c) the first VH CDR1 comprises the amino acid sequence of SEQ ID NO:33, the first VH CDR2 comprises the amino acid sequence of SEQ ID NO:21, the first VH CDR3 comprises the amino acid sequence of SEQ ID NO:22, the first VL CDR1 comprises the amino acid sequence of SEQ ID NO:23, the first VL CDR2 comprises the amino acid sequence of SEQ ID NO:24, and the first VL CDR3 comprises the amino acid sequence of SEQ ID NO:25;
(d) the first VH CDR1 comprises the amino acid sequence of SEQ ID NO:34, the first VH CDR2 comprises the amino acid sequence of SEQ ID NO:37, the first VH CDR3 comprises the amino acid sequence of SEQ ID NO:41, the first VL CDR1 comprises the amino acid sequence of SEQ ID NO:44, the first VL CDR2 comprises the amino acid sequence of SEQ ID NO:46, and the first VL CDR3 comprises the amino acid sequence of SEQ ID NO:48;
(e) the first VH CDR1 comprises the amino acid sequence of SEQ ID NO:35, the first VH CDR2 comprises the amino acid sequence of SEQ ID NO:38, the first VH CDR3 comprises the amino acid sequence of SEQ ID NO:42, the first VL CDR1 comprises the amino acid sequence of SEQ ID NO:45, the first VL CDR2 comprises the amino acid sequence of SEQ ID NO:47, and the first VL CDR3 comprises the amino acid sequence of SEQ ID NO:49; or
(f) the first VH CDR1 comprises the amino acid sequence of SEQ ID NO:20, the first VH CDR2 comprises the amino acid sequence of SEQ ID NO:39, the first VH CDR3 comprises the amino acid sequence of SEQ ID NO:22, the first VL CDR1 comprises the amino acid sequence of SEQ ID NO:23, the first VL CDR2 comprises the amino acid sequence of SEQ ID NO:24, and the first VL CDR3 comprises the amino acid sequence of SEQ ID NO:25;
(g) the second VH CDR1 comprises the amino acid sequence of SEQ ID NO:26, the second VH CDR2 comprises the amino acid sequence of SEQ ID NO:27, the second VH CDR3 comprises the amino acid sequence of SEQ ID NO:28, the second VL CDR1 comprises the amino acid sequence of SEQ ID NO:29, the second VL CDR2 comprises the amino acid sequence of SEQ ID NO:30, and the second VL CDR3 comprises the amino acid sequence of SEQ ID NO:31;
(h) the second VH CDR1 comprises the amino acid sequence of SEQ ID NO:50, the second VH CDR2 comprises the amino acid sequence of SEQ ID NO:54, the second VH CDR3 comprises the amino acid sequence of SEQ ID NO:58, the second VL CDR1 comprises the amino acid sequence of SEQ ID NO:61, the second VL CDR2 comprises the amino acid sequence of SEQ ID NO:64, and the second VL CDR3 comprises the amino acid sequence of SEQ ID NO:31;
(i) the second VH CDR1 comprises the amino acid sequence of SEQ ID NO:51, the second VH CDR2 comprises the amino acid sequence of SEQ ID NO:27, the second VH CDR3 comprises the amino acid sequence of SEQ ID NO:28, the second VL CDR1 comprises the amino acid sequence of SEQ ID NO:29, the second VL CDR2 comprises the amino acid sequence of SEQ ID NO:30, and the second VL CDR3 comprises the amino acid sequence of SEQ ID NO:31;
(j) the second VH CDR1 comprises the amino acid sequence of SEQ ID NO:52, the second VH CDR2 comprises the amino acid sequence of SEQ ID NO:55, the second VH CDR3 comprises the amino acid sequence of SEQ ID NO:59, the second VL CDR1 comprises the amino acid sequence of SEQ ID NO:62, the second VL CDR2 comprises the amino acid sequence of SEQ ID NO:64, and the second VL CDR3 comprises the amino acid sequence of SEQ ID NO:66;
(k) the second VH CDR1 comprises the amino acid sequence of SEQ ID NO:53, the second VH CDR2 comprises the amino acid sequence of SEQ ID NO:56, the second VH CDR3 comprises the amino acid sequence of SEQ ID NO:60, the second VL CDR1 comprises the amino acid sequence of SEQ ID NO:63, the second VL CDR2 comprises the amino acid sequence of SEQ ID NO:65, and the second VL CDR3 comprises the amino acid sequence of SEQ ID NO:67; or
(l) the second VH CDR1 comprises the amino acid sequence of SEQ ID NO:26, the second VH CDR2 comprises the amino acid sequence of SEQ ID NO:57, the second VH CDR3 comprises the amino acid sequence of SEQ ID NO:28, the second VL CDR1 comprises the amino acid sequence of SEQ ID NO:29, the second VL CDR2 comprises the amino acid sequence of SEQ ID NO:30, and the second VL CDR3 comprises the amino acid sequence of SEQ ID NO:31.

\* \* \* \* \*

UNITED STATES PATENT AND TRADEMARK OFFICE
CERTIFICATE OF CORRECTION

| | | |
|---|---|---|
| PATENT NO. | : 11,548,942 B2 | Page 1 of 1 |
| APPLICATION NO. | : 16/993974 | |
| DATED | : January 10, 2023 | |
| INVENTOR(S) | : Daniel David Kaplan, Xuecai Ge and Hui Tian | |

It is certified that error appears in the above-identified patent and that said Letters Patent is hereby corrected as shown below:

On the Title Page

Item (56), right column (Other Publications), Line 6:
Delete "glirelin" and insert -- ghrelin --.

Item (56), right column (Other Publications), Line 10:
Delete "[)" and insert -- β --.

Item (56), right column (Other Publications), Line 21:
Delete "Surgerv," and insert -- Surgery, --.

In the Claims

Column 125, Line 48:
In Claim 6, before "least" insert -- at --.

Column 125, Line 50:
In Claim 6, delete "NO:8," and insert -- NO:8; --.

Column 125, Line 57:
In Claim 7, delete "NO:8," and insert -- NO:8; --.

Column 128, Line 24:
In Claim 18, before "least" insert -- at --.

Column 130, Line 48:
In Claim 28, before "least" insert -- at --.

Signed and Sealed this
Twenty-eighth Day of March, 2023

*Katherine Kelly Vidal*

Katherine Kelly Vidal
*Director of the United States Patent and Trademark Office*

SEQUENCE LISTING

<160> NUMBER OF SEQ ID NOS: 78

<210> SEQ ID NO 1
<211> LENGTH: 77
<212> TYPE: PRT
<213> ORGANISM: Homo sapiens

<400> SEQUENCE: 1

Met Trp His Leu Lys Leu Cys Ala Val Leu Met Ile Phe Leu Leu Leu
1               5                   10                  15

Leu Gly Gln Ile Asp Gly Ser Pro Ile Pro Glu Val Ser Ser Ala Lys
            20                  25                  30

Arg Arg Pro Arg Met Thr Pro Phe Trp Arg Gly Val Ser Leu Arg
        35                  40                  45

Pro Ile Gly Ala Ser Cys Arg Asp Asp Ser Glu Cys Ile Thr Arg Leu
    50                  55                  60

Cys Arg Lys Arg Arg Cys Ser Leu Ser Val Ala Gln Glu
65                  70                  75

<210> SEQ ID NO 2
<211> LENGTH: 40
<212> TYPE: PRT
<213> ORGANISM: Homo sapiens

<400> SEQUENCE: 2

Met Thr Pro Phe Trp Arg Gly Val Ser Leu Arg Pro Ile Gly Ala Ser
1               5                   10                  15

Cys Arg Asp Asp Ser Glu Cys Ile Thr Arg Leu Cys Arg Lys Arg Arg
            20                  25                  30

Cys Ser Leu Ser Val Ala Gln Glu
        35                  40

<210> SEQ ID NO 3
<211> LENGTH: 12
<212> TYPE: PRT
<213> ORGANISM: Homo sapiens

<400> SEQUENCE: 3

Gly Val Ser Leu Arg Pro Ile Gly Ala Ser Cys Arg
1               5                   10

<210> SEQ ID NO 4
<211> LENGTH: 20
<212> TYPE: PRT
<213> ORGANISM: Homo sapiens

<400> SEQUENCE: 4

Gly Val Ser Leu Arg Pro Ile Gly Ala Ser Cys Arg Asp Asp Ser Glu
1               5                   10                  15

Cys Ile Thr Arg
            20

<210> SEQ ID NO 5
<211> LENGTH: 366
<212> TYPE: PRT
<213> ORGANISM: Homo sapiens

<400> SEQUENCE: 5

Met Trp Asn Ala Thr Pro Ser Glu Glu Pro Gly Phe Asn Leu Thr Leu
1               5                   10                  15

Ala Asp Leu Asp Trp Asp Ala Ser Pro Gly Asn Asp Ser Leu Gly Asp
            20                  25                  30

Glu Leu Leu Gln Leu Phe Pro Ala Pro Leu Leu Ala Gly Val Thr Ala
        35                  40                  45

Thr Cys Val Ala Leu Phe Val Val Gly Ile Ala Gly Asn Leu Leu Thr
50                  55                  60

Met Leu Val Val Ser Arg Phe Arg Glu Leu Arg Thr Thr Thr Asn Leu
65                  70                  75                  80

Tyr Leu Ser Ser Met Ala Phe Ser Asp Leu Leu Ile Phe Leu Cys Met
                85                  90                  95

Pro Leu Asp Leu Val Arg Leu Trp Gln Tyr Arg Pro Trp Asn Phe Gly
            100                 105                 110

Asp Leu Leu Cys Lys Leu Phe Gln Phe Val Ser Glu Ser Cys Thr Tyr
        115                 120                 125

Ala Thr Val Leu Thr Ile Thr Ala Leu Ser Val Glu Arg Tyr Phe Ala
130                 135                 140

Ile Cys Phe Pro Leu Arg Ala Lys Val Val Thr Lys Gly Arg Val
145                 150                 155                 160

Lys Leu Val Ile Phe Val Ile Trp Ala Val Ala Phe Cys Ser Ala Gly
                165                 170                 175

Pro Ile Phe Val Leu Val Gly Val Glu His Glu Asn Gly Thr Asp Pro
            180                 185                 190

Trp Asp Thr Asn Glu Cys Arg Pro Thr Glu Phe Ala Val Arg Ser Gly
        195                 200                 205

Leu Leu Thr Val Met Val Trp Val Ser Ser Ile Phe Phe Phe Leu Pro
210                 215                 220

Val Phe Cys Leu Thr Val Leu Tyr Ser Leu Ile Gly Arg Lys Leu Trp
225                 230                 235                 240

Arg Arg Arg Arg Gly Asp Ala Val Val Gly Ala Ser Leu Arg Asp Gln
                245                 250                 255

Asn His Lys Gln Thr Val Lys Met Leu Ala Val Val Phe Ala Phe
            260                 265                 270

Ile Leu Cys Trp Leu Pro Phe His Val Gly Arg Tyr Leu Phe Ser Lys
        275                 280                 285

Ser Phe Glu Pro Gly Ser Leu Glu Ile Ala Gln Ile Ser Gln Tyr Cys
290                 295                 300

Asn Leu Val Ser Phe Val Leu Phe Tyr Leu Ser Ala Ala Ile Asn Pro
305                 310                 315                 320

Ile Leu Tyr Asn Ile Met Ser Lys Lys Tyr Arg Val Ala Val Phe Arg
                325                 330                 335

Leu Leu Gly Phe Glu Pro Phe Ser Gln Arg Lys Leu Ser Thr Leu Lys
            340                 345                 350

Asp Glu Ser Ser Arg Ala Trp Thr Glu Ser Ser Ile Asn Thr
        355                 360                 365

<210> SEQ ID NO 6
<211> LENGTH: 289

<212> TYPE: PRT
<213> ORGANISM: Homo sapiens

<400> SEQUENCE: 6

```
Met Trp Asn Ala Thr Pro Ser Glu Glu Pro Gly Phe Asn Leu Thr Leu
1               5                   10                  15

Ala Asp Leu Asp Trp Asp Ala Ser Pro Gly Asn Asp Ser Leu Gly Asp
            20                  25                  30

Glu Leu Leu Gln Leu Phe Pro Ala Pro Leu Leu Ala Gly Val Thr Ala
        35                  40                  45

Thr Cys Val Ala Leu Phe Val Val Gly Ile Ala Gly Asn Leu Leu Thr
    50                  55                  60

Met Leu Val Val Ser Arg Phe Arg Glu Leu Arg Thr Thr Thr Asn Leu
65                  70                  75                  80

Tyr Leu Ser Ser Met Ala Phe Ser Asp Leu Leu Ile Phe Leu Cys Met
                85                  90                  95

Pro Leu Asp Leu Val Arg Leu Trp Gln Tyr Arg Pro Trp Asn Phe Gly
            100                 105                 110

Asp Leu Leu Cys Lys Leu Phe Gln Phe Val Ser Glu Ser Cys Thr Tyr
        115                 120                 125

Ala Thr Val Leu Thr Ile Thr Ala Leu Ser Val Glu Arg Tyr Phe Ala
    130                 135                 140

Ile Cys Phe Pro Leu Arg Ala Lys Val Val Thr Lys Gly Arg Val
145                 150                 155                 160

Lys Leu Val Ile Phe Val Ile Trp Ala Val Ala Phe Cys Ser Ala Gly
                165                 170                 175

Pro Ile Phe Val Leu Val Gly Val Glu His Glu Asn Gly Thr Asp Pro
            180                 185                 190

Trp Asp Thr Asn Glu Cys Arg Pro Thr Glu Phe Ala Val Arg Ser Gly
        195                 200                 205

Leu Leu Thr Val Met Val Trp Val Ser Ser Ile Phe Phe Phe Leu Pro
    210                 215                 220

Val Phe Cys Leu Thr Val Leu Tyr Ser Leu Ile Gly Arg Lys Leu Trp
225                 230                 235                 240

Arg Arg Arg Arg Gly Asp Ala Val Val Gly Ala Ser Leu Arg Asp Gln
                245                 250                 255

Asn His Lys Gln Thr Val Lys Met Leu Gly Gly Ser Arg Ala Leu
            260                 265                 270

Arg Leu Ser Leu Ala Gly Pro Ile Leu Ser Leu Cys Leu Leu Pro Ser
        275                 280                 285

Leu
```

<210> SEQ ID NO 7
<211> LENGTH: 120
<212> TYPE: PRT
<213> ORGANISM: Artificial sequence
<220> FEATURE:
<223> OTHER INFORMATION: synthetic sequence

<400> SEQUENCE: 7

```
Glu Val Gln Leu Gln Gln Ser Gly Thr Val Leu Ala Arg Pro Gly Ala
1               5                   10                  15

Ser Val Lys Met Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45
```

```
Gly Ala Ile Tyr Pro Gly Asn Ser Asp Thr Ser Tyr Lys Gln Lys Phe
        50                  55                  60

Lys Gly Lys Ala Lys Leu Thr Ala Val Thr Ser Ala Ser Thr Val Tyr
 65                  70                  75                  80

Met Glu Leu Ser Ser Leu Thr Asp Glu Asp Ser Ala Val Tyr Tyr Cys
                 85                  90                  95

Thr Tyr Gly Lys Glu Glu Tyr Leu Phe Ala Met Asp Tyr Trp Gly Gln
                100                 105                 110

Gly Thr Ser Val Thr Val Ser Ser
                115                 120

<210> SEQ ID NO 8
<211> LENGTH: 112
<212> TYPE: PRT
<213> ORGANISM: Artificial sequence
<220> FEATURE:
<223> OTHER INFORMATION: synthetic sequence

<400> SEQUENCE: 8

Asp Ile Val Met Ser Gln Ser Pro Ser Ser Leu Ala Val Ser Val Gly
 1               5                  10                  15

Glu Lys Val Thr Met Ser Cys Lys Ser Ser Gln Ser Leu Leu Tyr Ser
                 20                  25                  30

Ser Asn Gln Lys Asn Tyr Leu Ala Trp Tyr Gln Lys Pro Gly Gln
         35                  40                  45

Ser Pro Lys Leu Leu Ile Tyr Trp Ala Ser Thr Arg Glu Ser Gly Val
     50                  55                  60

Pro Asp Arg Phe Thr Gly Ser Gly Ser Gly Thr Asp Phe Thr Leu Thr
 65                  70                  75                  80

Ile Ser Ser Val Lys Ala Glu Asp Leu Ala Val Tyr Tyr Cys Gln Gln
                 85                  90                  95

Tyr Tyr Ser Tyr Pro Thr Phe Gly Gly Gly Thr Lys Leu Lys Ile Lys
                100                 105                 110

<210> SEQ ID NO 9
<211> LENGTH: 118
<212> TYPE: PRT
<213> ORGANISM: Artificial sequence
<220> FEATURE:
<223> OTHER INFORMATION: synthetic sequence

<400> SEQUENCE: 9

Glu Ile Gln Leu Gln Gln Ser Gly Pro Glu Leu Met Lys Pro Gly Ala
 1               5                  10                  15

Ser Val Lys Ile Ser Cys Lys Ala Ser Gly Tyr Ser Phe Thr Asn Tyr
                 20                  25                  30

Tyr Ile His Trp Val Lys Gln Ser His Gly Lys Ser Leu Glu Trp Ile
         35                  40                  45

Gly Tyr Ile Asp Pro Phe Asn Gly Gly Thr Asn Tyr Asn Gln Lys Phe
     50                  55                  60

Lys Gly Lys Ala Thr Leu Thr Val Asp Lys Ser Ser Thr Ala Tyr
 65                  70                  75                  80

Met His Leu Ser Ser Leu Thr Phe Glu Asp Ser Ala Val Tyr Tyr Cys
                 85                  90                  95

Ala Arg Arg Gly Tyr Tyr Tyr Gly Phe Thr Tyr Trp Gly Gln Gly Thr
                100                 105                 110

Leu Val Thr Val Ser Ala
```

115

<210> SEQ ID NO 10
<211> LENGTH: 111
<212> TYPE: PRT
<213> ORGANISM: Artificial sequence
<220> FEATURE:
<223> OTHER INFORMATION: synthetic sequence

<400> SEQUENCE: 10

```
Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Leu Leu Ile Tyr Thr Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Tyr Thr Phe Gly Gly Gly Thr Lys Leu Glu Ile Lys
            100                 105                 110
```

<210> SEQ ID NO 11
<211> LENGTH: 77
<212> TYPE: PRT
<213> ORGANISM: Pan troglodytes

<400> SEQUENCE: 11

```
Met Trp His Leu Lys Leu Cys Ala Val Leu Met Ile Phe Leu Leu Leu
1               5                   10                  15

Leu Gly Gln Ile Asp Gly Ser Pro Ile Pro Glu Val Ser Ser Ala Lys
            20                  25                  30

Arg Arg Pro Arg Arg Met Thr Pro Phe Trp Arg Gly Val Ser Leu Arg
        35                  40                  45

Pro Ile Gly Ala Ser Cys Arg Asp Asp Ser Glu Cys Ile Thr Arg Leu
    50                  55                  60

Cys Arg Lys Arg Arg Cys Ser Leu Ser Val Ala Gln Glu
65                  70                  75
```

<210> SEQ ID NO 12
<211> LENGTH: 77
<212> TYPE: PRT
<213> ORGANISM: Macaca mulatta

<400> SEQUENCE: 12

```
Met Trp His Leu Lys Leu Cys Ala Val Leu Met Ile Phe Leu Leu Leu
1               5                   10                  15

Leu Gly Gln Thr Asp Gly Ser Pro Ile Pro Glu Val Ser Ser Ala Lys
            20                  25                  30

Arg Arg Pro Arg Arg Met Thr Pro Phe Trp Arg Gly Val Ser Leu Arg
        35                  40                  45

Pro Ile Gly Ala Ser Cys Arg Asp Asp Ser Glu Cys Ile Thr Arg Leu
    50                  55                  60

Cys Arg Lys Arg Arg Cys Ser Leu Ser Val Ala Gln Glu
65                  70                  75
```

<210> SEQ ID NO 13
<211> LENGTH: 77
<212> TYPE: PRT
<213> ORGANISM: Macaca fascicularis

<400> SEQUENCE: 13

Met Trp His Leu Lys Leu Cys Ala Val Leu Met Ile Phe Leu Leu Leu
1               5                   10                  15

Leu Gly Gln Thr Asp Gly Ser Pro Ile Pro Glu Val Ser Ser Ala Lys
            20                  25                  30

Arg Arg Pro Arg Arg Met Thr Pro Phe Trp Arg Gly Val Ser Leu Arg
        35                  40                  45

Pro Ile Gly Ala Ser Cys Arg Asp Asp Ser Glu Cys Ile Thr Arg Leu
    50                  55                  60

Cys Arg Lys Arg Arg Cys Ser Leu Ser Val Ala Gln Glu
65                  70                  75

<210> SEQ ID NO 14
<211> LENGTH: 71
<212> TYPE: PRT
<213> ORGANISM: Cavia porcellus

<400> SEQUENCE: 14

Ser Val Val Leu Leu Ile Cys Leu Leu Leu Gly Gln Val Asp Gly
1               5                   10                  15

Ser Pro Val Pro Glu Lys Ser Ser Val Lys Arg Leu Arg Arg Met
            20                  25                  30

Thr Pro Phe Trp Arg Gly Val Ser Leu Arg Pro Ile Gly Ala Ser Cys
        35                  40                  45

Arg Asp Asp Ser Glu Cys Ile Thr Arg Leu Cys Lys Lys Arg Arg Cys
    50                  55                  60

Ser Leu Ser Val Ala Gln Glu
65                  70

<210> SEQ ID NO 15
<211> LENGTH: 77
<212> TYPE: PRT
<213> ORGANISM: Bos taurus

<400> SEQUENCE: 15

Met Trp His Leu Lys Leu Phe Ala Val Leu Met Ile Cys Leu Leu Leu
1               5                   10                  15

Leu Ala Gln Val Asp Gly Ser Pro Ile Pro Gln Gln Ser Ser Ala Lys
            20                  25                  30

Arg Arg Pro Arg Arg Met Thr Pro Phe Trp Arg Ala Val Ser Leu Arg
        35                  40                  45

Pro Ile Gly Ala Ser Cys Arg Asp Asp Ser Glu Cys Ile Thr Arg Leu
    50                  55                  60

Cys Arg Lys Arg Arg Cys Ser Leu Ser Val Ala Gln Glu
65                  70                  75

<210> SEQ ID NO 16
<211> LENGTH: 76
<212> TYPE: PRT
<213> ORGANISM: Mus musculus

<400> SEQUENCE: 16

Met Leu Gln Leu Lys Leu Phe Ala Val Leu Leu Thr Cys Leu Leu Leu
1               5                   10                  15

Leu Gly Gln Val Asn Ser Ser Pro Val Pro Glu Val Ser Ala Lys
            20                  25                  30

Arg Ser Arg Arg Met Thr Pro Phe Trp Arg Gly Val Ser Leu Arg Pro
                35                  40                  45

Ile Gly Ala Ser Cys Arg Asp Asp Ser Glu Cys Ile Thr Arg Leu Cys
 50                  55                  60

Arg Lys Arg Arg Cys Ser Leu Ser Val Ala Gln Glu
 65                  70                  75

<210> SEQ ID NO 17
<211> LENGTH: 77
<212> TYPE: PRT
<213> ORGANISM: Oryctolagus cuniculus

<400> SEQUENCE: 17

Met Trp His Leu Lys Leu Phe Ala Val Leu Met Ile Cys Leu Leu Leu
 1               5                  10                  15

Leu Gly Gln Val Asp Gly Ser Pro Val Pro Glu Leu Ser Ala Lys
            20                  25                  30

Arg Arg Pro Arg Arg Met Thr Pro Phe Trp Arg Gly Val Ser Leu Arg
                35                  40                  45

Pro Ile Gly Ala Ser Cys Arg Asp Asn Ala Glu Cys Val Thr Arg Leu
 50                  55                  60

Cys Arg Lys Arg Arg Cys Ser Leu Ser Val Ala Gln Glu
 65                  70                  75

<210> SEQ ID NO 18
<211> LENGTH: 75
<212> TYPE: PRT
<213> ORGANISM: Rattus norvegicus

<400> SEQUENCE: 18

Leu Gln Leu Lys Leu Phe Ala Val Leu Leu Thr Cys Leu Leu Leu
 1               5                  10                  15

Gly Gln Ala Gln Ser Ser Pro Val Pro Glu Leu Ser Ser Ala Lys Arg
            20                  25                  30

Thr Arg Arg Met Thr Pro Phe Trp Arg Gly Val Ser Leu Arg Pro Ile
                35                  40                  45

Gly Ala Ser Cys Arg Asp Asp Ser Glu Cys Ile Thr Arg Leu Cys Lys
 50                  55                  60

Arg Arg Arg Cys Ser Leu Ser Val Ala Gln Glu
 65                  70                  75

<210> SEQ ID NO 19
<211> LENGTH: 76
<212> TYPE: PRT
<213> ORGANISM: Gallus gallus domesticus

<400> SEQUENCE: 19

Met His Cys Leu Lys Ile Met Ala Phe Leu Leu Phe Phe Ser Leu Leu
 1               5                  10                  15

Leu Ser Gln Val Cys Cys Ala Ser Leu His Gln Pro Gln Pro Leu Leu
            20                  25                  30

Arg Leu Lys Arg Met Thr Pro Phe Trp Arg Gly Val Ser Leu Arg Pro
                35                  40                  45

Val Gly Ala Ser Cys Arg Asp Asn Ser Glu Cys Ile Thr Met Leu Cys
 50                  55                  60

Arg Lys Asn Arg Cys Phe Leu Arg Thr Ala Ser Glu
65                  70                  75

<210> SEQ ID NO 20
<211> LENGTH: 10
<212> TYPE: PRT
<213> ORGANISM: Artificial sequence
<220> FEATURE:
<223> OTHER INFORMATION: synthetic sequence

<400> SEQUENCE: 20

Gly Tyr Thr Phe Thr Ser Tyr Trp Met His
1               5                   10

<210> SEQ ID NO 21
<211> LENGTH: 17
<212> TYPE: PRT
<213> ORGANISM: Artificial sequence
<220> FEATURE:
<223> OTHER INFORMATION: synthetic sequence

<400> SEQUENCE: 21

Ala Ile Tyr Pro Gly Asn Ser Asp Thr Ser Tyr Lys Gln Lys Phe Lys
1               5                   10                  15

Gly

<210> SEQ ID NO 22
<211> LENGTH: 11
<212> TYPE: PRT
<213> ORGANISM: Artificial sequence
<220> FEATURE:
<223> OTHER INFORMATION: synthetic sequence

<400> SEQUENCE: 22

Gly Lys Glu Glu Tyr Leu Phe Ala Met Asp Tyr
1               5                   10

<210> SEQ ID NO 23
<211> LENGTH: 17
<212> TYPE: PRT
<213> ORGANISM: Artificial sequence
<220> FEATURE:
<223> OTHER INFORMATION: synthetic sequence

<400> SEQUENCE: 23

Lys Ser Ser Gln Ser Leu Leu Tyr Ser Ser Asn Gln Lys Asn Tyr Leu
1               5                   10                  15

Ala

<210> SEQ ID NO 24
<211> LENGTH: 7
<212> TYPE: PRT
<213> ORGANISM: Artificial sequence
<220> FEATURE:
<223> OTHER INFORMATION: synthetic sequence

<400> SEQUENCE: 24

Trp Ala Ser Thr Arg Glu Ser
1               5

<210> SEQ ID NO 25
<211> LENGTH: 8
<212> TYPE: PRT
<213> ORGANISM: Artificial sequence
<220> FEATURE:
<223> OTHER INFORMATION: synthetic sequence

<400> SEQUENCE: 25

Gln Gln Tyr Tyr Ser Tyr Pro Thr
1               5

<210> SEQ ID NO 26
<211> LENGTH: 10
<212> TYPE: PRT
<213> ORGANISM: Artificial sequence
<220> FEATURE:
<223> OTHER INFORMATION: synthetic sequence

<400> SEQUENCE: 26

Gly Tyr Ser Phe Thr Asn Tyr Tyr Ile His
1               5                   10

<210> SEQ ID NO 27
<211> LENGTH: 17
<212> TYPE: PRT
<213> ORGANISM: Artificial sequence
<220> FEATURE:
<223> OTHER INFORMATION: synthetic sequence

<400> SEQUENCE: 27

Tyr Ile Asp Pro Phe Asn Gly Gly Thr Asn Tyr Asn Gln Lys Phe Lys
1               5                   10                  15

Gly

<210> SEQ ID NO 28
<211> LENGTH: 9
<212> TYPE: PRT
<213> ORGANISM: Artificial sequence
<220> FEATURE:
<223> OTHER INFORMATION: synthetic sequence

<400> SEQUENCE: 28

Arg Gly Tyr Tyr Tyr Gly Phe Thr Tyr
1               5

<210> SEQ ID NO 29
<211> LENGTH: 15
<212> TYPE: PRT
<213> ORGANISM: Artificial sequence
<220> FEATURE:
<223> OTHER INFORMATION: synthetic sequence

<400> SEQUENCE: 29

Lys Ala Ser Gln Ser Val Asp Tyr Asp Gly Asp Ser Tyr Met Asn
1               5                   10                  15

<210> SEQ ID NO 30
<211> LENGTH: 7
<212> TYPE: PRT
<213> ORGANISM: Artificial sequence
<220> FEATURE:
<223> OTHER INFORMATION: synthetic sequence

<400> SEQUENCE: 30

Thr Ala Ser Asn Leu Glu Ser
1               5

<210> SEQ ID NO 31
<211> LENGTH: 9
<212> TYPE: PRT
<213> ORGANISM: Artificial sequence
<220> FEATURE:

```
<223> OTHER INFORMATION: synthetic sequence

<400> SEQUENCE: 31

Gln Gln Ser Asn Glu Asp Pro Tyr Thr
1               5

<210> SEQ ID NO 32
<211> LENGTH: 8
<212> TYPE: PRT
<213> ORGANISM: Artificial sequence
<220> FEATURE:
<223> OTHER INFORMATION: synthetic sequence

<400> SEQUENCE: 32

Gly Tyr Thr Phe Thr Ser Tyr Trp
1               5

<210> SEQ ID NO 33
<211> LENGTH: 5
<212> TYPE: PRT
<213> ORGANISM: Artificial sequence
<220> FEATURE:
<223> OTHER INFORMATION: synthetic sequence

<400> SEQUENCE: 33

Ser Tyr Trp Met His
1               5

<210> SEQ ID NO 34
<211> LENGTH: 7
<212> TYPE: PRT
<213> ORGANISM: Artificial sequence
<220> FEATURE:
<223> OTHER INFORMATION: synthetic sequence

<400> SEQUENCE: 34

Gly Tyr Thr Phe Thr Ser Tyr
1               5

<210> SEQ ID NO 35
<211> LENGTH: 6
<212> TYPE: PRT
<213> ORGANISM: Artificial sequence
<220> FEATURE:
<223> OTHER INFORMATION: synthetic sequence

<400> SEQUENCE: 35

Thr Ser Tyr Trp Met His
1               5

<210> SEQ ID NO 36
<211> LENGTH: 8
<212> TYPE: PRT
<213> ORGANISM: Artificial sequence
<220> FEATURE:
<223> OTHER INFORMATION: synthetic sequence

<400> SEQUENCE: 36

Ile Tyr Pro Gly Asn Ser Asp Thr
1               5

<210> SEQ ID NO 37
<211> LENGTH: 4
<212> TYPE: PRT
<213> ORGANISM: Artificial sequence
<220> FEATURE:
<223> OTHER INFORMATION: synthetic sequence
```

<400> SEQUENCE: 37

Pro Gly Asn Ser
1

<210> SEQ ID NO 38
<211> LENGTH: 13
<212> TYPE: PRT
<213> ORGANISM: Artificial sequence
<220> FEATURE:
<223> OTHER INFORMATION: synthetic sequence

<400> SEQUENCE: 38

Trp Ile Gly Ala Ile Tyr Pro Gly Asn Ser Asp Thr Ser
1               5                   10

<210> SEQ ID NO 39
<211> LENGTH: 10
<212> TYPE: PRT
<213> ORGANISM: Artificial sequence
<220> FEATURE:
<223> OTHER INFORMATION: synthetic sequence

<400> SEQUENCE: 39

Ala Ile Tyr Pro Gly Asn Ser Asp Thr Ser
1               5                   10

<210> SEQ ID NO 40
<211> LENGTH: 13
<212> TYPE: PRT
<213> ORGANISM: Artificial sequence
<220> FEATURE:
<223> OTHER INFORMATION: synthetic sequence

<400> SEQUENCE: 40

Thr Tyr Gly Lys Glu Glu Tyr Leu Phe Ala Met Asp Tyr
1               5                   10

<210> SEQ ID NO 41
<211> LENGTH: 9
<212> TYPE: PRT
<213> ORGANISM: Artificial sequence
<220> FEATURE:
<223> OTHER INFORMATION: synthetic sequence

<400> SEQUENCE: 41

Lys Glu Glu Tyr Leu Phe Ala Met Asp
1               5

<210> SEQ ID NO 42
<211> LENGTH: 12
<212> TYPE: PRT
<213> ORGANISM: Artificial sequence
<220> FEATURE:
<223> OTHER INFORMATION: synthetic sequence

<400> SEQUENCE: 42

Thr Tyr Gly Lys Glu Glu Tyr Leu Phe Ala Met Asp
1               5                   10

<210> SEQ ID NO 43
<211> LENGTH: 12
<212> TYPE: PRT
<213> ORGANISM: Artificial sequence
<220> FEATURE:
<223> OTHER INFORMATION: synthetic sequence

```
<400> SEQUENCE: 43

Gln Ser Leu Leu Tyr Ser Ser Asn Gln Lys Asn Tyr
1               5                   10

<210> SEQ ID NO 44
<211> LENGTH: 13
<212> TYPE: PRT
<213> ORGANISM: Artificial sequence
<220> FEATURE:
<223> OTHER INFORMATION: synthetic sequence

<400> SEQUENCE: 44

Ser Gln Ser Leu Leu Tyr Ser Ser Asn Gln Lys Asn Tyr
1               5                   10

<210> SEQ ID NO 45
<211> LENGTH: 13
<212> TYPE: PRT
<213> ORGANISM: Artificial sequence
<220> FEATURE:
<223> OTHER INFORMATION: synthetic sequence

<400> SEQUENCE: 45

Leu Tyr Ser Ser Asn Gln Lys Asn Tyr Leu Ala Trp Tyr
1               5                   10

<210> SEQ ID NO 46
<211> LENGTH: 3
<212> TYPE: PRT
<213> ORGANISM: Artificial sequence
<220> FEATURE:
<223> OTHER INFORMATION: synthetic sequence

<400> SEQUENCE: 46

Trp Ala Ser
1

<210> SEQ ID NO 47
<211> LENGTH: 10
<212> TYPE: PRT
<213> ORGANISM: Artificial sequence
<220> FEATURE:
<223> OTHER INFORMATION: synthetic sequence

<400> SEQUENCE: 47

Leu Leu Ile Tyr Trp Ala Ser Thr Arg Glu
1               5                   10

<210> SEQ ID NO 48
<211> LENGTH: 5
<212> TYPE: PRT
<213> ORGANISM: Artificial sequence
<220> FEATURE:
<223> OTHER INFORMATION: synthetic sequence

<400> SEQUENCE: 48

Tyr Tyr Ser Tyr Pro
1               5

<210> SEQ ID NO 49
<211> LENGTH: 7
<212> TYPE: PRT
<213> ORGANISM: Artificial sequence
<220> FEATURE:
<223> OTHER INFORMATION: synthetic sequence

<400> SEQUENCE: 49
```

```
Gln Gln Tyr Tyr Ser Tyr Pro
1               5

<210> SEQ ID NO 50
<211> LENGTH: 8
<212> TYPE: PRT
<213> ORGANISM: Artificial sequence
<220> FEATURE:
<223> OTHER INFORMATION: synthetic sequence

<400> SEQUENCE: 50

Gly Tyr Ser Phe Thr Asn Tyr Tyr
1               5

<210> SEQ ID NO 51
<211> LENGTH: 5
<212> TYPE: PRT
<213> ORGANISM: Artificial sequence
<220> FEATURE:
<223> OTHER INFORMATION: synthetic sequence

<400> SEQUENCE: 51

Asn Tyr Tyr Ile His
1               5

<210> SEQ ID NO 52
<211> LENGTH: 7
<212> TYPE: PRT
<213> ORGANISM: Artificial sequence
<220> FEATURE:
<223> OTHER INFORMATION: synthetic sequence

<400> SEQUENCE: 52

Gly Tyr Ser Phe Thr Asn Tyr
1               5

<210> SEQ ID NO 53
<211> LENGTH: 6
<212> TYPE: PRT
<213> ORGANISM: Artificial sequence
<220> FEATURE:
<223> OTHER INFORMATION: synthetic sequence

<400> SEQUENCE: 53

Thr Asn Tyr Tyr Ile His
1               5

<210> SEQ ID NO 54
<211> LENGTH: 8
<212> TYPE: PRT
<213> ORGANISM: Artificial sequence
<220> FEATURE:
<223> OTHER INFORMATION: synthetic sequence

<400> SEQUENCE: 54

Ile Asp Pro Phe Asn Gly Gly Thr
1               5

<210> SEQ ID NO 55
<211> LENGTH: 4
<212> TYPE: PRT
<213> ORGANISM: Artificial sequence
<220> FEATURE:
<223> OTHER INFORMATION: synthetic sequence

<400> SEQUENCE: 55
```

Pro Phe Asn Gly
1

<210> SEQ ID NO 56
<211> LENGTH: 13
<212> TYPE: PRT
<213> ORGANISM: Artificial sequence
<220> FEATURE:
<223> OTHER INFORMATION: synthetic sequence

<400> SEQUENCE: 56

Trp Ile Gly Tyr Ile Asp Pro Phe Asn Gly Gly Thr Asn
1               5                   10

<210> SEQ ID NO 57
<211> LENGTH: 10
<212> TYPE: PRT
<213> ORGANISM: Artificial sequence
<220> FEATURE:
<223> OTHER INFORMATION: synthetic sequence

<400> SEQUENCE: 57

Tyr Ile Asp Pro Phe Asn Gly Gly Thr Asn
1               5                   10

<210> SEQ ID NO 58
<211> LENGTH: 11
<212> TYPE: PRT
<213> ORGANISM: Artificial sequence
<220> FEATURE:
<223> OTHER INFORMATION: synthetic sequence

<400> SEQUENCE: 58

Ala Arg Arg Gly Tyr Tyr Tyr Gly Phe Thr Tyr
1               5                   10

<210> SEQ ID NO 59
<211> LENGTH: 7
<212> TYPE: PRT
<213> ORGANISM: Artificial sequence
<220> FEATURE:
<223> OTHER INFORMATION: synthetic sequence

<400> SEQUENCE: 59

Gly Tyr Tyr Tyr Gly Phe Thr
1               5

<210> SEQ ID NO 60
<211> LENGTH: 10
<212> TYPE: PRT
<213> ORGANISM: Artificial sequence
<220> FEATURE:
<223> OTHER INFORMATION: synthetic sequence

<400> SEQUENCE: 60

Ala Arg Arg Gly Tyr Tyr Tyr Gly Phe Thr
1               5                   10

<210> SEQ ID NO 61
<211> LENGTH: 10
<212> TYPE: PRT
<213> ORGANISM: Artificial sequence
<220> FEATURE:
<223> OTHER INFORMATION: synthetic sequence

<400> SEQUENCE: 61

Gln Ser Val Asp Tyr Asp Gly Asp Ser Tyr

```
1               5                   10

<210> SEQ ID NO 62
<211> LENGTH: 11
<212> TYPE: PRT
<213> ORGANISM: Artificial sequence
<220> FEATURE:
<223> OTHER INFORMATION: synthetic sequence

<400> SEQUENCE: 62

Ser Gln Ser Val Asp Tyr Asp Gly Asp Ser Tyr
1               5                   10

<210> SEQ ID NO 63
<211> LENGTH: 11
<212> TYPE: PRT
<213> ORGANISM: Artificial sequence
<220> FEATURE:
<223> OTHER INFORMATION: synthetic sequence

<400> SEQUENCE: 63

Asp Tyr Asp Gly Asp Ser Tyr Met Asn Trp Tyr
1               5                   10

<210> SEQ ID NO 64
<211> LENGTH: 3
<212> TYPE: PRT
<213> ORGANISM: Artificial sequence
<220> FEATURE:
<223> OTHER INFORMATION: synthetic sequence

<400> SEQUENCE: 64

Thr Ala Ser
1

<210> SEQ ID NO 65
<211> LENGTH: 10
<212> TYPE: PRT
<213> ORGANISM: Artificial sequence
<220> FEATURE:
<223> OTHER INFORMATION: synthetic sequence

<400> SEQUENCE: 65

Leu Leu Ile Tyr Thr Ala Ser Asn Leu Glu
1               5                   10

<210> SEQ ID NO 66
<211> LENGTH: 6
<212> TYPE: PRT
<213> ORGANISM: Artificial sequence
<220> FEATURE:
<223> OTHER INFORMATION: synthetic sequence

<400> SEQUENCE: 66

Ser Asn Glu Asp Pro Tyr
1               5

<210> SEQ ID NO 67
<211> LENGTH: 8
<212> TYPE: PRT
<213> ORGANISM: Artificial sequence
<220> FEATURE:
<223> OTHER INFORMATION: synthetic sequence

<400> SEQUENCE: 67

Gln Gln Ser Asn Glu Asp Pro Tyr
1               5
```

```
<210> SEQ ID NO 68
<211> LENGTH: 330
<212> TYPE: PRT
<213> ORGANISM: Artificial sequence
<220> FEATURE:
<223> OTHER INFORMATION: synthetic sequence

<400> SEQUENCE: 68

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 69
<211> LENGTH: 327
<212> TYPE: PRT
<213> ORGANISM: Artificial sequence
```

<220> FEATURE:
<223> OTHER INFORMATION: synthetic sequence

<400> SEQUENCE: 69

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 70
<211> LENGTH: 330
<212> TYPE: PRT
<213> ORGANISM: Artificial sequence
<220> FEATURE:
<223> OTHER INFORMATION: synthetic sequence

<400> SEQUENCE: 70

Ala Ser Thr Lys Gly Pro Ser Val Phe Pro Leu Ala Pro Ser Ser Lys

```
            1               5                  10                 15
       Ser Thr Ser Gly Gly Thr Ala Ala Leu Gly Cys Leu Val Lys Asp Tyr
                    20                  25                 30

Phe Pro Glu Pro Val Thr Val Ser Trp Asn Ser Gly Ala Leu Thr Ser
                    35                  40                 45

Gly Val His Thr Phe Pro Ala Val Leu Gln Ser Ser Gly Leu Tyr Ser
                    50                  55                 60

Leu Ser Ser Val Val Thr Val Pro Ser Ser Leu Gly Thr Gln Thr
        65                  70                  75                 80

Tyr Ile Cys Asn Val Asn His Lys Pro Ser Asn Thr Lys Val Asp Lys
                            85                  90                 95

Lys Val Glu Pro Lys Ser Cys Asp Lys Thr His Thr Cys Pro Pro Cys
                       100                 105                110

Pro Ala Pro Ala Leu Ala Gly Gly Pro Ser Val Phe Leu Phe Pro Pro
                       115                 120                125

Lys Pro Lys Asp Thr Leu Met Ile Ser Arg Thr Pro Glu Val Thr Cys
                130                 135                 140

Val Val Val Asp Val Ser His Glu Asp Pro Glu Val Lys Phe Asn Trp
        145                 150                 155                160

Tyr Val Asp Gly Val Glu Val His Asn Ala Lys Thr Lys Pro Arg Glu
                       165                 170                175

Glu Gln Tyr Asn Ser Thr Tyr Arg Val Val Ser Val Leu Thr Val Leu
                       180                 185                190

His Gln Asp Trp Leu Asn Gly Lys Glu Tyr Lys Cys Lys Val Ser Asn
                       195                 200                205

Lys Ala Leu Pro Ala Pro Ile Glu Lys Thr Ile Ser Lys Ala Lys Gly
                       210                 215                220

Gln Pro Arg Glu Pro Gln Val Tyr Thr Leu Pro Pro Ser Arg Glu Glu
        225                 230                 235                240

Met Thr Lys Asn Gln Val Ser Leu Thr Cys Leu Val Lys Gly Phe Tyr
                       245                 250                255

Pro Ser Asp Ile Ala Val Glu Trp Glu Ser Asn Gly Gln Pro Glu Asn
                       260                 265                270

Asn Tyr Lys Thr Thr Pro Pro Val Leu Asp Ser Asp Gly Ser Phe Phe
                       275                 280                285

Leu Tyr Ser Lys Leu Thr Val Asp Lys Ser Arg Trp Gln Gln Gly Asn
                       290                 295                300

Val Phe Ser Cys Ser Val Met His Glu Ala Leu His Asn His Tyr Thr
        305                 310                 315                320

Gln Lys Ser Leu Ser Leu Ser Pro Gly Lys
                       325                 330

<210> SEQ ID NO 71
<211> LENGTH: 329
<212> TYPE: PRT
<213> ORGANISM: Artificial sequence
<220> FEATURE:
<223> OTHER INFORMATION: synthetic sequence

<400> SEQUENCE: 71

Ala Ser Thr Lys Gly Pro Ser Val Phe Pro Leu Ala Pro Ser Ser Lys
1               5                  10                 15

Ser Thr Ser Gly Gly Thr Ala Ala Leu Gly Cys Leu Val Lys Asp Tyr
            20                  25                 30

Phe Pro Glu Pro Val Thr Val Ser Trp Asn Ser Gly Ala Leu Thr Ser
```

```
            35                  40                  45
Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
                100                 105                 110

Pro Ala Pro Ala Leu Ala Gly Gly Pro Ser Val Phe Leu Phe Pro Pro
                115                 120                 125

Lys Pro Lys Asp Thr Leu Met Ile Ser Arg Thr Pro Glu Val Thr Cys
                130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 72
<211> LENGTH: 329
<212> TYPE: PRT
<213> ORGANISM: Artificial sequence
<220> FEATURE:
<223> OTHER INFORMATION: synthetic sequence

<400> SEQUENCE: 72

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
                 35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
```

```
                65                  70                  75                  80
Tyr Ile Cys Asn Val Asn His Lys Pro Ser Asn Thr Lys Val Asp Lys
                    85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 73
<211> LENGTH: 330
<212> TYPE: PRT
<213> ORGANISM: Artificial sequence
<220> FEATURE:
<223> OTHER INFORMATION: synthetic sequence

<400> SEQUENCE: 73

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                    85                  90                  95

Lys Val Glu Pro Lys Ser Cys Asp Lys Thr His Thr Cys Pro Pro Cys
```

-continued

```
                100                 105                 110
Pro Ala Pro Glu Leu Leu Gly Gly Pro Ser Val Phe Leu Phe Pro Pro
            115                 120                 125
Lys Pro Lys Asp Thr Leu Met Ile Ser Arg Thr Pro Glu Val Thr Cys
            130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Gln Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
            195                 200                 205
Lys Ala Leu Pro Ala Pro Ile Glu Lys Thr Ile Ser Lys Ala Lys Gly
            210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
                260                 265                 270
Asn Tyr Lys Thr Thr Pro Pro Val Leu Asp Ser Asp Gly Ser Phe Phe
            275                 280                 285
Leu Tyr Ser Lys Leu Thr Val Asp Lys Ser Arg Trp Gln Gln Gly Asn
            290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 74
<211> LENGTH: 330
<212> TYPE: PRT
<213> ORGANISM: Artificial sequence
<220> FEATURE:
<223> OTHER INFORMATION: synthetic sequence

<400> SEQUENCE: 74

Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
            50                  55                  60
Leu Ser Ser Val Val Thr Val Pro Ser Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
                100                 105                 110
Pro Ala Pro Glu Ala Ala Gly Gly Pro Ser Val Phe Leu Phe Pro Pro
            115                 120                 125
Lys Pro Lys Asp Thr Leu Met Ile Ser Arg Thr Pro Glu Val Thr Cys
```

```
                130                 135                 140
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Pro Ile Glu Lys Thr Ile Ser Lys Ala Lys Gly
                210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 75
<211> LENGTH: 330
<212> TYPE: PRT
<213> ORGANISM: Artificial sequence
<220> FEATURE:
<223> OTHER INFORMATION: synthetic sequence

<400> SEQUENCE: 75

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
                100                 105                 110

Pro Ala Pro Glu Ala Ala Gly Gly Pro Ser Val Phe Leu Phe Pro Pro
                115                 120                 125

Lys Pro Lys Asp Thr Leu Met Ile Ser Arg Thr Pro Glu Val Thr Cys
                130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
```

```
                    165                 170                 175
Glu Gln Tyr Asn Ser Thr Tyr Arg Val Val Ser Val Leu Thr Val Leu
                180                 185                 190
His Gln Asp Trp Leu Asn Gly Lys Glu Tyr Lys Cys Lys Val Ser Asn
                195                 200                 205
Lys Ala Leu Gly Ala Pro Ile Glu Lys Thr Ile Ser Lys Ala Lys Gly
                210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
                260                 265                 270
Asn Tyr Lys Thr Thr Pro Pro Val Leu Asp Ser Asp Gly Ser Phe Phe
                275                 280                 285
Leu Tyr Ser Lys Leu Thr Val Asp Lys Ser Arg Trp Gln Gln Gly Asn
                290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 76
<211> LENGTH: 327
<212> TYPE: PRT
<213> ORGANISM: Artificial sequence
<220> FEATURE:
<223> OTHER INFORMATION: synthetic sequence

<400> SEQUENCE: 76

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
                20                  25                  30
Phe Pro Glu Pro Val Thr Val Ser Trp Asn Ser Gly Ala Leu Thr Ser
                35                  40                  45
Gly Val His Thr Phe Pro Ala Val Leu Gln Ser Ser Gly Leu Tyr Ser
                50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Pro Cys Pro Ala Pro
                100                 105                 110
Glu Phe Leu Gly Gly Pro Ser Val Phe Leu Phe Pro Pro Lys Pro Lys
                115                 120                 125
Asp Thr Leu Met Ile Ser Arg Thr Pro Glu Val Thr Cys Val Val Val
                130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
                180                 185                 190
Trp Leu Asn Gly Lys Glu Tyr Lys Cys Lys Val Ser Asn Lys Gly Leu
```

195                 200                 205
Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 77
<211> LENGTH: 326
<212> TYPE: PRT
<213> ORGANISM: Artificial sequence
<220> FEATURE:
<223> OTHER INFORMATION: synthetic sequence

<400> SEQUENCE: 77

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys

```
                225                 230                 235                 240
Asn Gln Val Ser Leu Thr Cys Leu Val Lys Gly Phe Tyr Pro Ser Asp
                    245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 78
<211> LENGTH: 327
<212> TYPE: PRT
<213> ORGANISM: Artificial sequence
<220> FEATURE:
<223> OTHER INFORMATION: synthetic sequence

<400> SEQUENCE: 78

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
```

-continued

```
                260                 265                 270
Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```